United States Patent [19]
Akahoshi et al.

[11] Patent Number: 6,080,738
[45] Date of Patent: Jun. 27, 2000

[54] HETEROCYCLIC AMIDE COMPOUNDS AND MEDICINAL USES THEREOF

[75] Inventors: Fumihiko Akahoshi; Atsuyuki Ashimori; Takuya Yoshimura; Masahiro Eda; Hiroshi Sakashita; Masahide Nakajima; Teruaki Imada, all of Hirakata, Japan

[73] Assignee: Yoshitomi Pharmaceuticals Industries, Ltd., Japan

[21] Appl. No.: 09/284,877

[22] PCT Filed: Oct. 22, 1997

[86] PCT No.: PCT/JP97/03839

§ 371 Date: Apr. 22, 1999

§ 102(e) Date: Apr. 22, 1999

[87] PCT Pub. No.: WO98/18794

PCT Pub. Date: May 7, 1998

[30] Foreign Application Priority Data

Oct. 25, 1996 [JP] Japan .................................. 8-284471
Jul. 18, 1997 [JP] Japan .................................. 9-194106

[51] Int. Cl.[7] .................... C07D 413/12; C07D 417/12; C07D 498/04; C07D 239/47; C07K 5/04; A61K 31/505

[52] U.S. Cl. .................... 514/227.8; 544/319; 544/58.2; 544/58.4; 544/58.6; 544/60; 544/123; 544/131; 544/295; 544/360; 514/269; 514/235.8; 514/237.2; 514/255; 514/242; 514/245

[58] Field of Search .................... 514/269, 227.8, 514/235.8, 237.2, 255, 242, 245; 544/319, 58.2, 58.4, 58.6, 60, 123, 131, 295, 360

[56] References Cited

FOREIGN PATENT DOCUMENTS

| | | |
|---|---|---|
| 509769 A1 | 10/1992 | European Pat. Off. . |
| 528633 A1 | 2/1993 | European Pat. Off. . |
| WO 96/33974 | 10/1996 | Japan . |
| 93/21210 | 10/1993 | WIPO . |
| 93/25574 | 12/1993 | WIPO . |
| 95/35308 | 12/1995 | WIPO . |

*Primary Examiner*—Mukund J. Shah
*Assistant Examiner*—Hong Liu
*Attorney, Agent, or Firm*—Wenderoth, Lind & Ponack, L.L.P.

[57] ABSTRACT

A heterocyclic amide compound of the formula (I)

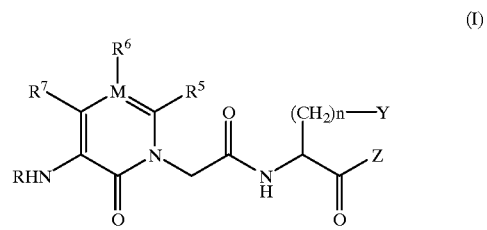

wherein each symbol is as defined in the specification, a pharmacologically acceptable salt thereof, a pharmaceutical composition thereof and a pharmaceutical use thereof. The heterocyclic amide compound and a pharmacologically acceptable salt thereof of the present invention have superior inhibitory action on chymase group in mammals inclusive of human, and can be administered orally or parenterally. Therefore, they are useful as chymase inhibitors and can be used for the prophylaxis and treatment of various diseases caused by chymase, such as those caused by angiotensin II.

9 Claims, No Drawings

HETEROCYCLIC AMIDE COMPOUNDS AND MEDICINAL USES THEREOF

TECHNICAL FIELD

The present invention relates to a novel heterocyclic amide compound, a pharmacologically acceptable salt thereof, a pharmaceutical composition thereof, and a pharmaceutical use thereof. More particularly, the present invention relates to pyridoneacetamide and pyrimidoneacetamide derivatives useful pharmacologically, diagnostically and for the prophylaxis and treatment of diseases, and a pharmacologically acceptable salt thereof. Moreover, the present invention relates to an intermediate necessary for the synthesis of the above-mentioned heterocyclic amide compound.

BACKGROUND ART

Angiotensin II shows physiological activities such as vasopression by strong contraction of blood vessel, stimulation of aldosterone secretion from adrenal cortex (aldosterone retains sodium), and the like, and is considered to be a causative substance or risk factor of diseases such as hypertension, hypercardia, myocardial infarction, arteriosclerosis, diabetic and non-diabetic renal diseases, vascular restenosis after PTCA (percutaneous transluminal coronary angioplasty) and the like.

It is known that this angiotensin II is generated by cleavage of two amino acid residues from angiotensin I, which is a peptide consisting of ten amino acids present in a living body, and that angiotensin converting enzyme (ACE) is involved in said cleavage. Thus, numerous ACE inhibitors have been developed for the prophylaxis and treatment of the above-mentioned diseases.

Meanwhile, actions of a chymase group including human heart chymase, human mast cell chymase and human cutis chymase, which is one of the subfamilies of serine protease, have been drawing attention in recent years.

It has been clarified that chymase is involved in the course of generation, which is independent from ACE, of angiotensin II in the conversion of the above-mentioned angiotensin I to angiotensin II (Okunishi et al., Jpn. J. Pharmacol. 1993, 62, p. 207 etc. and others). Also, chymase is known to use, as substrates, numerous physiologically active substances such as extracellular matrix, cytokine, substance P, VIP (vasoactive intestinal polypeptide), apoprotein B and the like, and known to be responsible for the activation of other proteases such as collagenase (Igakuno ayumi, Miyazaki et al., 1995, 172, p. 559).

Therefore, chymase inhibitors are expected to become inhibitors of angiotensin II action, as well as agents for the prophylaxis and treatment of various diseases caused by chymase, since it inhibits generation of ACE non-dependent angiotensin II. A patent application drawn to a chymase inhibitor based on these ideas has been already filed (WO93/25574).

The above-mentioned patent application WO93/25574 in the name of PFIZER Inc. discloses a series of peptide compounds which are chymase (inclusive of human heart chymase) inhibitors. However, these compounds are peptide compounds which are unsatisfactory in terms of oral absorption, and no pharmacological test data are available.

Patent applications filed by ZENECA Inc. (Japanese Patent Unexamined Publication Nos. 286946/1993, 56785/1994 and WO93/21210), J. Med. Chem. 1994, 37, p. 1259, J. Med. Chem. 1994, 37, p. 3090, J. Med. Chem. 1994, 37, p. 3303, J. Med. Chem. 1994, 37, p 3313, J. Med. Chem. 1995, 38, p 98, J. Med. Chem. 1995, 38, p 212 and others disclose or report heterocyclic compounds which are human leukocyte elastase inhibitors, and these compounds are known to selectively inhibit human leukocyte elastase.

Patent applications filed by ICI Americans Inc. (now ZENECA Inc.) (Japanese Patent Unexamined Publication Nos. 45395/1989), J. Am. Chem. Soc., 1992, 114, p 1854, J. Med. Chem. 1995, 38, p. 76, J. Med. Chem. 1995, 38, p. 3972 and others disclose or report peptide compound having heterocycle. These compounds are also known to selectively inhibit human leukocyte elastase.

It is therefore an object of the present invention to provide novel compounds having superior chymase inhibitory activity, pharmaceutical compositions thereof and chymase inhibitors.

DISCLOSURE OF THE INVENTION

The present inventors have conducted intensive studies in an attempt to achieve the above-mentioned objects, and found that, by modifying or converting a part of the structure of the compound disclosed by ZENECA Inc. and the like, compounds can be obtained that inhibit chymase group, inclusive of human heart chymase, with high selectivity, without inhibiting other enzymes such as human leukocyte elastase, which exhibit superior characteristics in absorption, safety and stability in blood, which resulted in the completion of the present invention.

Accordingly, the present invention realtes to a heterocyclic amide compound of the formula (I)

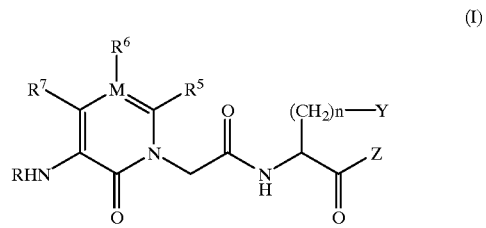

wherein

R is a hydrogen atom, alkyl, —CHO, —CONH$_2$, —COR$^1$, —COOR$^1$, —CONHOR$^1$, —CONHR$^1$, —CONR$^1$R$^{1'}$, —CONHSO$_2$R$^1$, —COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{1'}$ or —SO$_2$E wherein R$^1$ and R$^{1'}$ may be the same or different and each is independently alkyl, cycloalkyl, cycloalkylalkyl, aryl, arylalkyl, heteroaryl, heteroarylalkyl, heterocycle or heterocyclic alkyl, R$^2$, R$^3$ and R$^4$ may be the same or different and each is independently a hydrogen atom, alkyl or arylalkyl, or —NR$^3$R$^4$ may in combination form a heterocycle, X is a single bond, —NH—, —O— or —S—, W is a single bond, —NH—, —NHCO—, —NHCOO— or —NHCONH—, and E is a hydroxyl group or amino;

R$^5$, R$^6$ and R$^7$ may be the same or different and each is independently hydrogen atom or alkyl, or one of R$^5$, R$^6$ and R$^7$ is aryl, arylalkyl, arylalkenyl, heteroaryl, heteroarylalkyl or heteroarylalkenyl and the rest are hydrogen atom;

M is a carbon atom or nitrogen atom, provided that when M is a nitrogen atom, R$^6$ is void;

Y is cycloalkyl, aryl or heteroaryl;

Z is a group of the formula (i)

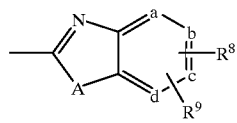

formula (ii)

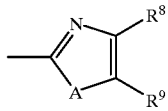

or formula (iii)

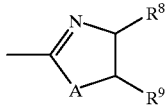

wherein $R^8$ and $R^9$ may be the same or different and each is independently hydrogen atom, alkyl, aryl, arylalkyl, heteroaryl, heteroarylalkyl, halogen, trifluoromethyl, cyano, nitro, $-NR^{10}R^{10'}$, $-NHSO_2R^{10}$, $-OR^{10}$, $-COOR^{10}$, $-CONHSO_2R^{10}$ or $-CONR^{10}R^{10'}$ wherein $R^{10}$ and $R^{10'}$ may be the same or different and each is independently hydrogen atom, alkyl, cycloalkyl, cycloalkylalkyl, aryl, arylalkyl, heteroaryl, heteroarylalkyl or trifluoromethyl, or $-NR^{10}R^{10'}$ may in combination form heterocycle, A is $-O-$, $-S-$ or $-NR^{12}-$ wherein $R^{12}$ is a hydrogen atom, alkyl, cycloalkyl or cycloalkylalkyl, and a, b, c and d are each a carbon atom or one of them is a nitrogen atom and the rest are carbon atom; and n is 0 or 1, wherein, of the above-mentioned groups, alkyl, cycloalkyl, cycloalkylalkyl, aryl, arylalkyl, arylalkenyl, heteroaryl, heteroarylalkyl, heteroarylalkenyl, heterocycle and heterocyclic alkyl each optionally has a substituent, (hereinafter to be also referred to as compound (I)) or a pharmacologically acceptable salt thereof.

The present invention also relates to the above-mentioned heterocyclic amide compound of the formula (I), wherein Y is an optionally substituted aryl, and a pharmacologically acceptable salt thereof; the above-mentioned heterocyclic amide compound of the formula (I), wherein Z is a group of the formula (i), and a pharmacologically acceptable salt thereof; and the above-mentioned heterocyclic amide compound of the formula (I), wherein one of $R^5$, $R^6$ and $R^7$ is optionally substituted aryl and the rest is hydrogen atom, provided that when M is a nitrogen atom, $R^6$ is void, and a pharmacologically acceptable salt thereof.

The present invention further relates to a compound of the formula (II)

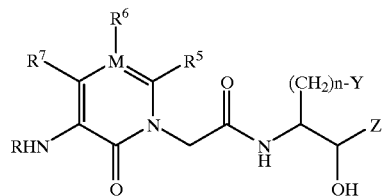

wherein each symbol is as defined above (hereinafter to be also referred to as compound (II)), which is useful for the synthesis of compound (I). In addition, the present invention relates to a compound of the formula (XXVI)

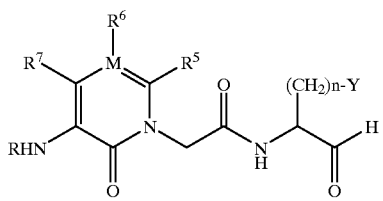

wherein each symbol is as defined above (hereinafter to be also referred to as compound (XXVI)), which is useful for the synthesis of compound (I) and which has superior chymase inhibitory activity, and a pharmacologically acceptable salt thereof.

The present invention moreover relates to a pharmaceutical composition containing compound (I), compound (XXVI) or a pharmacologically acceptable salt thereof, and a pharmacologically acceptable carrier, a pharmaceutical use thereof, particularly, to a chymase inhibitor.

The symbols used in the present specification are explained in the following.

Alkyl at R, $R^1$, $R^{1'}$, $R^2-R^{10}$, $R^{10'}$ and $R^{12}$ preferably has 1 to 6 carbon atoms and may be linear or branched. Examples thereof include methyl, ethyl, n-propyl, isopropyl, n-butyl, isobutyl, sec-butyl, tert-butyl, n-pentyl, isopentyl, n-hexyl and the like.

Cycloalkyl at $R^1$, $R^{1'}$, $R^{10}$, $R^{10'}$, $R^{12}$ and Y preferably has 3 to 7 carbon atoms and is exemplified by cyclopropyl, cyclobutyl, cyclopentyl, cyclohexyl, cycloheptyl and the like.

Cycloalkylalkyl at $R^1$, $R^{1'}$, $R^{10}$, $R^{10'}$ and $R^{12}$ has the same cycloalkyl moiety as mentioned above and the alkyl moiety which preferably has 1 to 3 carbon atoms and which may be linear or branched. Examples thereof include cyclopropylmethyl, 2-cyclobutylethyl, 3-cyclopentylpropyl, cyclohexylmethyl, 2-cyclohexylethyl, cycloheptylmethyl and the like.

Aryl at $R^1$, $R^{1'}$, $R^5-R^{10}$, $R^{10'}$ and Y is preferably phenyl, naphthyl or an ortho-fused bicyclic group having 8 to 10 cyclic atoms wherein at least one ring is an aromatic ring (e.g., indenyl and the like), and the like.

Arylalkyl at $R^1$, $R^{1'}$, $R^2-R^{10}$ and $R^{10'}$ has the same aryl moiety as mentioned above and the alkyl moiety which preferably has 1 to 3 carbon atoms and which may be linear or branched. Examples thereof include benzyl, phenethyl, 3-phenylpropyl, 1-naphthylmethyl, 2-naphthylmethyl, 2-(1-naphthyl)ethyl, 2-(2-naphthyl)ethyl, 3-(1-naphthyl)propyl, 3-(2-naphthyl)propyl and the like.

Arylalkenyl at $R^5-R^7$ has the same aryl moiety as mentioned above and the alkenyl moiety which preferably has 2 to 6 carbon atoms and which may be linear or branched. Examples thereof include styryl, 3-phenyl-2-propenyl, 4-phenyl-3-butenyl, 5-phenyl-4-pentenyl, 6-phenyl-5-hexenyl, 3-(1-naphthyl)-2-propenyl, 4-(2-naphthyl)-3-butenyl and the like.

Heteroaryl at $R^1$, $R^{1'}$, $R^5$–$R^{10}$, $R^{10'}$ and Y is preferably a 5 or 6-membered cyclic group having a carbon atom and 1 to 4 hetero atom(s) (oxygen atom, sulfur atom and nitrogen atom), an ortho-fused bicyclic hetero aryl having 8 to 10 cyclic atoms derived therefrom, which is particularly exemplified by benzo derivatives and derivatives obtained by fusing propenylene, trimethylene or tetramethylene therewith, a stable N-oxide thereof and the like. Examples thereof include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,2,4-thiadiazolyl, pyridyl, pyranyl, pyrazinyl, pyrimidinyl, pyridazinyl, 1,2,4-triazinyl, 1,2,3-triazinyl, 1,3,5-triazinyl, benzoxazolyl, benzothiazolyl, benzoimidazolyl, thianaphtenyl, isothianaphtenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl, benzoxazinyl and the like.

Heteroarylalkyl at $R^1$, $R^{1'}$, $R^5$–$R^{10}$ and $R^{10'}$ has the same heteroaryl moiety as mentioned above and the alkyl moiety which preferably has 1 to 3 carbon atoms and which may be linear or branched. Examples thereof include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyrinyl)ethyl, 3-(2-pyrrolyl)propyl and the like.

Heteroarylalkenyl at $R^5$–$R^7$ has the same heteroaryl moiety as mentioned above and the alkenyl moiety which preferably has 2 to 6 carbon atoms and which may be linear or branched. Examples thereof include 2-(2-pyridyl)ethenyl, 3-(2-pyridyl)-2-propenyl, 4-(3-pyridyl)-3-butenyl, 5-(2-pyrrolyl)-4-pentenyl, 6-(2-thienyl)-5-hexenyl and the like.

Heterocycle represented by $R^1$ and $R^{1'}$ is a 4 to 6-membered ring having a carbon atom and 1 to 4 hetero atom(s) (oxygen atom, sulfur atom and nitrogen atom). Examples thereof include azetidinyl, pyrrolidinyl, piperidinyl, piperidino, piperazinyl, morpholinyl, morpholino, thiomorpholinyl, oxothiomorpholinyl, dioxothiomorpholinyl, tetrahydropyranyl, dioxacyclohexyl and the like.

Heterocycle represented by —$NR^3R^4$ and —$NR^{10}R^{10'}$ is a 4 to 6-membered ring having a carbon atom, at least one nitrogen atom and optionally other hetero atom (oxygen atom or sulfur atom). Examples thereof include azetidinyl, pyrrolidinyl, piperidino, piperazinyl, morpholino, thiomorpholino, oxothiomorpholino, dioxothiomorpholino and the like.

Heterocyclic alkyl at $R^1$ and $R^{1'}$ has the same heterocyclic moiety as mentioned above for $R^1$ and $R^{1'}$, and linear or branched alkyl moiety preferably having 1 to 3 carbon atoms. Examples thereof include azetidinylethyl, pyrrolidinylpropyl, piperidinylmethyl, piperidinoethyl, piperazinylethyl, morpholinylpropyl, morpholinomethyl, thiomorpholinylethyl, oxothiomorpholinylethyl, dioxothiomorpholinylethyl, tetrahydropyranylpropyl, dioxacyclohexylmethyl and the like.

Halogen at $R^8$ and $R^9$ is exemplifeid by fluorine, chlorine, bromine and iodine.

Of the above-mentioned substituents, alkyl, cycloalkyl, cycloalkylalkyl, aryl, arylalkyl, arylalkenyl, heteroaryl, heteroarylalkyl, heteroarylalkenyl, heterocycle and heterocyclic alkyl are optionally substituted by one or ore substituents shown below.

The substituents for these substituents are exemplified by halogen, hydroxyl group, nitro, cyano, trifluoromethyl, alkyl, alkoxy, alkylthio, formyl, acyloxy, oxo, phenyl, arylalkyl, —COORa, —$CH_2$COORa, —$OCH_2$COORa, —CONRbRc, 13 $CH_2$CONRbRc, —$OCH_2$CONRbRc, —COO($CH_2$)$_2$NReRf, —$SO_2T^1$, —$CONRdSO_2T^1$, —NReRf, —NRgCHO, —NRgCOT$^2$, —NRgCOOT$^2$, —NRhCQNRiRj, —NRkSO$_2$T$^3$, —SO$_2$NRlRm, —SO$_2$NRnCOT$^4$ and the like.

Of the exemplified substituents for the above-mentioned substituents, halogen, alkyl and arylalkyl may be those mentioned above. Alkoxy preferably has 1 to 6 carbon atoms and may be linear or branched. Examples thereof include methoxy, ethoxy, propoxy, butoxy, pentyloxy, hexyloxy and the like. Alkylthio preferably has 1 to 6 carbon atoms and may be linear or branched. Examples thereof include methylthio, ethylthio, propylthio, butylthio, pentylthio, hexylthio and the like. Acyloxy preferably has 1 to 6 carbon atoms and may be linear or branched. Examples thereof include formyloxy, acetyloxy, propionyloxy, butyryloxy, valeryloxy, pivaloyloxy, hexanoyloxy and the like.

Ra–Rn show hydrogen atom, alkyl (same as above) or arylalkyl (same as above). —NRbRc, —NReRf, —NRiRj and —NRlRm in combination may form a heterocycle (same as those exemplifeid for the above-mentioned —$NR^3R^4$ and —$NR^{10}R^{10'}$, which is optionally substituted by the above-mentioned substituents). —NReRf can also show a heterocycle having =O (e.g., 2-pyrrolidinon-1-yl, succinimide, oxazolidin-2-on-3-yl, 2-benzoxazolinon-3-yl, phthalimide, cis-hexahydrophthalimide and the like). $T^1$–$T^4$ are the same as those exemplified above for $R^1$ and are optionally substituted by the above-mentioned substituents. Q is =O or =S.

The compound (I), compound (II) and compound (XXVI) can exist as optically active compounds or racemates due to the asymmetric carbon atom bound with —(CH$_2$)n—Y group. The racemates can b resolved into each optically active compound by a method known per se. When these compounds have additional asymmetric carbon atom, the compound can exist as a mixture of diastereomers or a single diastereomer, which can be also resolved into each optically active compound by a method known per se.

The compound (I), compound (II) and compound (XXVI) can show polymorphism and exist as two or more tautomers or solvates (e.g., ketone solvate, hydrate and the like).

Therefore, the present invention encompasses any of the above-mentioned stereoisomers, optical isomers, polymorphs, tautomers, solvates and optional mixtures thereof, and the like.

When the compound (I) and compound (XXVI) are acidic compounds, the pharmacologically acceptable salts thereof include, for example, alkali metal salt (e.g., salt with lithium, sodium, potassium and the like), alkaline earth metal salt (e.g., salt with calcium, magnesium and the like), aluminum salt, ammonium salt, salt with organic base (e.g., triethylamine, morpholine, piperidine, triethanolamine and the like) and the like.

When the compound (I) and compound (XXVI) are basic compounds, the pharmacologically acceptable salts thereof include inorganic acid addition salt (e.g., salt with hydrochloric acid, hydrobromic acid, hydriodic acid, sulfuric acid phosphoric acid and the like), organic acid addition salt (e.g., methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleinic acid, tartaric acid, succinic acid, mandelic acid, malic acid and the like), salt with amino acid (e.g., salt with glutamic acid, aspartic acid and the like) and the like.

The production method of the inventive compound (I) is shown in the following Scheme I

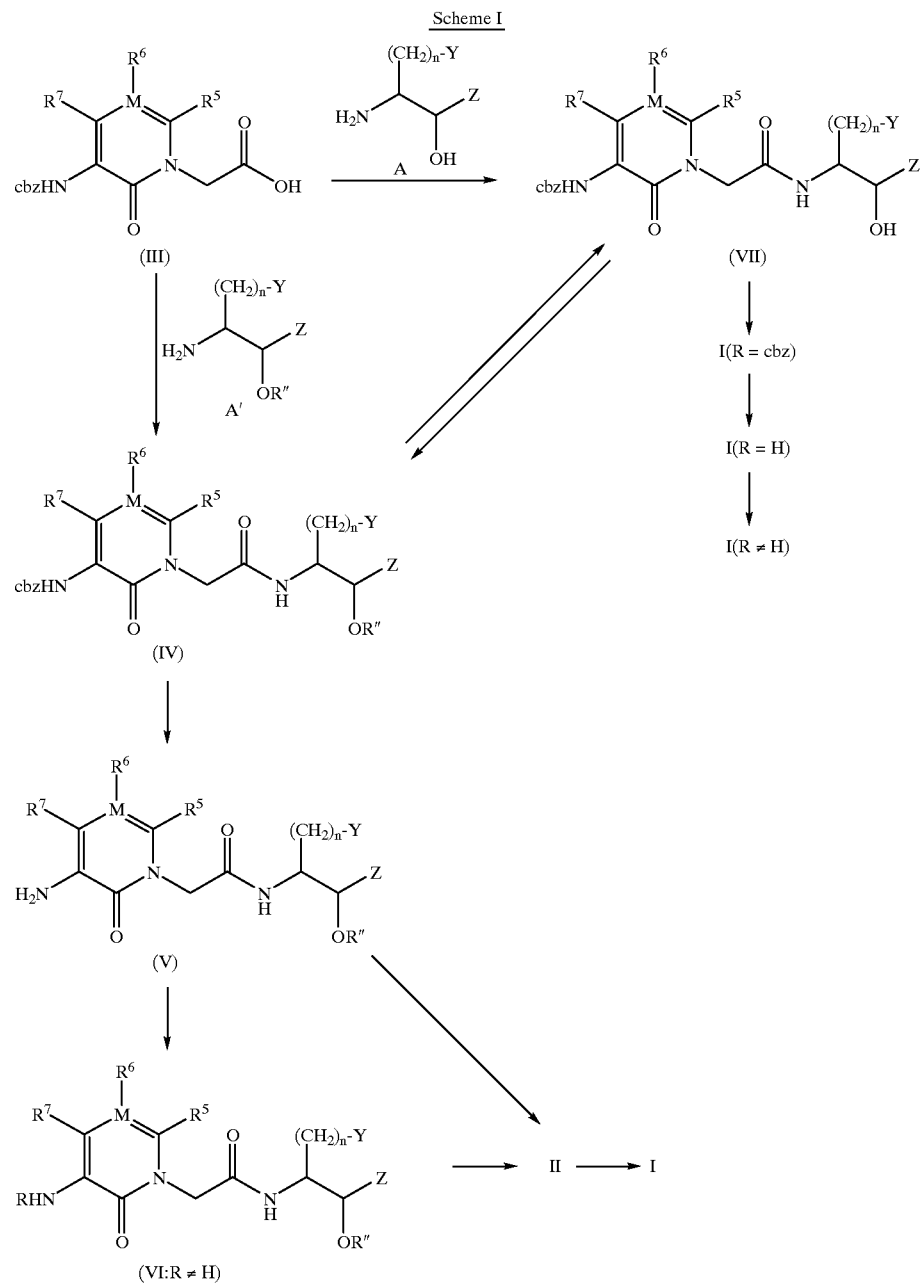

Of the compounds (I) of the present invention, preferred are a compound of the formula (I) wherein Y is optionally substituted aryl; compound of the formula (I) wherein Z is a group of the formula (i); a compound of the formula (I) wherein one of $R^5$, $R^6$ and $R^7$ is optionally substituted aryl and the rest are hydrogen atom, provided that when M is a nitrogen atom, $R^5$ is void, and the like.

More preferred are the compounds of the following Examples, 2, 4, 5, 8, 14, 15, 17, 19, 23, 26, 28, 30, 31, 32, 34, 36, 38, 40, 45, 46, 50, 52, 53, 54, 55, 56, 57, 58, 59, 60, 62, 64, 71, 72, 73, 74, 76, 78, 80, 82, 84, 86, 88, 90, 92, 93, 94 and the like.

wherein $R^{11}$ is a hydroxy-protecting group, cbz is benzyloxycarbonyl and other symbols are as defined above.

The hydroxy-protecting group at $R^{11}$ is, for example, acetyl, trimethylsilyl, tert-butyl dimethylsilyl, triisopropylsilyl, tert-butyl diphenylsilyl and the like.

As shown in the above scheme I, compound (III) is first condensed with amine A to give compound (VII), or compound (III) is first condensed with amine A' to give compound (IV).

The compound (III) is described in publications (Japanese Patent Unexamined Publication Nos. 56785/1994 and 286946/1993, Warner et al., J. Med. Chem. 1994, 37, p 3090, Damewood et al., J. Med. Chem. 1994, 37, p 3303, Veale et al., J. Med. Chem. 1995, 38, p 98, WO93/21210 and the like). It can be prepared by a conventional method based on these publications. The methods for prepareing amine A and amine A' are described later.

Preferably condensing agent used for this condensation to activate the carboxylic acid of compound (III) is exemplified by dicyclohexylcarbodiimide (DCC)/hydroxybenztriazole (HOBT), N-(3-dimethylaminopropyl)-N'-ethylcarbodiimide (WSCI) or hydrochloride thereof/HOBT, WSCI or hydrochloride thereof/4-dimethylaminopyridine (DMAP), 2-ethoxy-1-ethoxycarbonyl-1,2-dihydroquinoline (EEDQ), carbonyldiimidazol (CDI)/HOBT, diethylphosphoryl cyanide and the like.

This reaction is generally carried out in an inert solvent, wherein the inert solvent to be used may be any as long as it is aprotic. Preferred are acetonitrile, dichloromethane, chloroform, N,N-dimethylformamide and the like. This condensation is carried out at a temperature of −30–80° C., preferably 0–25° C.

The hydroxyl group of the obtained compound (VII) may be protected to give compound (IV). Conversely, the hydroxy-protecting group ($R^{11}$) of compound (IV) may be eliminated to give compound (VII).

The benzyloxycarbonyl group of compound (IV) can be removed by a conventional method such as hydrogenation decomposition and the like to convert the compound to compound (V).

The amino group bound to the carbon atom on the heterocyclic ring (pyridone ring or pyrimidone ring) of compound (V) can be acylated or sulfonylated by a conventional method to give compound (VI) wherein R is a substituent other than a hydrogen atom.

The compound (VI) wherein R is —CHO, —$CONH_2$, —$COR^1$, —$COOR^1$, —$CONHOR^1$, —$CONHR^1$, —$CONR^1R^{1'}$, —$CONHSO_2R^1$, —$COSR^1$, —$COCOR^2$, —$COCOOR^2$, —$CONHCOOR^2$ or —$COCONR^3R^4$ can be synthesized using an activated carboxylic derivative such as acid halide, or using carboxylic acid and a coupling agent, or other method.

When compound (VI) wherein R is —$CONH_2$, —$CONHR^1$, —$CONHSO_2R^1$ or —$CONHCOOR^2$ is synthesized, a method using isocyanate and the like can be used. For example, a method using carbonyldiimidazole, phosgene, diphosgen (trichloromethylchloroformate), triphosgene [bis(trichloromethyl)carbonate] and the like together with alcohol of the formula $R^1OH$, thiol of the formula $R^1SH$ or amine of the formula $R^1NH_2$, $(R^1)_2NH$, $R^1ONH_2$, and a base such as triethylamine and the like, is employed.

When a compound (VI) wherein R is —$CSXR^1$ is synthesized, a method using an activated thiocarboxylic derivative (e.g., thioylchloride, lower alkyl ester of dithioic acid and the like, and the like), a method using thioic acid and a coupling agent, and the like are employed. In addition, for example, a method using dimethyl trithiocarbonate and the like together with alcohol of the formula $R^1OH$, thiol of the formula $R^1SH$ or amine of the formula $R^1NH_2$ and the like, is employed. When a compound (VI) wherein X is —NH— is synthesized, a method using isothiocyanate and the like can be employed.

When a compound (VI) wherein R is —$SO_2WR^1$, —$SO_2NR^1R^{1'}$ or —$SO_2E$ is synthesized, the following method and the like is suitably used for sulfonylation. For example, a method using sulfonic acid of the formula HO—$SO_2WR^1$, HO—$SO_2NR^1R^{1'}$ or HO—$SO_2E$, or the corresponding halogenated acid, particularly sulfonyl (or sulfamoyl) chloride of the formula Cl—$SW_2WR^1$, Cl—$SO_2NR^1R^{1'}$ or Cl—$SO_2E$ and an organic base (e.g., triethylamine, pyridine and the like) or inorganic base (e.g., sodium carbonate, potassium carbonate and the like) in an inert solvent (e.g., dichloromethane, tetrahydrofuran, toluene and the like), can be employed.

When compound (VI) has a group of the formula —COORa (carboxyl) wherein Ra is hydrogen atom as the substituent for each substituent at R or Z, for example, the corresponding ester synthesized using an acid-protecting group that can be preferably removed [compound (VI) having —COORa wherein Ra is not hydrogen atom as the substituent for the substituent] is decomposed to give this compound. This decomposition is conducted by an optional method from various methods well known in organic chemistry, such as basic hydrolysis using, for example, lithium hydroxide, sodium hydroxide and the like, or hydrogenation decomposition of benzyl ester and the like.

When compound (VI) has a group of the formula —COORa, —CONRbRc, —COO$(CH_2)_2$NReRf or —CONRdSO$_2T^1$ as the substituent for each substituent at R or Z, for example, compound of the formula HORa, NHRbRc, HO$(CH_2)_2$NReRf or HNRdSO$_2T^1$ (Ra–Rf are not hydrogen atom) and compound (VI) having a group of the formula —COORa (carboxyl), wherein Ra is hydrogen atom, as the substituent of the substituent, or an activated derivative thereof, are reacted to give this compound.

When compound (VI) has a group of the formula —$OCH_2COORa$ or —$OCH_2CONRbRc$ as the substituent for each substituent at $R^5$–$R^7$, R or Z, for example, a compound of the formula BrCH$_2$COORa, ICH$_2$COORa, BrCH$_2$CONRbRc or ICH$_2$CONRbRc (Ra–Rc are not hydrogen atom) and compound (VI) having hydroxyl group as the substituent of the substituent, are reacted in the presence of a base such as sodium hydride and the like to give this compound.

When the compound (VI) has a group of the formula —NRgCOT$^2$, —NRgCOOT$^2$, —NRhCQNRiRj, —NRkSO$_2T^3$ or acyloxy as the substituent for each substituent at $R^5$–$R^7$, R or Z, for example, the corresponding compound (VI) having hydroxyl group, or amino group of the formula —NHRg, —NHRh or —NHRk as the substituent of the substituent is reacted with an activated derivative of an acid, which is represented by the formula HOCOT$^2$, HOCOOT$^2$, HOCQNRiRj, HOSO$_2T^3$ and the like, to give this compound.

When compound (VI) contains heteroaryl N-oxide in $R^5$–$R^7$, R or Z, the corresponding compound (VI) containing heteroaryl in the group at $R^5$–$R^7$, R or Z is oxidized with a conventional oxidizing agent such as dioxirane and the like in acetone to give this compound.

While conversion of the substituent of each at R, Z and the like, and the like has been explained by referring to the case of compound (VI), it does not mean that such conversion and the like are possible only with regard to compound (VI), but are possible with regard to various other compounds as long as it does not affect other functional groups contained in the chemical structure. For example, when the substituent of each substituent at R, Z and the like is amino, hydroxyl group and the like, conversion in the form of compound (I) rather than compound (VI) is preferable.

The hydroxy-protecting group ($R^{11}$) of compound (V) and compound (VI) is removed to give compound (II). This compound (II) is useful as the synthetic intermediate of compound (I).

This hydroxy-protecting group is removed in an inert solvent such as tetrahydrofuran and the like, using tetrabutyl ammonium fluoride and the like, wherein the sue of acid such as acetic acid and the like for buffering the reaction mixture is preferable.

Then, the hydroxyl group of compound (II) is oxidized to give compound (I).

The oxidation is preferably carried out, for example, by a method using an excess of dimethyl sulfoxide, water soluble carbodiimide and dichloroacetic acid as a catalyst in an inert solvent such as toluene and the like at approximately room temperature. Useful other methods include a method wherein an aqueous alkali solution of potassium permanganate is used; a method wherein oxalyl chloride, dimethyl sulfoxide and tertiary amine are used; a method wherein acetic anhydride and dimethyl sulfoxide are used; a method wherein pyridine-sulfur trioxide complex and dimethyl sulfoxide are used; a method wherein a chromium(VI) oxide—pyridine complex is used in methylene chloride; a method wherein a hypervalent iodine reagent such as periodinane (e.g., 1,1,1-triacetoxy-1,1-dihydro-1,2-benziodoxol-3(1H)-one and the like) is used in dichloromethane or dimethylformamide; and the like.

In the compound (VII) obtained by condensation of compound (III) and amine A or eliminating hydroxy-protecting group of compound (IV), the hydroxyl group is oxidized according to the above-mentioned method to give a compound (I) having amino protected by benzyloxycarbonyl.

Then, benzyloxycarbonyl of this compound is deprotected under mild reaction conditions to give compound (I) wherein R is hydrogen atom. For example, acid decomposition by reaction with trifluoromethanesulfonic acid or trifluoroacetic acid in the presence of anisole or thioanisole, or hydrogenation decomposition using palladium carbon and the like as a catalyst, is applied for deprotection.

When the above-mentioned acylation reaction and the like is additionally applied, compound (I) wherein R is other than hydrogen atom can be obtained.

Scheme II shows a different method for producing compound (IV). This method is applied solely when M is a carbon atom.

Scheme II

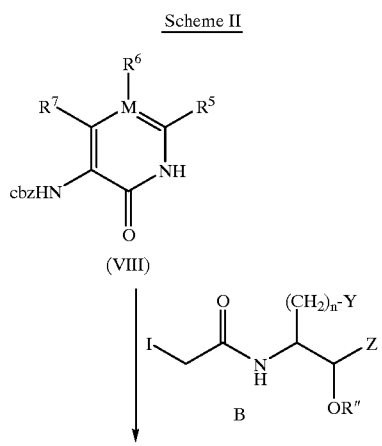

-continued

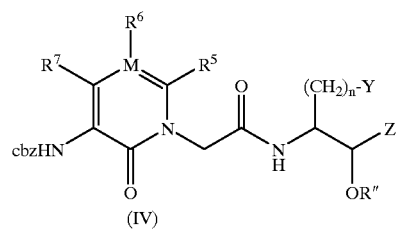

wherein each symbol is as defined above.

As shown in the above Scheme II, compound (IV) can be obtained by reacting compound (VIII) [compound disclosed in publication (see Japanese Patent Unexamined Publication No. 56785/1994, Warner et al., J. Med. Chem. 1994, 37, p 3090, Damewood et al., J. Med. Chem. 1994, 37, p 3303) or a compound obtained by a conventional method based on these publications] and compound B. The method for producing compound B is stated later.

As disclosed in, for example, Japanese Patent Unexamined Publication No. 56785/1994 and J. Med. Chem. 1994, 37, p 3303, this reaction is carried out by treating compound (VIII) with a base such as sodium hydride, potassium hydride and the like in an inert solvent such as aprotic solvent, particularly N,N-dimethylformamide, tetrahydrofuran and the like at −30–80° C., preferably 0–30° C., and reacting the obtained compound with compound B at −30–80° C., preferably 0–30° C. The thus obtained compound (IV) is introduced into compound (I) according to the method discussed under Scheme I.

Scheme III shows methods of synthesizing amine A and amine A' using cyanohydrin compound (XIII) as a key intermediate.

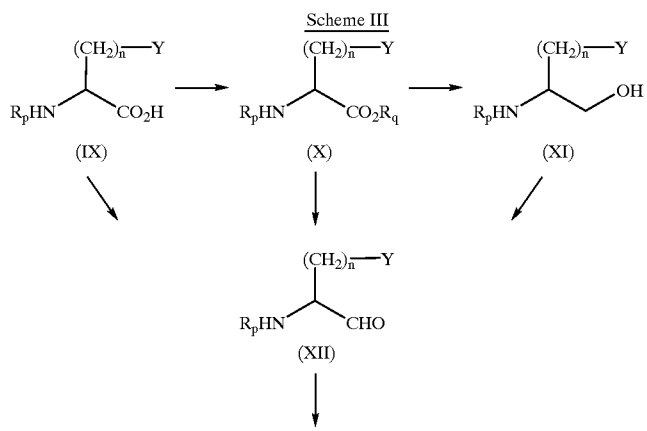

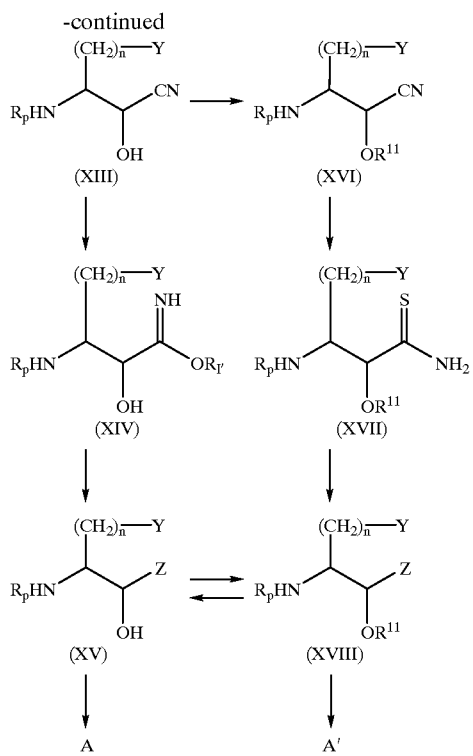

wherein Rp is amino-protecting group, Rq and Rr are each alkyl and other symbols are as defined above.

The amino-protecting group at Rp is exemplified by benzyloxycarbonyl (cbz), tert-butoxycarbonyl (BOC) and the like.

Alkyl at Rq and Rr has 1 to 6 carbon atoms and is exemplified by those mentioned above.

First, compound (IX) is esterified to give compound (X).

The esterification is carried out by reacting compound (IX) with alkyl halide corresponding to Rq in the presence of a base such as potassium hydrogencarbonate and the like, or reacting compound (IX) with diazoalkane, and the like.

While the α-amino acid, wherein amino group is protected, shown by the formula (IX), is mostly marketed, but those that are not can be synthesized by obtaining an amino acid from aldehyde Y—(CH$_2$)nCHO by a method for Strecker synthesis or other well known method and protecting amino group of the resultant amino acid.

Then, by reducing compound (X) using, for example, aluminum diisobutylhydride, compound (XII) can be obtained easily. Alternatively, as shown in the report of Fehrentz et al. (Snythesis, 1983, p 676), compound (IX) may be condensed with N,O-dimethylhydroxylamine to give amide derivative, and this derivative is reduced with lithium aluminum hydride to give compound (XII).

As a different method, compound (X) may be reduced with, for example, sodium borohydride/lithium chloride to give compound (XI), and compound (XI) is oxidized by the oxidation method discussed for conversion of compound (II) to compound (I) to ultimately give compound (XII).

Then, compound (XII) is treated with cyanide salt, preferably potassium cyanide or sodium cyanide, in the presence of auxiliary solvent such as tetrahydrofuran, ethyl acetate and dioxane, in an aqueous solution to give compound (XIII). Alternativelly, the compound (XII) may be treated with acetone cyanohydrin to give compound (XIII). It is also possible to obtain compound (XIII) by the use of trimethylsilyl cyanide. In this case, subsequent treatment with an acid removes trimethylsilyl.

When compound (XIII) is treated with hydrogen chloride in the presence of alcohol represented by Rr OH (e.g., methanol, ethanol, propanol, butanol and the like), hydrochloride salt of imidate compound (XIV) can be obtained. Generally, compound (XIV) is not isolated before proceeding to the next step, but the isolation is possible on demand. Method for synthesizing and handling imidate compound and the like are explained in the book of Patai ("The Chemistry of Amidines and Imidates", Wiley-Interscience, 1975) and publication of Nielson et al. (Chem. Rev. 1961, 61, p 1979).

Then, based on the report of Edwards et al. (J. Med. Chem. 1995, 38, p 76), Tsutsumi et al. (J. Med. Chem. 1994, 37, p 3492) or Costanzo et al. (J. Med. Chem. 1996, 39, p 3039), compound (XV) having a hetero ring represented by Z can be obtained from compound (XIV).

Amine A wherein Z is thiazole can be produced by a different method mentioned below using thioamide.

First, the hydroxyl group of compound (XIII) is protected by a hydroxy-protecting group ($R^{11}$) to give compound (XVI).

This compound (XVI) is treated with hydrogen sulfide by a conventional method in the presence of a basic catalyst (e.g., triethylamine and the like) as necessary to give compound (XVII).

Then, based on the report of Schmidt et al. (Snythesis, 1986, p 992) or Wiley et al. (Org. Reactions 1957, 6, p 367), compound (XVIII) wherein Z is thiazole can be obtained from compound (XVII).

The hydroxyl group of the compound (XV) obtained above may be protected with a hydroxy-protecting group ($R^{11}$) to convert the compound to compound (XVIII). Conversely, the hydroxy-protecting group ($R^{11}$) of compound (XVIII) may be eliminated to give compound (XV).

Lastly, the amino-protecting group of compound (XV) is removed to give amine A and the amino-protecting group of compound (XVIII) is removed to give amine A'.

Scheme IV shows methods of synthesizing amine A by reacting compound (XII) using heterocyclic reagent G—Z previously formed.

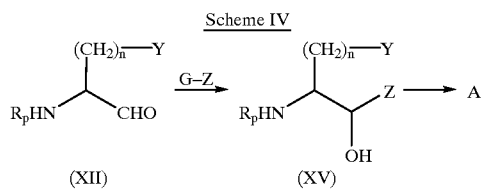

wherein G is a group imparting nucleophilicity to the 2-position carbon atom of the group represented by Z (e.g., lithium, trimethylsilyl and the like) and other symbols are as defined above.

As is shown in the report of Tsutsumi et al. (J. Med. Chem. 1994, 37, p 3492), the heterocyclic reagent G—Z, wherein G is lithium, is directly reacted with compound (XII) to give compound (XV).

The above-mentioned reagent G—Z, wherein G is lithium, can be produced and used as described in, for example, Wasserman et al. (Tetrahedron Lett. 1981, 22, p 1737), Schroeder et al. (Liebigs Ann. Chem. 1975, p 533), Beraud et al. (Bull. Soc. Chem. France 1962, p 2072), Shirlet et al. (J. Am. Chem. Soc. 1957, 79, p 4922), Ogura et al. (J. Org. Chem. 1974, 39, p 1374) or Jastin et al. (Chem. Ber. 1973, 106, p 594 and p 2815).

As shown in the report of Dondoni et al. (J. Org. Chem. 1988, 53, p 1748), Edwards et al. (J. Med Chem. 1995, 38, p 76), Tsutsumi et al. (J. Med. Chem. 1994, 37, p 3492) or Costanzo et al. (J. Med. Chem. 1996, 39, p 3039), the heterocyclic reagent G—Z, wherein G is trimethylsilyl, is first reacted with compound (XII) to introduce the compound into O-trimethylsilyl derivative of the corresponding alcohol.

Then, by a conventional method, trimethylsilyl is removed to give compound (XV). Preferably, the reaction proceeds in an inert solvent such as tetrahydrofuran, dichloromethane and the like in the presence or absence of cesium fluoride or tetrabutyl ammonium fluoride at 0–60° C.

As shown in the report of, for example, Dondi et al. (Tetrahedron Lett. 1985, 26, p 5477, J. Chem. Soc. Chem. Commun. 1984, p 258), Medici et al. (Tetrahedron Lett. 1983, 24, p 2901) for Edwards et al. (J. Med. Chem. 1995, 38, p 76), the above-mentioned reagent G—Z, wherein G is trimethylsilyl, can be produced and used in a manner similar to the case with 2-trimethylsilyloxazole, 2-trimethylsilylbenzothioazole and 2-trimethylsilylthiazole.

Then, the amino-protecting group of compound (XV) is removed to give amine A.

Scheme V shows methods of synthesizing amine A using compound (XIX) having N-methoxy-N-methylamido group and heterocyclic reagent G—Z via heterocyclic ketone.

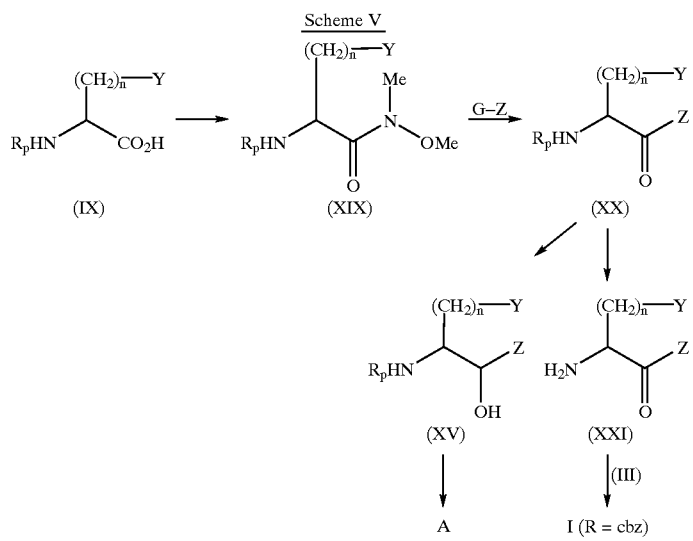

wherein each symbol is as defined above.

As shown in the report of Weinreb et al. (Tetrahedron Lett. 1981, 22, p 3815) and Dufore et al. (J. Chem. Soc. Perkin Trans. I 1986, p 1895), compound (IX) is condensed with N,O-dimethylhydroxylamine to give compound (XIX), and the compound is reacted with the heterocyclic reagent G—Z, wherein G is lithium, to give compound (XX). The heterocyclic reagent G—Z, wherein G is lithium, can be produced as mentioned above.

Then, compound (XX) is reduced with, for example, sodium borohydride and the like to give compound (XV) with ease and the amino-protecting group is removed to give amine A.

The compound (XXI) obtained by removing the amino-protecting group of compound (XX) is condensed with compound (III) by the method described with respect to the condensation using amine A under Scheme I to directly give compound (I) wherein R is benzyloxycarbonyl.

While amine A can be obtained as mentioned above, the hydroxyl group of amine A is protected with hydroxy-protecting group ($R^{11}$) to give amine A'. It is preferable that hydroxy-protecting group be introduced while amino is protected with protecting group Rp, and the amino-protecting group be removed thereafter.

Scheme VI shows methods of synthesizing compound B.

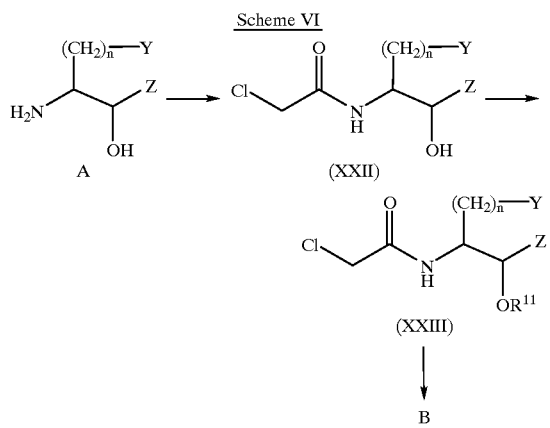

wherein each symbol is as defined above.

For example, as shown in the report of Damewood et al. (J. Med. Chem. 1994, 37, p 3303), amine A is first reacted with chloroacetyl chloride in an inert solvent such as tetrahydrofuran and the like in the presence of an organic base such as N-methylmorpholine and the like at −20–60° C., preferably 0–30° C., to give compound (XXII).

The hydroxyl group of this compound (XXII) is protected with the aforementioned protecting group ($R^{11}$), preferably silyl, such as tert-butyldimethylsilyl and the like, to give compound (XXIII).

Then, in an inert solvent such as acetone, compound (XXIII) is reacted with sodium iodide or potassium iodide at −20–60° C., preferably at 0–30° C., to give a desired compound B.

Scheme VII shows a different method of synthesizing compound (VII).

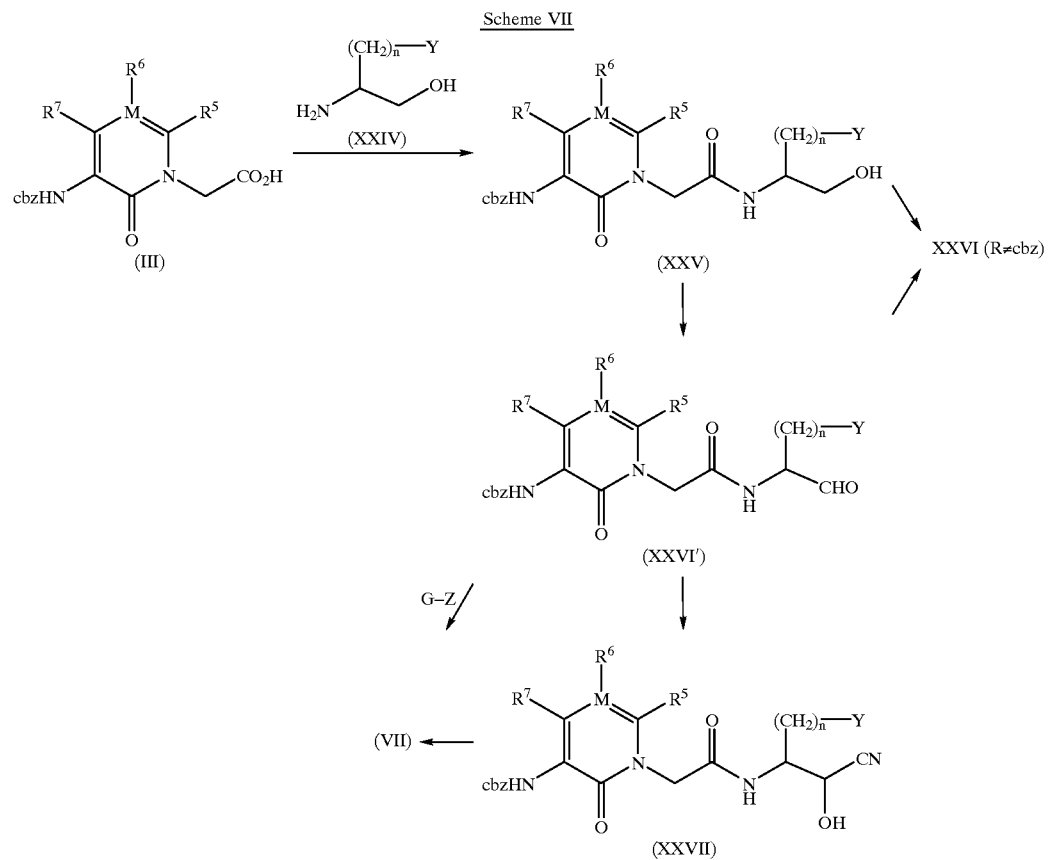

wherein each symbol is as defined above.

The compound (III) is condensed with compound (XXIV) by the method described with respect to the condensation with amine A under Scheme I to convert the compound to compound (XXV). This compound is oxidized by the method described with respect to the conversion of compound (II) to compound (I) to give compound (XXVI').

While the alcohol compound of the formula (XXIV) may be marketed, those that are not can be obtained by removing the amino-protecting group of compound (XI).

Then, compound (XXVI') is subjected to cyanohydrination reaction by the method described with respect to Scheme III, i.e., the method for conversion of compound (XII) to compound (XIII), to give compound (XXVII). After converting nitrile to imidate or thioamide, the heterocycle is formed by the aforementioned method to give compound (VII).

It is also possible to directly synthesize compound (VII) by the method described with respect to Scheme IV and using compound (XXVI').

The inventive compound (XXVI) is obtained as compound (XXVI') when R is benzyloxycarbonyl. When R is not benzyloxycarbonyl, it can be obtained from compound (XXV) or (XXVI').

The compound (XXVI) is derived from compound (XXV) by protecting the hydroxyl group of compound (XXV) with a protecting group ($R^{11}$) and following the method described with respect to the conversion of compound (IV) to compound (I) under Scheme I. When it is derived from compound (XXVI'), aldehyde group of compound (XXVI') is protected as acetal using methanol, ethylene glycol and the like, the compound is subjected to the method described with respect to the conversion of compound (IV) to compound (VI) under Scheme I, and acetal of the aldehyde group is deprotected.

Scheme VIII shows method of directly synthesizing compound (I) via compound (XXXI) having N-methoxy-N-methylamido group.

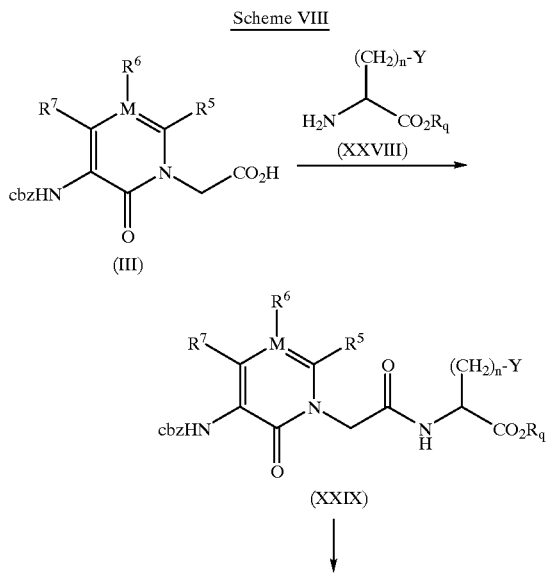

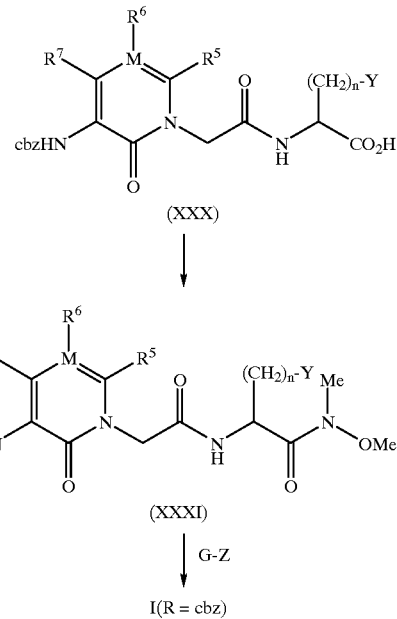

wherein each symbol is as defined above.

The compound (III) is condensed with compound (XXVIII) by the method described with respect to the condensation with amine A under Scheme I to convert the compound to compound (XXIX). Ester of this compound is hydrolyzed or subjected to suitable deprotection to give compound (XXX). Using this compound according to the method described under Scheme V, compound (I) wherein R is benzyloxycarbonyl via compound (XXXI) can be obtained.

While the ester of the formula (XXVIII) may be marketed, those that are not can be obtained by removing the amino-protecting group of compound (X).

The compound (I), compound (II) and compound (XXVI) of the present invention thus obtained can be subjected to known separation and purification methods, such as concentration, extraction, chromatography, reprecipitation, recrystallization and the like, to give a compound having an optional purity.

The pharmacologically acceptable salts of this compound (I) and compound (XXVI) can be produced by a known method. Further, various isomers of these compounds and the like can be produced by a known method.

The compound (I) and compound (XXVI) and pharmacologically acceptable salts thereof of the present invention have superior inhibitory action on chymase group in mammals such as human, dog, cat and the like.

Thus, the compound (I), compound (XXVI) and pharmacologically acceptable salts thereof of the present invention are useful as inhibitors of chymase group, inclusive of human heart chymase, and useful for the prophylaxis and treatment of various diseases caused by chymase, inclusive of the diseases considered to be caused by angiotensin II, such as hypertension, hypercardia, myocardial infarction, arteriosclerosis, diabetic and non-diabetic retinopathy, vascular restenosis after PTCA and the like. In addition, they show superior characteristics in absorption, safety, stability in blood and the like.

When the compound (I), compound (XXVI) and pharmacologically acceptable salts thereof of the present invention are used as pharmaceutical products, a pharmacologically acceptable carrier and the like are used to give a pharmaceutical composition in the form of granule, tablet, capsule, injection, ointment, cream, aerosol and the like, which is administered orally or parenterally. The above-mentioned preparation contains compound (I), compound (XXVI) or a pharmacologically acceptable salt thereof in an effective amount.

The dose of the compound (I), compound (XXVI) and a pharmacologically acceptable salt thereof varies depending on the administration route, condition, body weight, age and the like of patients, and is appropriately set according to the administration object. In general terms, for oral administration to an adult, the dose of 0.01–1000 mg/kg body weight/day, preferably 0.05–500 mg/kg body weight/day, which is given in a single dose or several doses a day.

The present invention is explained in detail in the following by way of Reference Examples and Examples, to which the present invention is not limited.

$^1$H-NMR was determined at 300 or 500 MHz. The chemical shift of $^1$H-NMR was based on tetramethylsilane (TMS) as an internal standard and relative delta (δ) value was shown in parts per million (ppm). The coupling constant was shown using s (singlet), d (doublet), t (triplet), q (quartet), m (multiplet), dd (doublet of doublet), brs (broad singlet), ABq (AB quartet) and the like, and obvious multiplicity by Hz. The thin layer chromatography (TLC) and column chromatography were performed using silica gel (Merck). Condensation was performed using a rotary evaporator manufactured by Tokyo Rikakikai Co., Ltd.

REFERENCE EXAMPLE 1

Synthesis of [5-benzyloxycarbonylamino-2-(4-fluorophenyl)-6-oxo-1,6-dihydro-1-pyrimidinyl] acetic acid (1) Into a solution of 4-fluorobenznitrile (50.9 g, 0.420 mol) in ethanol (500 mL) was blown hydrogen chloride to saturation under ice-cooling and the mixture was stirred at room temperature for 21 hours. The solvent was evaporated under reduced pressure and the obtained crystals were washed with ether and dried in vacuo to give ethyl 4-fluorobenzimidate hydrochloride as white crystals (78.8 g, 92%).

(2) To a solution of the objective compound (78.8 g, 0.387 mol) of Step (1) in ethanol (350 mL) was added dropwise aminoacetaldehyde diethyl acetal (62 mL, 0.43 mol) under ice-cooling, and the mixture was stirred at 5° C. for 16 hours. Eethanol was evaporated under reduced pressure and the obtained concentrate was added to 1 N aqueous sodium hydroxide solution (750 mL) and extracted with chloroform. The extract was dried over magnesium sulfate and the solvent was evaporated under reduced pressure to give a colorless oil containing N-(2,2-diethoxyethyl)-4-fluorobenzamidine.

(3) To a solution of the objective compound (crude product obtained by the above-mentioned reaction) of Step (2) in ethanol (150 mL) was added dropwise at room temperature diethylethoxymethylene malonate (86 mL, 0.43 mol). After the dropwise addition, the mixture was heated to 100° C. and stirred for 3 hours. The solvent was evaporated under reduced pressure and the obtained residue was separated and purified by silica gel column chromatography (1:1 ethyl acetate hexane) to give ethyl 1-(2,2-diethoxyethyl)-2-(4-fluorophenyl)pyrimidin-6(1H)-one-5-carboxylate as a pale-yellow oil (135 g) (yield from the objective compound of Step (1) 92%).

(4) To a solution of the objective compound (135 g, 0.358 mol) of Step (3) in pyridine (480 mL) was added lithium iodide (120 g, 0.895 mol) and the mixture was heated to 100° C. and stirred for 16 hours. The organic solvent was evaporated under reduced pressure and toluene (100 mL) was added. The residual trace amount of pyridine was evaporated under reduced pressure. The residue was added to a saturated aqueous sodium hydrogencarbonate solution (500 mL) and organic material other than carboxylic acid was extracted with ethyl acetate. After removing insoluble material by filtration, the aqueous layer was separated. The aqueous layer and the insoluble material were combined and 2 N hydrochloric acid (ca. 1 L) was added to adjust the pH to 3 and the mixture was extracted with ethyl acetate. The extract was washed with saturated brine and dried over magnesium sulfate. The solvent was evaporated under reduced pressure to give a brown oil containing 1-(2,2-diethoxyethyl)-2-(4-fluorophenyl)pyrimidin-6(1H)-one-5-carboxylic acid.

(5) To a solution of the objective compound (crude product obtained by the above-mentioned reaction) of Step (4) and triethylamine (87.5 mL, 0.63 mol) in 1,4-dioxane (900 mL) was added dropwise at room temperature diphenylphosphoryl azide (84 mL, 0.37 mol). After the dropwise addition, the mixture was heated to 110° C. and stirred for 2 hours. The mixture was cooled to room temperature and benzyl alcohol (44 mL, 0.43 mol) was added. The reaction mixture was heated again to 110° C. and the mixture was stirred for 4 hours. The reaction mixture was cooled to room temperature and 1,4-dioxane was evaporated under reduced pressure. The residue was added to a saturated aqueous ammonium chloride solution (1 L) and extracted with ethyl acetate. The extract was washed successively with 1 N aqueous sodium hydroxide solution and saturated brine, dried over magnesium sulfate and concentrated under reduced pressure. The residue was separated by silica gel column chromatography (1:2 ethyl acetate:hexane) to give a mixture of [5-benzyloxycarbonylamino-2-(4-fluorophenyl)-1,6-dihydro-6-oxo-1-pyrimidinyl]acetaldehyde diethyl acetal and benzyl alcohol as a pale-yellow oil (126 g) (69% as objective compound).

(6) To a solution of objective compound of Step (5) (126 g, mixture with benzyl alcohol, 0.247 mol as objective compound of Step (5)) in tetrahydrofuran (THF) (650 mL) was added 1 N hydrochloric acid (500 mL) and the mixture was stirred at 70° C. for 14 hours. The reaction mixture was cooled to room temperature and THF was evaporated under reduce pressure. To the obtained concentrate was added a saturated aqueous sodium hydrogencarbonate solution to adjust its pH to 7 and the mixture was extracted with ethyl acetate. The extract was dried over magnesium sulfate and the solvent was evaporated under reduced pressure to give a white solid containing [5-benzyloxycarbonylamino-2-(4-fluorophenyl)-1,6-dihydro-6-oxo-1-pyrimidinyl] acetaldehyde.

(7) To a mixture of the objective compound (crude product obtained by the above-mentioned reaction) of Step (6), 2-methyl-2-propanol (900 mL) and 2-methyl-2-butene (106 mL, 1.00 mol) was added a solution of sodium dihydrogenphosphate dihydrate (180 g, 1.15 mol) and sodium chlorite (80% content, 136 g, 1.20 mol) in water (400 mL) and the mixture was stirred at room temperature for 2 hours. The insoluble material was removed by filtration and the organic solvent was evaporated under reduced pressure. The obtained concentrate was added to 2 N hydrochloric acid (650 mL) and the mixture was extracted with ethyl acetate. The extract was washed with saturated brine, dried over magnesium sulfate and concentrated under reduced pressure. Ethyl acetate-hexane (1:1) was added to the residue for crystallization to give the title compound as a white solid (10.6 g). The insoluble material obtained earlier was added to 1 N hydrochloric acid (500 mL) and the mixture was extracted with ethyl acetate. The extract was washed with saturated brine and dried over magnesium sulfate. The solvent was evaporated under reduced pressure to give the title compound as a white solid (67.7 g, total yield 80%).

$^1$H-NMR (500 MHz, DMSO-$d_6$)δ 13.3 (brs, 1H), 8.99 (s, 1H), 8.46 (s, 1H), 7.56 (dd, J=5.4, 8.9 Hz, 2H), 7.44 (d, J=7.2 Hz, 2H), 7.30–7.42 (m, 5H), 5.19 (s, 2H), 4.53 (s, 2H)

IR (KBr) 3650–2300, 1720, 1660, 1600 cm$^{-1}$

REFERENCE EXAMPLE 2

Synthesis of 2-amino-1-(2-benzoxazolyl)-1-hydroxy-3-phenylpropane (1) To a mixture of L-phenylalaninol (20.2 g, 0.134 mol), sodium carbonate (21.1 g, 0.200 mol) and 1,4-dioxane (150 mL) was added a solution of benzyloxycarbonyl chloride (19.1 mL, 0.134 mol) in 1,4-dioxane (50 mL) and the mixture was stirred at room temperature for 3 hours. Water (300 mL) was added to the reaction mixture and the obtained mixture was added to ice-cooled 0.5 N hydrochloric acid (500 mL). The precipitated crystals were collected by filtration and washed with hexane and dried to give N-benzyloxycarbonyl-L-phenylalaninol as white crystals (28.8 g, 76%).

(2) To a solution of the objective compound (10.7 g, 37.5 mmol) of Step (1) and triethylamine (21.3 mL, 153 mmol) in dichloromethane (100 mL) was added a solution of sulfur trioxide-pyridine complex (23.9 g, 150 mmol) in dimethyl sulfoxide (DMSO) (100 mL) at –10° C. The obtained solution was stirred at 10–20° C. for 45 min and added to the saturated brine (400 mL). The mixture was extracted with ether. The extract was washed successively with 1 N hydrochloric acid, a saturated aqueous sodium hydrogencarbonate solution and saturated brine, dried over magnesium sulfate and concentrated under reduced pressure to give N-benzyloxycarbonyl-L-phenylalaninal as a white solid (0.6 g, quantitatively).

(3) To a solution of the objective compound (5.00 g, 17.6 mmol) of Step (2) and acetone cyanohydrin (4.8 mL, 53 mmol) in dichloromethane (50 mL) was added triethylamine (1.5 mL, 11 mmol) and the mixture was stirred at room temperature for 4 hours. The solvent was evaporated under reduced pressure and the obtained concentrate was added to water (100 mL). The mixture was extracted with ethyl acetate. The extract was washed with saturated brine, dried over magnesium sulfate and concentrated under reduced pressure. The residue was separated and purified by silica gel column chromatography (2:1 hexane:ethyl acetate) to give N-benzyloxycarbonyl-DL-phenylaraninal cyanohydrin as a pale-yellow solid (5.15 g, 94%).

(4) To a mixture of chloroform (30 mL) and ethanol (28 mL, 0.48 mol) was added dropwise acetyl chloride (31 mL, 0.44 mol) under ice-cooling over 20 min. The mixture was stirred at 0° C. for 10 min and a solution of the objective compound (4.50 g, 14.5 mmol) of Step (3) in chloroform (30 mL) was added. The mixture was stirred at 0° C. for 3 hours. The solvent was evaporated under reduced pressure to give a pale-yellow solid. Thereto were added ethanol (100 mL) and o-aminophenol (1.90 g, 17.4 mmol) and the mixturre was heated to 90° C. and stirred for 6 hours. The solvent was evaporated under reduced pressure and the obtained concentrate was added to 0.5 N aqueous sodium hydroxide solution (100 mL) and the mixture was extracted with ethyl acetate. The extract was washed successively with 0.5 N hydrochloric acid, a saturated aqueous sodium hydrogencarbonate solution and saturated brine, dried over magnesium sulfate and concentrated under reduced pressure. The residue was separated and purified by silica gel column chromatography (60:1 chloroform:methanol) to give 1-(2-benzoxazolyl)-2-benzyloxycarbonylamino-1-hydroxy-3-phenylpropane as a pale-brown solid (5.12 g, 88%).

(5) To a solution of the objective compound (3.63 g, 9.02 mmol) of Step (4) in methanol (50 mL) was added under nitrogen atmosphere 10% palladium carbon (480 mg) and the mixture was stirred at room temperature for 18 hours under hydrogen atmosphere. The catalyst was filtered off and washed with methanol. The filtrate was concentrated under reduced pressure to give the title compound as a brown solid (2.43 g, 100%).

$^1$H-NMR (500 MHz, DMSO-$d_6$)δ 7.74–7.68 (m, 2H), 7.41–7.15 (m, 7H), 6.17 (m, 0.3H), 6.08 (brs, 0.7H), 4.61 (m, 0.7H), 4.54 (m, 0.3H), 3.34 (m, 1H), 3.05 (dd, J=13.4, 3.8 Hz, 0.3H), 2.78 (dd, J=13.4, 5.9 Hz, 0.7H), 2.60 (dd, J=13.4, 7.9 Hz, 0.7H), 2.53 (dd, J=13.4, 8.9 Hz, 0.3H), 1.47 (brs, 2H)

IR (KBr) 3400, 3020, 1585, 1555 cm$^{-1}$

REFERENCE EXAMPLE 3

Synthesis of 2-amino-1-hydroxy-1-[5-(methoxycarbonyl)benzoxazol-2-yl]-3-phenylpropane (1) To a solution of 4-hydroxy-3-nitrobenzoic acid (15.8 g, 86.3 mmol) in 1,2-dichloroethane (150 mL) were added methanol (14 mL) and conc. sulfuric acid (0.5 mL) and the mixture was heated to 80° C. and stirred. Methanol (9 mL) was added on the way and the mixture was stirred for 21 hours. The reaction mixture was added to a saturated aqueous sodium hydrogencarbonate solution (400 mL) and extracted with chloroform. The extract was washed with saturated brine, dried over magnesium sulfate and concentrated under reduced pressure to give methyl 4-hydroxy-3-nitrobenzoate as a yellow solid (11.5 g, 68%).

(2) To a solution of the objective compound (11.4 g, 57.8 mmol) of Step (1) in ethyl acetate (300 mL) was added under nitrogen atmosphere 10% palladium carbon (1.80 g) and the mixture was stirred at room temperature for 18 hours under hydrogen atmosphere. The catalyst was filtered off and washed with ethyl acetate. The filtrate was concentrated under reduced pressure. The obtained solid was washed with ether-hexane (1:1) and dried in vacuo to give methyl 3-amino-4-hydroxybenzoate as a pale-brown solid (9.34 g, 97%).

(3) Using the objective compound of Step (2) and by a reaction similar to that in Reference Example 2-(4), 2-benzyloxycarbonylamino-1-hydroxy-1-[5-(methoxycarbonyl)benzoxazol-2-yl]-3-phenylpropane was obtained as a pale-brown solid (1.80 g, 81%).

(4) Using the objective compound of Step (3) and by a reaction similar to that in Reference Example 2-(5), the title compound was obtained as a pale-brown solid (1.14 g, 98%).

$^1$H-NMR (500 MHz, DMSO-$d_6$)δ 8.27 (d, J=1.3 Hz, 0.4H), 8.25 (d, J=1.3 Hz, 0.6H), 8.03 (dd, J=8.6, 1.3 Hz, 0.4H), 8.02 (dd, J=8.6, 1.3 Hz, 0.6H), 7.84 (d, J=8.6 Hz, 0.4H), 7.81 (d, J=8.6 Hz, 0.6H), 7.28–7.23 (m, 4H), 7.18–7.13 (m, 1H), 4.77–4.73 (m, 1H), 3.89 (s, 3H), 3.58 (m, 0.6H), 3.50 (m, 0.4H), 3.06 (dd, J=13.6, 4.8 Hz, 0.4H), 2.88 (dd, J=13.6, 7.3 Hz, 0.6H), 2.81 (dd, J=13.6, 6.8 Hz, 0.6H), 2.65 (dd, J=13.6, 8.2 Hz, 0.4H),

IR (KBr) 3300, 1710, 1615 cm$^{-1}$

REFERENCE EXAMPLE 4

Synthesis of 2-amino-1-hydroxy-1-[6-(methoxycarbonyl)benzoxazol-2-yl]-3-phenylpropane (1) Using 3-hydroxy-4-nitrobenzoic acid and by a reaction similar to that in Reference Example 3-(1), methyl 3-hydroxy-4-nitrobenzoate was obtained as a yellow solid (13.8 g, 85%).

(2) Using the objective compound of Step (1) and by a reaction similar to that in Reference Example 3-(2), methyl 4-amino-3-hydroxybenzoate was obtained as a white solid (11.0 g, 95%).

(3) Using the objective comound of Step (2) and by a reaction similar to that in Reference Example 2-(4), 2-benzyloxycarbonylamino-1-hydroxy-1-[6-(methoxycarbonyl)benzoxazol-2-yl]-3-phenylpropane as a brown solid (4.02 g, 68%).

(4) Using the objective compound of Step (3) and by a reaction similar to that in Reference Example 2-(5), the title compound was obtained as a pale-brown solid (688 mg, 83%).

$^1$H-NMR (500 MHz, DMSO-$d_6$)δ 8.25 (d, J=1.0 Hz, 0.4H), 8.23 (d, J=1.0 Hz, 0.6H), 8.03–7.97 (m, 1H), 7.85 (d, J=8.4 Hz, 0.4H), 7.83 (d, J=8.3 Hz, 0.6H), 7.31–7.14 (m, 5H), 6.26 (d, J=5.9 Hz, 0.4H), 6.15 (brs, 0.6H), 4.66 (m, 0.6H), 4.58 (m, 0.4H), 3.89 (s, 3H), 3.35 (m, 1H), 3.05 (dd, J=13.5, 3.8 Hz, 0.4H), 2.80 (dd, J=13.4, 6.1 Hz, 0.6H), 2.62 (dd, J=13.4, 7.7 Hz, 0.6H), 2.54 (dd, J=13.5, 8.8 Hz, 0.4H), 1.52 (brs, 2H)

IR (KBr) 3330, 1705, 1600 cm$^{-1}$

REFERENCE EXAMPLE 5

Synthesis of Benzyl 3-amino-4-hydroxybenzoate (1) Using 4-hydroxy-3-nitrobenzoic acid and benzyl alcohol and by a reaction similar to that in Reference Example 3-(1), a mixture of benzyl 4-hydroxy-3-nitrobenzoate and benzyl alcohol was obtained as a yellow oil (9.01 g).

(2) To a solution of the objective compound (mixture with benzyl alcohol, 9.01 g) of Step (1) in a mixture of THF (130 mL) and water (50 mL) were added iron powder (9.15 g, 164 mmol) and 1 N hydrochloric acid (7 mL) and the mixture was stirred at room temperature for 2.5 hours. The insoluble material was filtered off through celite and washed with methanol. The filtrate and washing solution were combined and the organic solvent was evaporated under reduced pressure. The concentrate was added to a saturated aqueous sodium hydrogencarbonate solutin (150 mL) and the mixture was extracted with ethyl acetate. The extract was washed with saturated brine, dried over magnesium sulfate and concentrated under reduced pressure. The residue was separated and purified by silica gel column chromatography (1:1 hexane:ethyl acetate) to give the title compound as a pale-brown solid (3.02 g) (yield from 4-hydroxy-3-nitrobenzoic acid, 45%).

$^1$H-NMR (500 MHz, DMSO-$d_6$)δ 9.8 (brs, 1H), 7.44–7.37 (m, 4H), 7.34 (t, J=6.9 Hz, 1H), 7.27 (d, J=2.0 Hz, 1H), 7.14 (dd, J=8.2, 2.0 Hz, 1H), 6.72 (d, J=8.2 Hz, 1H), 5.25 (s, 2H), 4.8 (brs, 2H), IR (KBr) 3250, 1665, 1585, 1510 cm$^{-1}$

REFERENCE EXAMPLE 6

Synthesis of 2-amino-1-hydroxy-1-(5-nitrobenzoxazol-2-yl)-3-phenylpropane (1) Using 2-amino-4-nitrophenol and by a reaction similar to that in Reference Example 2-(4), 2-benzyloxycarbonylamino-1-hydroxy-1-(5-nitrobenzoxazol-2-yl)-3-phenylpropane was obtained as a brown solid (2.77 g, 35%).

(2) To a solution of the objective compound (2.01 g, 4.50 mmol) of Step (1) and anisole (1.60 mL, 14.7 mmol) in dichloromethane (50 mL) was added under ice-cooling trifluoromethanesulfonic acid (2.39 mL, 27.0 mmol) and the mixture was stirred at 0° C. to room temperature for 1.5 hours. A saturated aqueous sodium hydrogencarbonate solution (45 mL) was added under ice-cooling and the mixture was stirred for 15 min and the mixture was extracted with ethyl acetate. The extract was washed with saturated brine, dried over magnesium sulfate and concentrated under reduced pressure. The residue was separated and purified by silica gel column chromatography (93:7 dichloromethane:methanol) to give the title compound as a yellow solid (1.19 g, 85%).

$^1$H-NMR (300 MHz, DMSO-$d_6$)δ 8.60 (d, J=2.3 Hz, 1H), 8.31 (dd, J=8.9, 2.3 Hz, 1H), 7.96 (d, J=8.9 Hz, 1H), 7.30–7.12 (m, 5H), 6.23 (brs, 1H), 4.68 (brs, 1H), 3.33 (m, 1H), 2.82 (dd, J=13.3, 6.4 Hz, 1H), 2.64 (dd, J=13.3, 7.6 Hz, 1H), 1.59 (brs, 2H)

IR (KBr) 3325, 3050, 2940, 1620, 1570, 1520 cm$^{-1}$

REFERENCE EXAMPLE 7

Synthesis of 2-amino-1-hydroxy-1-(5-methoxybenzoxazol-2-yl)-3-phenylpropane (1) Using 2-amino-4-methoxyphenol and by a reaction similar to that in Reference Example 2-(4), 2-benzyloxycarbonylamino-1-hydroxy-1-(5-methoxybenzoxazol-2-yl)-3-phenylpropane was obtained as a dark brown solid (3.09 g, 85%).

(2) Using the above-mentioned compound and by a reaction similar to that in Reference Example 2-(5), the title compound was obtained as a brown solid (1.92 g, 92%).

$^1$H-NMR (500 MHz, DMSO-$d_6$) δ7.60 (d, J=8.8 Hz, 0.4H), 7.59 (d, J=8.8 Hz, 0.6H), 7.32–7.15 (m, 6H), 6.98–6.93 (m, 1H), 6.14 (d, J=5.6 Hz, 0.4H), 6.05 (brs, 0.6H), 4.56 (m, 0.6H), 4.51 (m, 0.4H), 3.80 (s, 3H), 3.3 (m, 1H), 3.02 (dd, J=13.4, 3.7 Hz, 0.4H), 2.75 (dd, J=13.4, 5.0 Hz, 0.6H), 2.57 (dd, J=13.4, 8.0 Hz, 0.6H), 2.51 (m, 0.4H), 1.46 (brs, 2H)

IR (KBr) 3320, 3000, 2900, 2810, 2630, 1600, 1555 cm$^{-1}$

REFERENCE EXAMPLE 8

Synthesis of 2-amino-1-hydroxy-1-(2-oxazolinyl)-3-phenylpropane (1) To a mixture of chloroform (9 mL) and ethanol (8.3 mL, 0.14 mol) was added dropwise acetyl chloride (9.1 mL, 0.13 mol) over 20 minutes under ice-cooling. The mixture was stirred at 0° C. for 10 min and a solution of the objective compound (1.33 g, 4.29 mmol) of Reference Example 2-(3) in chloroform (9 mL) was added. The mixture was stirred at 0° C. for 3 hours and the solvent was evaporated under reduced pressure to give a pale-brown solid. Thereto were added dichloromethane (18 mL), monoethanolamine (0.51 mL, 8.5 mmol) and triethylamine (1.2 mL, 8.6 mmol), and the mixture was stirred at room temperature for 18 hours. The reaction mixture was added to 1 N aqueous sodium hydroxide solution (50 mL) and the mixture was extracted with ethyl acetate. The extract was washed with saturated brine, dried over magnesium sulfate and concentrated under reduced pressure. The residue was separated and purified by silica gel column chromatography (30:1 chloroform:methanol) to give 2-benzyloxycarbonylamino-1-hydroxy-1-(2-oxazolinyl)-3-phenylpropane as a white solid (509 mg, 33%).

(2) Using the above-mentioned compound and by a reaction similar to that in Reference Example 2-(5), the title compound was obtained as a white solid (284 mg, 91%).

$^1$H-NMR (300 MHz, DMSO-$d_6$) δ7.33–7.12 (m, 5H), 4.20 (m, 2H), 3.90(dd, J=8.4, 4.6 Hz, 1H), 3.72 (m, 2H), 3.04 (m, 1H), 2.90 (dd, J=13.4, 4.1 Hz, 0.4H), 2.80–2.65 (m, 1.2H), 2.42 (dd, J=13.4, 8.8 Hz, 0.4H)

EXAMPLE 1

Synthesis of 2-[5-benzyloxycarbonylamino-2-(4-fluorophenyl)-6-oxo-1,6-dihydro-1-pyrimidinyl]-N-[1-[(2-benzoxazolyl)carbonyl]-2-phenylethyl]acetamide (1) To a solution of the title compound (1.90 g, 4.48 mmol) of Reference Example 1 and the title compound (1.37 g, 5.11 mmol) of Refernce Example 2 in DMF (15 mL) were added HOBT (1.21 g, 8.95 mmol) and WSCI hydrochloride (1.03 g, 5.37 mmol) and the mixture was stirred at room temperature for 4 hours. The reaction mixture was added to 0.5 N hydrochloric acid (100 mL) and the mixture was extracted with ethyl acetate. The extract was washed successively with a saturated aqueous sodium hydrogencarbonate solution and saturated brine, dried over magnesium sulfate and concentrated under reduced pressure. The obtained solid was washed with ether, and dried in vacuo to give 2-[5-benzyloxycarbonylamino-2-(4-fluorophenyl)-6-oxo-1,6-dihydro-1-pyrimidinyl]-N-[1-[(2-benzoxazolyl)hydroxymethyl]-2-phenylethyl]acetamide as a white solid (2.43 g, 84%).

(2) To a solution of the objective compound (2.12 g, 3.27 mmol) of Step (1) in a mixture of DMSO (20 mL) and toluene (20 mL) were added WSCI hydrochloride (3.13 g, 16.3 mmol) and dichloroacetic acid (0.54 mL, 6.5 mmol) and the mixture was stirred at room temperature for 3.5 hours. The reaction mixture was added to 1 N hydrochloric acid (100 mL) and extracted with ethyl acetate. The extract was washed with a saturated aqueous sodium hydrogencarbonate solution and the precipitated white solid was collected by filtration. The filtrate was further washed with saturated brine, dried over magnesium sulfate and concentrated under reduced pressure. The residue and the precipitate collected earlier were combined and separated and purified by silica gel column chromatography (5:1 dichloromethane:ethyl acetate) to give the title compound as white crystals (1.69 g, 80%). The crystals were recrystallized from ethyl acetate to give white crystals (1.43 g).

mp 222–225° C.

$^1$H-NMR (500 MHz, DMSO-$d_6$) δ 8.98 (d, J=6.9 Hz, 1H), 8.86 (s, 1H), 8.40 (s, 1H), 8.00 (d, J=8.0 Hz, 1H), 7.91 (d, J=8.0 Hz, 1H), 7.66 (t, J=8.0 Hz, 1H), 7.55 (t, J=8.0 Hz, 1H), 7.46–7.40 (m, 4H), 7.38 (t, J=7.1 Hz, 2H), 7.33 (t, J=7.1 Hz, 1H), 7.25 (t, J=6.7 Hz, 2H), 7.22–7.13 (m, 5H), 5.56 (m, 1H), 5.17 (s, 2H), 4.53 (d, J=16.6 Hz, 1H), 4.45 (d, J=16.6 Hz, 1H), 3.31 (dd, J=14.2, 4.8 Hz, 1H), 2.96 (dd, J=14.2, 9.0 Hz, 1H)

IR (KBr) 3360, 3270, 3040, 1705, 1655, 1600, 1520 cm$^{-1}$

MS (SIMS, positive) m/z 646 (MH$^+$)

EXAMPLE 2

Synthesis of 2-[5-amino-2-(4-fluorophenyl)-6-oxo-1,6-dihydro-1-pyrimidinyl]-N-[1-[(2-benzoxazolyl)carbonyl]-2-phenylethyl]acetamide To a solution of the title compound (1.14 g, 1.77 mmol) of Example 1 in a mixture of methanol (15 mL) and THF (25 mL) was added 10% palladium carbon (188 mg) under a nitrogen atmosphere and the mixture was stirred at room temperature for 4 hours under a hydrogen atmosphere. The catalyst was removed by filtration and washed with chloroform-methanol (10:1) and the filtrate was concentrated under reduced pressure. The residue was separated and purified by silica gel column chromatography (50:1 chloroform:methanol) to give the title compound as white crystals (704 mg, 78%).

mp 233–236° C.

$^1$H-NMR (500 MHz, DMSO-$d_6$)δ 8.92 (d, J=6.8 Hz, 1H), 8.01 (d, J=8.0 Hz, 1H), 7.91 (d, J=8.0 Hz, 1H), 7.66 (t, J=8.0 Hz, 1H), 7.56 (t, J=8.0 Hz, 1H), 7.35 (dd, J=8.6, 5.5 Hz, 2H), 7.28 (s, 1H), 7.26 (t, J=8.0 Hz, 2H), 7.23–7.17 (m, 3H), 7.09 (t, J=8.0 Hz, 2H), 5.55 (m, 1H), 5.13 (s, 2H), 4.48 (d, J=16.7 Hz, 1H), 4.44 (d, J=16.7 Hz, 1H), 3.30 (dd, J=14.1, 4.9 Hz, 1H), 2.97 (dd, J=14.1, 8.9 Hz, 1H)

IR (KBr) 3400, 3330, 3250, 3040, 1705, 1655, 1600, 1525, 1500 cm$^{-1}$

MS (SIMS, positive) m/z 512 (MH$^+$)

EXAMPLE 3

Synthesis of 2-[5-benzyloxycarbonylamino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide (1) Using the title compound of Reference Example 1 and the title compound of Reference Example 3 and by a reaction similar to that in Example 1-(1), 2-[5-benzyloxycarbonylamino-2-(4-fluorophenyl)-6-oxo-1,6-dihydro-1-pyrimidinyl]-N-[1-[[5-(methoxycarbonyl)benzoaxazol-2-yl]hydroxymethyl]-2-phenylethyl]acetamide was obtained as a pale-brown solid (1.66 g, 72%).

(2) Using the objective compound of Step (1) and by a reaction similar to that in Example 1-(2), the title compound was obtained as white crystals (1.28 g, 82%).

mp 218–222° C.

$^1$H-NMR (500 MHz, DMSO-$d_6$)δ 9.04 (d, J=6.8 Hz, 1H), 8.84 (s, 1H), 8.51 (d, J=1.5 Hz, 1H), 8.40 (s, 1H), 8.23 (dd, J=8.7, 1.5 Hz, 1H), 8.04 (d, J=8.7 Hz, 1H), 7.45–7.40 (m, 4H), 7.38 (t, J=7.1 Hz, 2H), 7.33 (t, J=7.1 Hz, 1H), 7.26 (t, J=7.3 Hz, 2H), 7.22–7.13 (m, 5H), 5.51 (m, 1H), 5.17 (s, 2H), 4.53 (d, J=16.8 Hz, 1H), 4.45 (d, J=16.8 Hz, 1H), 3.92 (s, 3H), 3.31 (m, 1H), 2.97 (dd, J=14.2, 8.9 Hz, 1H)

IR (KBr) 3350, 3260, 3050, 1710, 1670, 1655, 1600, 1520 cm$^{-1}$

MS (APCI, positive) m/z 704 (MH$^+$)

EXAMPLE 4

Synthesis of 2-[5-amino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide To a solution of the title compound (462 mg, 0.657 mmol) of Example 3 and anisole (0.21 mL, 1.9 mmol) in dichloromethane (13 mL) was added under ice-cooling trifluoromethanesulfonic acid (0.35 mL, 4.0 mmol) and the mixture was stirred at 0° C. to room temperature for 1 hour. A saturated aqueous sodium hydrogencarbonate solution (13 mL) was added under ice-cooling and the mixture was stirred for 30 min. The the reaction mixture was added to a saturated aqueous sodium hydrogencarbonate solution (50 mL) and extracted with ethyl acetate. The extract was washed with saturated brine, dried over magnesium sulfate and concentrated under reduced pressure. The residue was separated and purified by silica gel column chromatography (30:1 chloroform:methanol) to give the title compound as pale-yellow crystals (368 mg, 98%).

mp 208–213° C.
$^1$H-NMR (500 MHz, DMSO-d$_6$)δ 8.97 (d, J=6.7 Hz, 1H), 8.51 (d, J=1.6 Hz, 1H), 8.24 (dd, J=8.7, 1.6 Hz, 1H), 8.05 (d, J=8.7 Hz, 1H), 7.35 (dd, J=8.8, 5.6 Hz, 2H), 7.28–7.17 (m, 6H), 7.08 (t, J=8.8 Hz, 2H), 5.50 (m, 1H), 5.12 (s, 2H), 4.48 (d, J=16.8 Hz, 1H), 4.41 (d, J=16.8 Hz, 1H), 3.93 (s, 3H), 3.31 (m, 1H), 2.97 (dd, J=14.1, 8.9 Hz, 1H)

IR (KBr) 3370, 1705, 1655, 1600 cm$^{-1}$

MS (SIMS, positive) m/z 570 (MH$^+$)

EXAMPLE 5

Synthesis of 2-[5-amino-2-(4-fluorophenyl)-6-oxo-1,6-dihydro-1-pyrimidinyl]-N-[1-[(5-carboxylbenzoxazol-2-yl)carbonyl]-2-phenylethyl]acetamide To a solution of the title compound (180 mg, 0.316 mmol) of Example 4 in a mixture of dimethylsulfide (5 mL) and dichloromethane (5 mL) was added under ice-cooling aluminum bromide (680 mg, 2.55 mmol) and the mixture was stirred at 0° C. to room temperature for 4 hours. Water (10 mL) and 1N hydrochloric acid (1 mL) were added and the mixture was stirred at room temperature for 1 hour. The precipitate was collected by filtration and washed with water and chloroform. The obtained solid was separated and purified by silica gel column chromatography (2:1 chloroform:methanol) to give the title compound as yellow crystals (146 mg, 83%).

mp 207–214° C.
$^1$H-NMR (500 MHz, DMSO-d$_6$)δ 8.94 (d, J=6.8 Hz, 1H), 8.46 (s, 1H), 8.24 (d, J=8.6 Hz, 1H), 7.87 (d, J=8.6 Hz, 1H), 7.35 (dd, J=8.7, 5.5 Hz, 2H), 7.29–7.18 (m, 6H), 7.11 (t, J=8.7 Hz, 2H), 5.55 (m, 1H), 5.13 (s, 2H), 4.48 (d, J=16.6 Hz, 1H), 4.42 (d, J=16.6 Hz, 1H), 3.30 (m, 1H), 2.97 (dd, J=14.1, 8.8 Hz, 1H)

IR (KBr) 3300, 1700, 1655, 1600, 1520, 1500 cm$^{-1}$

MS (SIMS, negative) m/z 554 (MH$^-$)

EXAMPLE 6

Synthesis of 2-[5-benzyloxycarbonylamino-2-(4-fluorophenyl)-6-oxo-1,6-dihydro-1-pyrimidinyl]-N-[1-[[6-(methoxycarbonyl)benzoxazol-2-yl]carbonyl]-2-phenylethyl]acetamide (1) Using the title compound of Reference Example 1 and the title compound of Reference Example 4 and by a reaction similar to that in Example 1-(1), 2-[5-benzyloxycarbonylamino-2-(4-fluorophenyl)-6-oxo-1,6-dihydro-1-pyrimidinyl]-N-[1-[[6-(methoxycarbonyl)benzoaxazol-2-yl]hydroxymethyl]-2-phenylethyl]acetamide was obtained as a white solid (1.09 g, 75%).

(2) Using the objective compound of Step (1) and by a reaction similar to that in Example 1-(2), the title compound was obtained as pale-yellow crystals (5.21 mg, 50%).

mp 247–250° C.
$^1$H-NMR (500 MHz, DMSO-d$_6$)δ9.02 (d, J=6.7 Hz, 1H), 8.84 (s, 1H), 8.45 (s, 1H), 8.40 (s, 1H), 8.12 (s, 2H), 7.46–7.41 (m, 4H), 7.38 (t, J=7.1 Hz, 2H), 7.33 (t, J=7.1 Hz, 1H), 7.25 (t, J=7.2 Hz, 2H), 7.22–7.13 (m, 5H), 5.53 (m, 1H), 5.17 (s, 2H), 4.53 (d, J=16.7 Hz, 1H), 4.45 (d, J=16.7 Hz, 1H), 3.93 (s, 3H), 3.30 (m, 1H), 2.97 (dd, J=14.2, 8.9 Hz, 1H)

IR (KBr) 3370, 3240, 3020, 2920, 1715, 1655, 1600, 1520 cm$^{-1}$

MS (SIMS, positive) m/z 704 (MH$^+$)

EXAMPLE 7

Synthesis of 2-[5-amino-2-(4-fluorophenyl)-6-oxo-1,6-dihydro-1-pyrimidinyl]-N-[1-[[6-(methoxycarbonyl)benzoxazol-2-yl]carbonyl]-2-phenylethyl]acetamide Using the title compound of Example 6 and by a reaction similar to that in Example 4, the title compound was obtained as yellow crystals (284 mg, 88%).

mp 197–200° C.
$^1$H-NMR (500 MHz, DMSO-d$_6$)δ 8.97 (d, J=6.7 Hz, 1H), 8.46 (s, 1H), 8.12 (s, 2H), 7.35 (dd, J=8.7, 5.5 Hz, 2H), 7.28–7.17 (m, 6H), 7.10 (t, J=8.7 Hz, 2H), 5.52 (m, 1H), 5.12 (s, 2H), 4.48 (d, J=16.6 Hz, 1H), 4.40 (d, J=16.6 Hz, 1H), 3.93 (s, 3H), 3.31 (m, 1H), 2.97 (dd, J=14.1, 8.9 Hz, 1H)

IR (KBr) 3350, 3000, 1705, 1655, 1600, 1500 cm$^{-1}$

MS (SIMS, positive) m/z 570 (MH$^+$)

EXAMPLE 8

Synthesis of 2-[5-amino-2-(4-fluorophenyl)-6-oxo-1,6-dihydro-1-pyrimidinyl]-N-[1-[(6-carboxybenzoxazol-2-yl)carbonyl]-2-phenylethyl]acetamide Using the title compound of Example 7 and by a reaction similar to that in Example 5, the title compound was obtained as pale-yellow crystals (91 mg, 52%).

mp 235–241° C.
$^1$H-NMR (500 MHz, DMSO-d$_6$)δ 8.93 (d, J=6.8 Hz, 1H), 8.29 (s, 1H), 8.14 (d, J=8.4 Hz, 1H), 7.91 (d, J=8.4 Hz, 1H), 7.35 (dd, J=8.7, 5.6 Hz, 2H), 7.28–7.17 (m, 6H), 7.11 (t, J=8.7 Hz, 2H), 5.56 (m, 1H), 5.13 (s, 2H), 4.49 (d, J=16.7 Hz, 1H), 4.42 (d, J=16.7 Hz, 1H), 3.33 (m, 1H), 2.96 (dd, J=14.0, 9.0 Hz, 1H)

IR (KBr) 3330, 1700, 1650, 1600, 1555 cm$^{-1}$

MS (SIMS, negative) m/z 554 (MH$^-$)

EXAMPLE 9

Synthesis of 2-[5-benzyloxycarbonylamino-2-(4-fluorophenyl)-6-oxo-1,6-dihydro-1-pyrimidinyl]-N-(1-formyl-2-phenylethyl)acetamide (1) Using the title compound of Reference Example 1 and L-phenylalaninol and by a reaction similar to that in Example 1-(1), 2-[5-benzyloxycarbonylamino-2-(4-fluorophenyl)-6-oxo-1,6-dihydro-1-pyrimidinyl]-N-(1-hydroxymethyl-2 -phenylethyl)acetamide was obtained as white crystals (6.51 g, 81%).

(2) Using the objective compound of Step (1) and by a reaction similar to that in Example 1-(2), the title compound was obtained as white crystals (5.45 g, 93%).

mp 138–141° C.
$^1$H-NMR (500 MHz, CDCl$_3$)δ 9.62 (s, 1H), 8.77 (brs, 1H), 7.53 (dd, J=8.7, 5.2 Hz, 2H), 7.48 (s, 1H), 7.43–7.33 (m, 5H), 7.28–7.08 (m, 7H), 6.52 (d, J=6.8.Hz, 1H), 5.24 (s, 2H), 4.77 (q, J=6.6 Hz, 1H), 4.52 (ABq, J=15.4 Hz, 2H), 3.17 (m, 2H), IR (KBr) 3270, 3010, 1725, 1645, 1600, 1520 cm$^{-1}$ MS (SIMS, positive) m/z 529 (MH$^+$)

EXAMPLE 10

Synthesis of 2-[5-benzyloxycarbonylamino-2-(4-fluorophenyl)-6-oxo-1,6-dihydro-1-pyrimidinyl]-N-[1-[[5-(benzyloxycarbonyl)benzoxazol-2-yl]carbonyl]-2-phenylethyl]acetamide (1) To a solution of the title compound (4.06 g, 7.68 mmol) of Example 9 and acetone cyanohydrin (2.1 mL, 23 mmol) in dichloromethane (50 mL) was added triethylamine (0.64 mL, 4.6 mmol) and the mixture was stirred at room temperature for 2 hours. The precipitate was collected by filtration and washed with ethyl acetate. The filtrate and washing solution were combined and the organic solvent was evaporated under reduced pressure. The obtained concentrate was added to water (100 mL) and extracted with ethyl acetate. The extract was washed with saturated brine, dried over magnesium sulfate and concentrated under reduced pressure. The obtained solid was washed with ether, combined with the precipitate obtained earlier and dried in vacuo to give 2-[5-benzyloxycarbonylamino-2-(4- fluorophenyl)-6-oxo-1,6-dihydro-1-pyrimidinyl]-N-[1-(cyanohydroxymethyl)-2-phenylethyl]acetamide as a white solid (3.68 g, 86%).

(2) To a mixture of chloroform (10 mL) and ethanol (4.5 mL, 77 mmol) was added dropwise under ice-cooling acetyl chloride (5.0 mL, 70 mmol) over 15 min. The mixture was stirred at 0° C. for 10 min and the objective compound (1.30 g, 2.34 mmol) of Step (1) was added. The mixture was stirred at 0° C. to room temperature for 3 hours. The solvent was evaporated under reduced pressure to give white solid. Thereto were added ethanol (13 mL) and the title compound (735 mg, 3.02 mmol) of Reference Example 5 and the mixture was heated to 65° C. and stirred for 6 hours. The solvent was evaporated under reduced pressure and the obtained concentrate was added to a 0.5N aqueous sodium hydroxide solution (50 mL) and extracted with ethyl acetate. The extract was washed with saturated brine and concentrated under reduced pressure. The residue was separated and purified by silica gel column chromatography (50:1 chloroform:methanol) to give a mixture containing 2-[5-benzyloxycarbonylamino-2-(4-fluorophenyl)-6-oxo-1,6-dihydro-1-pyrimidinyl]-N-[1-[[5-(benzyloxycarbonyl)benzoxazol-2-yl]hydroxymethyl]-2-phenylethyl]acetamide as a pale-yellow solid (395 mg).

(3) Using a mixture containing the objective compound of Step (2) and by a reaction similar to that in Example 1-(2), the title compound was obtained as pale-yellow crystals (179 mg, yield from 2-[5-benzyloxycarbonylamino-2-(4-fluorophenyl)-6-oxo-1,6-dihydro-1-pyrimidinyl]-N-[1-(cyanohydroxymethyl)-2-phenylethyl]acetamide, 10%).

mp 221–225° C.

$^1$H-NMR (500 MHz, DMSO-d$_6$)δ 9.02 (d, J=6.8 Hz, 1H), 8.83 (s, 1H), 8.55 (d, J=1.4 Hz, 1H), 8.40 (s, 1H), 8.26 (dd, J=8.8, 1.4 Hz, 1H), 8.05 (d, J=8.8 Hz, 1H), 7.52 (d, J=7.2 Hz, 2H), 7.46–7.35 (m, 9H), 7.32 (t, J=7.1 Hz, 1H), 7.28–7.12 (m, 7H), 5.51 (m, 1H), 5.42 (s, 2H), 5.17 (s, 2H), 4.53 (d, J=16.6 Hz, 1H), 4.45 (d, J=16.6 Hz, 1H), 3.32 (m, 1H), 2.96 (dd, J=14.1, 9.0 Hz, 1H)

IR (KBr) 3370, 1715, 1670, 1655, 1600, 1520 cm$^{-1}$

MS (SIMS, positive) m/z 780 (MH$^+$)

EXAMPLE 11

Synthesis of 2-[5-benzyloxycarbonylamino-2-(4-fluorophenyl)-6-oxo-1,6-dihydro-1-pyrimidinyl]-N-[1-[[5-(ethylaminocarbonyl)benzoxazol-2-yl]carbonyl]-2-phenylethyl]acetamide (1) To a solution of the objective compound (2.00 g, 2.83 mmol) of Example 3-(1) in DMSO (250 mL) was added a 1N aqueous sodium hydroxide solution (30 mL) and the mixture was stirred at room temperature for 1 hour. The reaction mixture was added to 0.1N hydrochloric acid (1000 mL) and extracted with ethyl acetate. The extract was washed with saturated brine, dried over magnesium sulfate and concentrated under reduced pressure. The obtained solid was washed with ether and dried in vacuo to give 2-[5-benzyloxycarbonylamino-2-(4-fluorophenyl)-6-oxo-1,6-dihydro-1-pyrimidinyl]-N-[1-[(5-carboxybenzoxazol-2-yl)hydroxymethyl]-2-phenylethyl]acetamide as a white solid (1.58 g, 81%).

(2) To a solution of the objective compound (450 mg, 0.651 mmol) of Step (1), ethylamine hydrochloride (67 mg, 0.82 mmol) and HOBT (176 mg, 1.30 mmol) in DMF (10 mL) were added N-ethylmorpholine (0.10 mL, 0.79 mmol) and WSCI hydrochloride (148 mg, 0.772 mmol) and the mixture was stirred at room temperature for 3.5 hours. The reaction mixture was added to 1N hydrochloric acid (80 mL) and extracted with ethyl acetate. The extract was washed successively with a saturated aqueous sodium hydrogencarbonate solution and saturated brine, dried over magnesium sulfate and concentrated under reduced pressure. The obtained solid was washed with ether and dried in vacuo to give 2-[5-benzyloxycarbonylamino-2-(4-fluorophenyl)-6-oxo-1,6-dihydro-1-pyrimidinyl]-N-[1-[[5-(ethylaminocarbonyl)benzoxazol-2-yl]hydroxymethyl]-2-phenylethyl]acetamide as a white solid (397 g, 85%).

(3) To a solution of the objective compound (448 mg, 0.623 mmol) of Step (2) in DMSO (5 mL) was added Dess-Martin periodinane (446 mg, 1.05 mmol) and the mixture was stirred at room temperature for 1.5 hours. To the reaction mixture was added a saturated aqueous sodium hydrogencarbonate solution (5 mL) containing sodium thiosulfate in a concentration of 0.22 g/mL, and the mixture was stirred at room temperature and extracted with ethyl acetate. The insoluble material in the extract was collected by filtration and the filtrate was washed successively with a saturated aqueous sodium hydrogencarbonate solution and saturated brine, dried over magnesium sulfate and concentrated under reduced pressure. The residue and the insoluble material obtained earlier were combined, and separated and purified by silica gel column chromatography (50:1 chloroform:methanol) to give the title compound as pale-yellow crystals (268 mg, 60%).

mp 256–261° C.

$^1$H-NMR (500 MHz, DMSO-d$_6$)δ 9.00 (d, J=6.9 Hz, 1H), 8.86 (s, 1H), 8.65 (t, J=5.5 Hz, 1H), 8.46 (d, J=1.6 Hz, 1H), 8.40 (s, 1H), 8.14 (dd, J=8.7, 1.6 Hz, 1H), 7.97 (d, J=8.7 Hz, 1H), 7.46–7.40 (m, 4H), 7.38 (t, J=7.1 Hz, 2H), 7.33 (t, J=7.1 Hz, 1H), 7.26 (t, J=7.2 Hz, 2H), 7.22–7.13 (m, 5H), 5.54 (m, 1H), 5.17 (s, 2H), 4.53 (d, J=16.4 Hz, 1H), 4.46 (d, J=16.4 Hz, 1H), 3.3 (m, 3H), 2.95 (dd, J=14.1, 9.1 Hz, 1H), 1.16 (t, J=7.2 Hz, 3H)

IR (KBr) 3350, 3250, 3020, 1715, 1655, 1600, 1520 cm$^{-1}$

EXAMPLE 12

Synthesis of 2-[5-amino-2-(4-fluorophenyl)-6-oxo-1,6-dihydro-1-pyrimidinyl]-N-[1-[[5-(ethylaminocarbonyl)benzoxazol-2-yl]carbonyl]-2-phenylethyl]acetamide Using the title compound of Example 11 and by a reaction similar to that in Example 4, the title compound was obtained as pale-yellow crystals (111 mg, 68%).

mp 223–239° C.

$^1$H-NMR (500 MHz, DMSO-d$_6$)δ 8.94 (d, J=6.8 Hz, 1H), 8.65 (t, J=5.5 Hz, 1H), 8.46 (d, J=1.6 Hz, 1H), 8.14 (dd, J=8.7, 1.6 Hz, 1H), 7.98 (d, J=8.7 Hz, 1H), 7.35 (dd, J=8.7, 5.5 Hz, 2H), 7.29–7.18 (m, 6H), 7.10 (t, J=8.7 Hz, 2H), 5.53 (m, 1H), 5.12 (s, 2H), 4.48 (d, J=16.7 Hz, 1H), 4.42 (d, J=16.7 Hz, 1H), 3.3 (m, 3H), 2.96 (dd, J=14.1, 9.0 Hz, 1H), 1.16 (t, J=7.2 Hz, 3H)

IR (KBr) 3300, 1705, 1640, 1600, 1525, 1500 cm$^{-1}$

EXAMPLE 13

Synthesis of 2-[5-benzyloxycarbonylamino-2-(4-fluorophenyl)-6-oxo-1,6-dihydro-1-pyrimidinyl]-N-[1-[(5-nitrobenzoxazol-2-yl)carbonyl]-2-phenylethyl]acetamide (1) Using the title compound of Reference Example 1 and the title compound of Reference Example 6 and by a reaction similar to that in Example 1-(1), 2-[5-benzyloxycarbonylamino-2-(4-fluorophenyl)-6-oxo-1,6-dihydro-1-pyrimidinyl]-N-[1-[(5-nitrobenzoxazol-2-yl)hydroxymethyl]-2-phenylethyl]acetamide was obtained as a pale-yellow solid (2.54 g, 99%).

(2) Using the objective compound of Step (1) and by a reaction similar to that in Example 1-(2), the title compound was obtained as a pale-brown solid (1.47 g, 59%).

$^1$H-NMR (300 MHz, DMSO-d$_6$)δ 9.07 (d, J=6.8 Hz, 1H), 8.90 (d, J=2.2 Hz, 1H), 8.85 (s, 1H), 8.52 (dd, J=9.1, 2.2 Hz,

1H), 8.40 (s, 1H), 8.18 (d, J=9.1 Hz, 1H), 7.53–7.10 (m, 14H), 5.49 (m, 1H), 5.17 (s, 2H), 4.58 (d, J=16.8 Hz, 1H), 4.44 (d, J=16.8 Hz, 1H), 3.4–3.25 (m, 1H), 2.97 (dd, J=14.2, 8.9 Hz, 1H)

IR (KBr) 3350, 3050, 1715, 1655, 1600, 1520 cm$^{-1}$

EXAMPLE 14
Synthesis of 2-[5-benzyloxycarbonylamino-2-(4-fluorophenyl)-6-oxo-1,6-dihydro-1-pyrimidinyl]-N-[1-[(5-aminobenzoxazol-2-yl)carbonyl]-2-phenylethyl]acetamide To a solution of the title compound (1.340 g, 1.940 mmol) of Example 13 in a mixture of THF (40 mL), water (7 mL) and methanol (7 mL) were added iron powder (2.734 g, 48.95 mmol) of 1N hydrochloric acid (1.64 mL), and the mixture was stirred at room temperature for 18 hours. The insoluble material was removed through celite and washed with chloroform. The filtrate and washing solution were combined and washed with a saturated aqueous sodium hydrogencarbonate solution and saturated brine, dried over sodium sulfate and concentrated under reduced pressure. The residue was separated and purified by silica gel column chromatography (96:4 chloroform:methanol) and (97:3 chloroform:methanol) to give the title compound as an organge solid (1.0004 g, 78%).

$^1$H-NMR (300 MHz, DMSO-d$_6$)δ 8.93 (s, 1H), 8.92 (d, J=6.6 Hz, 1H), 8.41 (s, 1H), 7.54 (d, J=8.9 Hz, 1H), 7.48–7.13 (m, 14H), 6.95 (d, J=2.0 Hz, 1H), 6.92 (dd, J=8.9, 2.0 Hz, 1H), 5.56 (m, 1H), 5.37 (s, 2H), 5.17 (s, 2H), 4.53 (d, J=16.7 Hz, 1H), 4.44 (d, J=16.7 Hz, 1H), 3.25 (dd, J=14.0, 4.4 Hz, 1H), 2.92 (dd, J=14.0, 8.9 Hz, 1H)

IR (KBr) 3325, 3000, 1695, 1650, 1600, 1510 cm$^{-1}$

EXAMPLE 15
Synthesis of 2-[5-amino-2-(4-fluorophenyl)-6-oxo-1,6-dihydro-1-pyrimidinyl]-N-[1-[(5-aminobenzoxazol-2-yl)carbonyl]-2-phenylethyl]acetamide Using the title compound of Example 14 and by a reaction similar to that in Example 4, the title compound was obtained as a yellow solid (228 mg, 83%).

$^1$H-NMR (500 MHz, DMSO-d$_6$)δ 8.83 (d, J=7.0 Hz, 1H), 7.53 (d, J=8.8 Hz, 1H), 7.36 (m, 2H), 7.28 (s, 1H), 7.26 (t, J=7.3 Hz, 2H), 7.23–7.17 (m, 3H), 7.13 (t, J=8.8 Hz, 2H), 6.96 (d, J=2.2 Hz, 1H), 6.92 (dd, J=8.8, 2.2 Hz, 1H), 5.56 (m, 1H), 5.35 (s, 2H), 5.14 (s, 2H), 4.48 (d, J=16.6 Hz, 1H), 4.41 (d, J=16.6 Hz, 1H), 3.25 (dd, J=14.1, 4.8 Hz, 1H), 2.93 (dd, J=14.1, 8.8 Hz, 1H)

IR (KBr) 3250, 3000, 1700, 1650, 1600, 1520 cm$^{-1}$
MS (SIMS, positive) m/z 527 (MH$^+$)

EXAMPLE 16
Synthesis of 2-[5-benzyloxycarbonylamino-2-(4-fluorophenyl)-6-oxo-1,6-dihydro-1-pyrimidinyl]-N-[1-[[5-(trifluoromethanesulfonylamino)benzoxazol-2-yl]carbonyl]-2-phenylethyl]acetamide To a solution of the title compound (149 mg, 0.226 mmol) of Example 14 in THF (3 mL) was added triethylamine (0.038 mL, 0.273 mmol) and the mixture was cooled to −78° C. Thereto was added dropwise anhydrous trifluoromethanesulfonic acid (0.046 mL, 0.273 mmol). The obtained mixture was stirred at the same temperature for 1 hour. Water (10 mL) was added and the mixture was allowed to warm to room temperature and extracted with ethyl acetate and chloroform. The extract was washed with saturated brine, dried over magnesium sulfate and concentrated under reduced pressure. The residue was separated and purified by silica gel column chromatography (95:5 chloroform:methanol–90:10 chloroform:methanol) to give the title compound as a pale-yellow solid (145 mg, 81%).

$^1$H-NMR (300 MHz, DMSO-d$_6$)δ 8.99 (d, J=6.9 Hz, 1H), 8.90 (s, 1H), 8.41 (s, 1H), 7.96 (d, J=8.9 Hz, 1H), 7.83 (d, J=2.0 Hz, 1H), 7.50 (dd, J=8.9, 2.0 Hz, 1H), 7.44–7.14 (m, 14H), 5.54 (m, 1H), 5.17 (s, 2H), 4.53 (d, J=16.8 Hz, 1H), 4.45 (d, J=16.8 Hz, 1H), 3.4–3.1 (m, 1H), 2.94 (dd, J=14.1, 9.0 Hz, 1H)

IR (KBr) 3325, 3025, 1705, 1650, 1600, 1520 cm$^{-1}$
MS (SIMS, positive) m/z 793 (MH$^+$)

EXAMPLE 17
Synthesis of 2-[5-amino-2-(4-fluorophenyl)-6-oxo-1,6-dihydro-1-pyrimidinyl]-N-[1-[[5-(trifluoromethanesulfonylamino)benzoxazol-2-yl]carbonyl]-2-phenylethyl]acetamide Using the title compound of Example 16 and by a reaction similar to that in Example 4, the title compound was obtained as a pale-yellow solid (67 mg, 58%).

mp 165–170° C.

$^1$H-NMR (500 MHz, DMSO-d$_6$)δ 8.91 (d, J=6.9 Hz, 1H), 7.91 (d, J=8.9 Hz, 1H), 7.79 (d, J=2.0 Hz, 1H), 7.48 (dd, J=8.9, 2.0 Hz, 1H), 7.36 (m, 2H), 7.29 (s, 1H), 7.26 (t, J=7.3 Hz, 2H), 7.23–7.17 (m, 3H), 7.12 (t, J=8.8 Hz, 2H), 5.53 (m, 1H), 4.48 (d, J=16.6 Hz, 1H), 4.42 (d, J=16.6 Hz, 1H), 3.31 (dd, J=14.1, 4.7 Hz, 1H), 2.95 (dd, J=14.1, 8.9 Hz, 1H)

IR (KBr) 3300, 3000, 1645, 1600, 1520, 1500 cm$^{-1}$
MS (SIMS, positive) m/z 659 (MH$^+$)

EXAMPLE 18
Synthesis of 2-[5-benzyloxycarbonylamino-2-(4-fluorophenyl)-6-oxo-1,6-dihydro-1-pyrimidinyl]-N-[1-[(5-(methoxycarbonyl)benzoxazol-2-yl)carbonyl]-2-phenylethyl]acetamide 1) Using the title compound of Reference Example 1 and the title compound of Reference Example 7 and by a reaction similar to that in Example 1-(1), 2-[5-benzyloxycarbonylamino-2-(4-fluorophenyl)-6-oxo-1,6-dihydro-1-pyrimidinyl]-N-[1-[(5-methoxybenzoxazol-2-yl)hydroxymethyl]-2-phenylethyl]acetamide was obtained as a pale-red solid (810 mg, 93%).

(2) Using the above-mentioned compound and by a reaction similar to that in Example 1-(2), the title compound was obtained the as pale-yellow crystals (906 mg, 57%).

mp 233–235° C.

$^1$H-NMR (500 MHz, DMSO-d$_6$ δ8.98 (d, J=6.9 Hz, 1H), 8.92 (s, 1H), 8.41 (s, 1H), 7.81 (d, J=9.1 Hz, 1H), 7.52 (d, J=2.4 Hz, 1H), 7.46–7.41 (m, 4H), 7.38 (t, J=7.1 Hz, 2H), 7.33 (t, J=7.1 Hz, 1H), 7.28–7.14 (m, 8H), 5.55 (m, 1H), 5.17 (s, 2H), 4.53 (d, J=16.7 Hz, 1H), 4.44 (d, J=16.7 Hz, 1H), 3.86 (s, 3H), 3.30 (dd, J=14.1, 4.5 Hz, 1H), 2.94 (dd, J=14.1, 9.0 Hz, 1H)

IR (KBr) 3390, 3300, 1705, 1660, 1605, 1520 cm$^{-1}$
MS (SIMS, positive) m/z 676 (MH$^+$)

EXAMPLE 19
Synthesis of 2-[5-amino-2-(4-fluorophenyl)-6-oxo-1,6-dihydro-1-pyrimidinyl]-N-[1-[(5-methoxycarbonyl)benzoxazol-2-yl)carbonyl]-2-phenylethyl]acetamide Using the title compound of Example 18 and by a reaction similar to that in Example 4, the title compound was obtained as pale-yellow crystals (586 mg, 92%).

mp 163–169° C.

$^1$H-NMR (500 MHz, DMSO-d$_6$)δ8.92 (d, J=6.9 Hz, 1H), 7.82 (d, J=9.1 Hz, 1H), 7.53 d, J=2.4 Hz, 1H), 7.35 (dd, J=8.6, 5.6 Hz, 2H), 7.29–7.18 (m, 7H), 7.11 (t, J=8.6 Hz, 2H), 5.54 (m, 1H), 5.16 (s, 2H), 4.48 (d, J=16.5 Hz, 1H), 4.41 (d, J=16.5 Hz, 1H), 3.86 (s, 3H), 3.30 (dd, J=14.1, 4.4 Hz, 1H), 2.95 (dd, J=14.1, 9.1 Hz, 1H)

IR (KBr) 3390, 3270, 1705, 1660, 1605, 1505 cm$^{-1}$
MS (SIMS, positive) m/z 542 (MH$^+$)

EXAMPLE 20

Synthesis of 2-[5-amino-2-(4-fluorophenyl)-6-oxo-1,6-dihydro-1-pyrimidinyl]-N-[1-[(5-hydroxybenzoxazol-2-yl)carbonyl]-2-phenylethyl]acetamide To a solution of the title compound (452 mg, 0.835 mmol) of Example 19 in dichloromethane (10 mL) was added under ice-cooling a solution (1.0 M, 8.4 mL, 8.4 mmol) of boron tribromide in dichloromethane and the mixture was stirred at 0° C. to room temperature for 4 hours. Methanol (1.5 mL) was added and the mixture was stirred for 10 min. The reaction mixture was added to a saturated aqueous sodium hydrogencarbonate solution (50 mL) and extracted with ethyl acetate. The extract was washed with saturated brine, dried over magnesium sulfate and was concentrated under reduced pressure. The residue was separated and purified by silica gel column chromatography (10:1 chloroform:methanol) to give the title compound as a yellow solid (340 mg, 77%).

$^1$H-NMR (500 MHz, DMSO-$d_6$) δ9.95 (brs, 1H), 8.89 (d, J=6.9 Hz, 1H), 7.69 (d, J=8.9 Hz, 1H), 7.35 (dd, J=8.5, 5.6 Hz, 2H), 7.29–7.07 (m, 10H), 5.54 (m, 1H), 5.15 (s, 2H), 4.48 (d, J=16.5 Hz, 1H), 4.41 (d, J=16.5 Hz, 1H), 3.27 (dd, J=14.1, 4.7 Hz, 1H), 2.94 (dd, J=14.1, 9.0 Hz, 1H)

IR (KBr) 3410, 3290, 1705, 1660, 1605, 1520, 1505 cm$^{-1}$

MS (SIMS, positive) m/z 528 (MH$^+$)

EXAMPLE 21

Synthesis of 2-[5-benzyloxycarbonylamino-2-(4-fluorophenyl)-6-oxo-1,6-dihydro-1-pyrimidinyl]-N-[2-phenyl-1-[(2-thiazolyl)carbonyl]ethyl]acetamide (1) To a solution of the title compound (724 mg, 1.37 mmol) of Example 9 in dichloromethane (15 mL) was added 2-trimethylsilylthiazole (0.23 mL, 1.4 mmol) and the mixture was stirred at room temperature for one day. A solution (1M, 2.5 mL, 2.5 mmol) of tetrabutyl ammonium fluoride in THF was added and the mixture was stirred for 30 min. The reaction mixture was added to a saturated aqueous sodium hydrogencarbonate solution (50 mL) and extracted with chloroform. The extract was dried over anhydrous magnesium sulfate and concentrated under reduced pressure. The residue was separated and purified by silica gel column chromatography (50:1 chloroform:methanol) to give 2-[5-benzyloxycarbonylamino-2-(4-fluorophenyl)-6-oxo-1,6-dihydro-1-pyrimidinyl]-N-[2-phenyl-1-[(2-thiazolyl)hydroxymethyl]ethyl]acetamide was a white solid (665 mg, 79%).

(2) Using the above-mentioned compound and by a reaction similar to that in Example 1-(2), the title compound was obtained as white crystals (554 mg, 86%).

mp 209–211° C $^1$H-NMR (500 MHz, DMSO-$d_6$) δ8.92 (s, 1H), 8.85 (d, J=7.5 Hz, 1H), 8.41 (s, 1H), 8.30 (d, J=3.0 Hz, 1H), 8.21 (d, J=3.0 Hz, 1H), 7.47–7.41 (m, 4H), 7.38 (t, J=7.1 Hz, 2H), 7.33 (t, J=7.1 Hz, 1H), 7.27–.18 (m, 5H), 7.15 (d, J=7.0 Hz, 2H), 5.67 (m, 1H), 5.17 (s, 2H), 4.55 (d, J=16.6 Hz, 1H), 4.42 (d, J=16.6 Hz, 1H), 3.19 (dd, J=14.0, 4.2 Hz, 1H), 2.88 (dd, J=14.0, 9.2 Hz, 1H)

IR (KBr) 3360, 1725, 1655, 1605, 1525 cm$^{-1}$

MS (SIMS, positive) m/z 612 (MH$^+$)

EXAMPLE 22

Synthesis of 2-[5-amino-2-(4-fluorophenyl)-6-oxo-1,6-dihydro-1-pyrimidinyl]-N-[2-phenyl-1-[(2-thiazolyl)carbonyl]ethyl]acetamide using the title compound of Example 21 and by a reaction similar to that in Example 4, the title compound was obtained as white crystals (370 mg, 100%).

mp 199–203° C $^1$H-NMR (500 MHz, DMSO-$d_6$) δ8.79 (d, J=7.5 Hz, 1H), 8.30 (d, J=2.9 Hz, 1H), 8.21 (d, J=2.9 Hz, 1H), 7.36 (dd, J=8.5, 5.6 Hz, 2H), 7.29–7.14 (m, 8H), 5.67 (m, 1H), 5.15 (s, 2H), 4.50 (d, J=16.6 Hz, 1H), 4.39 (d, J=16.6 Hz, 1H), 3.19 (dd, J=14.0, 4.3 Hz, 1H), 2.89 (dd, J=14.0, 9.2 Hz, 1H)

IR (KBr) 3380, 1650, 1605, 1500 cm$^{-1}$

MS (SIMS, positive) m/z 478 (MH$^+$).

EXAMPLE 23

Synthesis of 2-[5-benzyloxycarbonylamino-2-(4-fluorophenyl)-6-oxo-1,6-dihydro-1-pyrimidinyl]-N-[1-[(2-oxazolinyl)carbonyl]-2-phenylethyl]acetamide (1) Using the title compound of Reference Example 1 and the title compound of Reference Example 8 and by a reaction similar to that in Example 1-(1), a mixture containing 2-[5-benzyloxycarbonylamino-2-(4-fluorophenyl)-6-oxo-1,6-dihydro-1-pyrimidinyl]-N-[1-[(2-oxazolinyl)hydroxymethyl]-2-phenylethyl]acetamide was obtained as a white solid (521 mg).

(2) Using the above-mentioned compound and by a reaction similar to that in Example 1-(2), the title compound was obtained as white crystals (173 mg, yield from the title compound of Reference Example 8, 23%).

mp 215–220° C. $^1$H-NMR (300 MHz, DMSO-$d_6$) δ8.92 (t, J=5.7 Hz, 1H), 8.90 (s, 1H), 8.68 (d, J=7.2 Hz, 1H), 8.42 (s, 1H), 7.51–7.08 (m, 14H), 5.25 (m, 1H), 5.18 (s, 2H), 4.50 (d, J=16.8 Hz, 1H), 4.42 (d, J=16.8 Hz, 1H), 3.68 (t, J=6.1 Hz, 2H), 3.48 (m, 2H), 3.10 (dd, J=14.0, 4.2 Hz, 1H), 2.77 (dd, J=14.0, 8.9 Hz, 1H)

IR (KBr) 3380, 3270, 1725, 1655, 1600, 1520 cm$^{-1}$

EXAMPLE 24

Synthesis of 2-[5-amino-2-(4-fluorophenyl)-6-oxo-1,6-dihydro-1-pyrimidinyl]-N-[1-[(2-oxazolinyl)carbonyl]-2-phenylethyl]acetamide Using the title compound of Example 23 and by a reaction similar to that in Example 4, the title compound was obtained as white crystals (48 mg, 49%).

mp 180–185° C. $^1$H-NMR (300 MHz, DMSO-$d_6$) δ8.92 (t, J=5.8 Hz, 1H), 8.62 (d, J=7.2 Hz, 1H), 7.40 (dd, J=8.7, 5.5 hz, 2H), 7.30–7.09 (m, 8H), 5.24 (m, 1H), 5.15 (s, 2H), 4.46 (d, J=16.7 hz, 1H), 4.38 (d, J=16.7 Hz, 1H), 3.68 (t, J=6.2 Hz, 2H), 3.48 (m, 2H), 3.10 (dd, J=14.0, 4.2 Hz, 1H), 2.78 (dd, J=14.0, 8.8 Hz, 1H)

IR (KBr) 3350, 1655, 1600, 1530 cm$^{-1}$ .

The compounds obtained in the above-mentioned Examples are shown in Tables 1–4, wherein Me is methyl, Et is ethyl and Bn is benzyl.

TABLE 1

| Example No. | R | R⁵ | Y | Z |
|---|---|---|---|---|
| 1 | benzyl -OC(O)CH₂- | 4-fluorophenyl | phenyl | 2-benzoxazolyl |
| 2 | H | 4-fluorophenyl | phenyl | 2-benzoxazolyl |
| 3 | benzyl -OC(O)CH₂- | 4-fluorophenyl | phenyl | 2-benzoxazolyl-5-CO₂Me |
| 4 | H | 4-fluorophenyl | phenyl | 2-benzoxazolyl-5-CO₂Me |
| 5 | H | 4-fluorophenyl | phenyl | 2-benzoxazolyl-5-CO₂H |
| 6 | benzyl -OC(O)CH₂- | 4-fluorophenyl | phenyl | 2-benzoxazolyl-6-CO₂Me |

TABLE 2

| Example No. | R | R⁵ | Y | Z |
|---|---|---|---|---|
| 7 | H | 4-fluorophenyl | phenyl | 2-benzoxazolyl-6-CO₂Me |

TABLE 2-continued
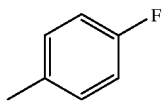
| Example No. | R | R⁵ | Y | Z |
|---|---|---|---|---|
| 8 | H | 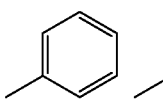 | 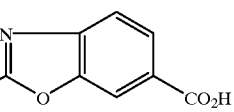 | 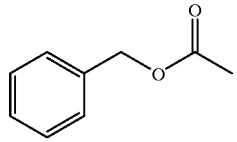 |
| 9 | 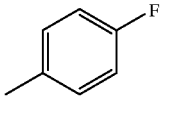 |  | 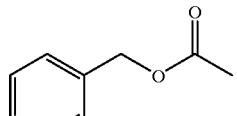 | —CH=O |
| 10 | 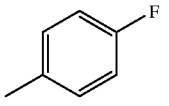 | 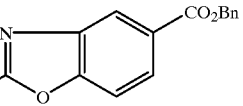 | 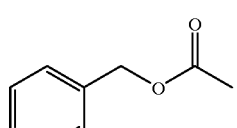 | 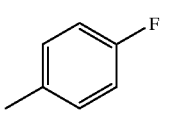 |
| 11 | 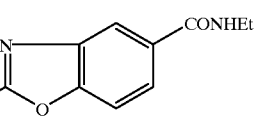 | 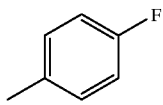 | 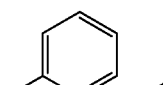 | 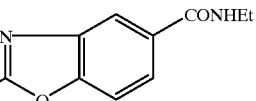 |
| 12 | H | 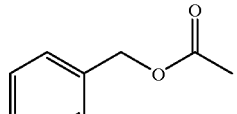 | 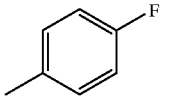 | 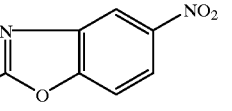 |
TABLE 3
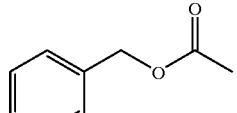
| Example No. | R | R⁵ | Y | Z |
|---|---|---|---|---|
| 13 | 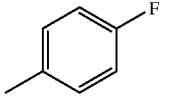 | | | |
| 14 | 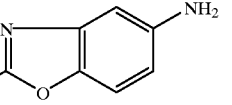 | | | |

TABLE 3-continued
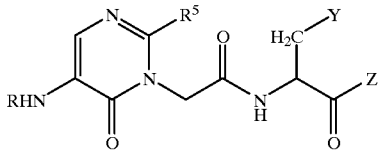
| Example No. | R | R⁵ | Y | Z |
|---|---|---|---|---|
| 15 | H | 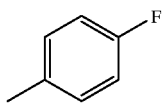 | 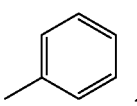 | 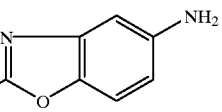 |
| 16 | 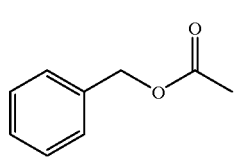 | 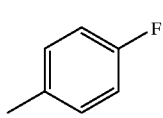 | 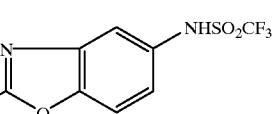 | 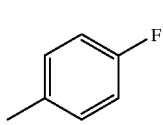 |
| 17 | H | 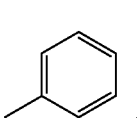 | 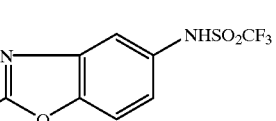 | 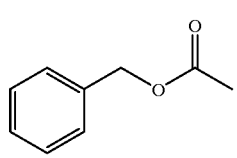 |
| 18 | 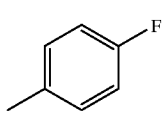 | 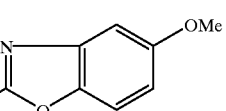 | 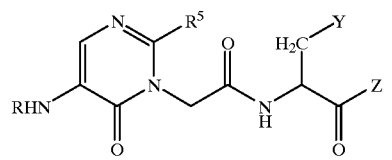 | 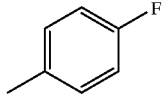 |
TABLE 4
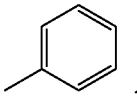
| Example No. | R | R⁵ | Y | Z |
|---|---|---|---|---|
| 19 | H | 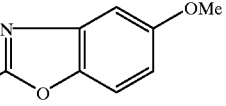 | 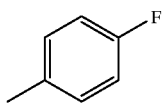 | 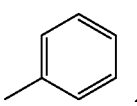 |
| 20 | H | 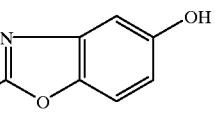 | 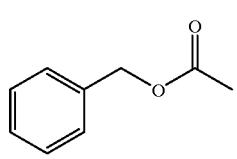 | 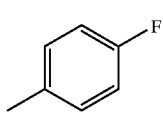 |
| 21 | 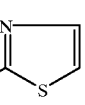 | 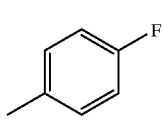 | 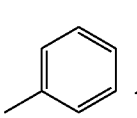 | 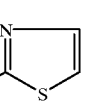 |
| 22 | H | | | |

TABLE 4-continued

| Example No. | R | R⁵ | Y | Z |
|---|---|---|---|---|
| 23 | benzyl ester (PhCH₂O-C(O)-CH₂-) | 4-F-C₆H₄- | C₆H₅- | 2-oxazoline |
| 24 | H | 4-F-C₆H₄- | C₆H₅- | 2-oxazoline |

EXAMPLE 25–EXAMPLE 94

The compounds shown in Tables 5 to 9 were synthesized according to the above-mentioned Examples. In the Tables, Me is methyl and Et is ethyl.

TABLE 5

| Example No. | R | R⁵ | Y | Z |
|---|---|---|---|---|
| 25 | benzyl ester (PhCH₂O-C(O)-CH₂-) | 4-F-C₆H₄- | C₆H₅- | 5-F-benzoxazol-2-yl |
| 26 | H | 4-F-C₆H₄- | C₆H₅- | 5-F-benzoxazol-2-yl |
| 27 | benzyl ester (PhCH₂O-C(O)-CH₂-) | 4-F-C₆H₄- | C₆H₅- | 5-CO₂Et-benzoxazol-2-yl |
| 28 | H | 4-F-C₆H₄- | C₆H₅- | 5-CO₂Et-benzoxazol-2-yl |

TABLE 5-continued
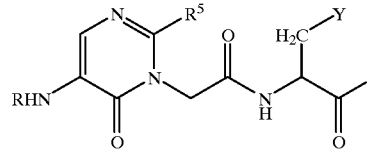
| Example No. | R | R⁵ | Y | Z |
|---|---|---|---|---|
| 29 | 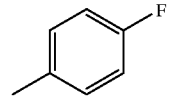 | 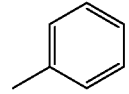 | 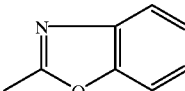 | 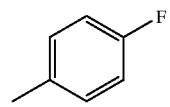 |
| 30 | H | 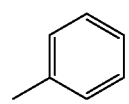 | 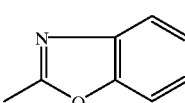 | 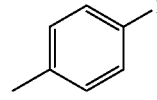 |
| 31 | 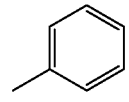 | 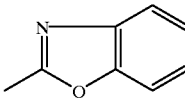 | 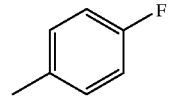 | 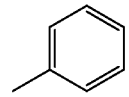 |
| 32 | H | 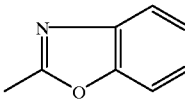 | 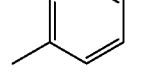 | 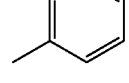 |
| 33 | 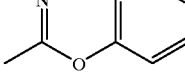 | 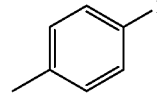 | 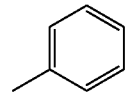 | 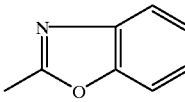 |
| 34 | H | 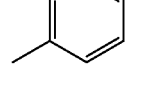 | 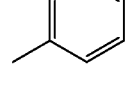 | 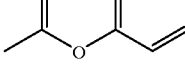 |
| 35 | 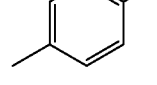 | 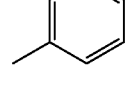 | 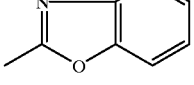 | 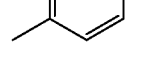 |
| 36 | H | 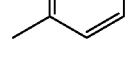 | | |
| 37 | 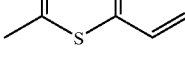 | | | |

TABLE 5-continued

| Example No. | R | R⁵ | Y | Z |
|---|---|---|---|---|
| 38 | H | 4-fluorophenyl | phenyl | benzothiazol-2-yl |
| 39 | benzyloxycarbonyl | 4-fluorophenyl | 4-fluorophenyl | benzoxazol-2-yl |

TABLE 6

| Example No. | R | R⁵ | Y | Z |
|---|---|---|---|---|
| 40 | H | 4-fluorophenyl | 4-fluorophenyl | benzoxazol-2-yl |
| 41 | benzyloxycarbonyl | phenyl | phenyl | benzoxazol-2-yl |
| 42 | H | phenyl | phenyl | benzoxazol-2-yl |
| 43 | benzyloxycarbonyl | phenyl | phenyl | 5-(CO₂Et)-benzoxazol-2-yl |
| 44 | H | phenyl | phenyl | 5-(CO₂Et)-benzoxazol-2-yl |

TABLE 6-continued

| Example No. | R | R⁵ | Y | Z |
|---|---|---|---|---|
| 45 | benzyl carbamate (PhCH₂OC(O)-) | phenyl | phenyl | 2-methyl-oxazolo[4,5-b]pyridine |
| 46 | H | phenyl | phenyl | 2-methyl-oxazolo[4,5-b]pyridine |
| 47 | benzyl carbamate | 3-methylphenyl | phenyl | 2-methylbenzoxazole |
| 48 | H | 3-methylphenyl | phenyl | 2-methylbenzoxazole |
| 49 | benzyl carbamate | 3-methylphenyl | phenyl | 2-methylbenzoxazole-5-CO₂Me |
| 50 | H | 3-methylphenyl | phenyl | 2-methylbenzoxazole-5-CO₂Me |
| 51 | benzyl carbamate | 3-methylphenyl | phenyl | 2-methylbenzoxazole-5-CO₂Et |
| 52 | H | 3-methylphenyl | phenyl | 2-methylbenzoxazole-5-CO₂Et |
| 53 | benzyl carbamate | 3-methylphenyl | phenyl | 2-methylbenzoxazole-5-CONH₂ |

TABLE 6-continued

| Example No. | R | R⁵ | Y | Z |
|---|---|---|---|---|
| 54 | H | 3-methylphenyl | phenyl | 2-methylbenzoxazole-5-carboxamide (CONH₂) |

TABLE 7

| Example No. | R | R⁵ | Y | Z |
|---|---|---|---|---|
| 55 | benzyloxycarbonyl (Cbz) | 3-methylphenyl | phenyl | 2-methylbenzoxazole-5-CONHEt |
| 56 | H | 3-methylphenyl | phenyl | 2-methylbenzoxazole-5-CONHEt |
| 57 | benzyloxycarbonyl (Cbz) | 3-methylphenyl | phenyl | 2-methylbenzoxazole-5-CONEt₂ |
| 58 | H | 3-methylphenyl | phenyl | 2-methylbenzoxazole-5-CONEt₂ |
| 59 | benzyloxycarbonyl (Cbz) | 3-methylphenyl | phenyl | 2-methyloxazolo[4,5-b]pyridine |
| 60 | H | 3-methylphenyl | phenyl | 2-methyloxazolo[4,5-b]pyridine |

TABLE 7-continued

| Example No. | R | R⁵ | Y | Z |
|---|---|---|---|---|
| 61 | benzyl ester CH₂ | 3-pyridyl | phenyl | 2-methylbenzoxazole-5-CO₂Me |
| 62 | H | 3-pyridyl | phenyl | 2-methylbenzoxazole-5-CO₂Me |
| 63 | benzyl ester CH₂ | 3-pyridyl | phenyl | 2-methylbenzoxazole-5-CO₂Et |
| 64 | H | 3-pyridyl | phenyl | 2-methylbenzoxazole-5-CO₂Et |
| 65 | benzyl ester CH₂ | 3-pyridyl | phenyl | 2-methylbenzoxazole-5-CONH₂ |
| 66 | H | 3-pyridyl | phenyl | 2-methylbenzoxazole-5-CONH₂ |
| 67 | benzyl ester CH₂ | 3-pyridyl | phenyl | 2-methylbenzoxazole-5-CONHEt |
| 68 | H | 3-pyridyl | phenyl | 2-methylbenzoxazole-5-CONHEt |
| 69 | benzyl ester CH₂ | 3-pyridyl | phenyl | 2-methylbenzoxazole-5-CONEt₂ |

TABLE 8
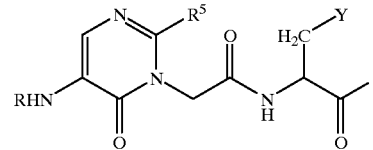
| Example No. | R | R⁵ | Y | Z |
|---|---|---|---|---|
| 70 | H | 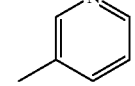 | 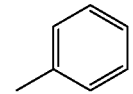 | 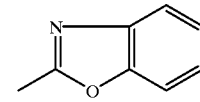 |
| 71 | 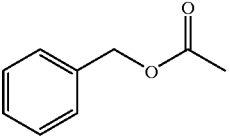 | 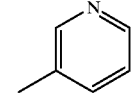 | 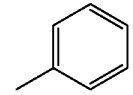 | 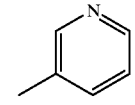 |
| 72 | H | 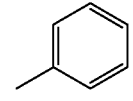 | 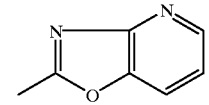 | 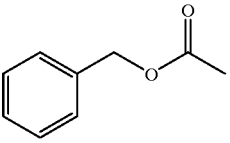 |
| 73 | 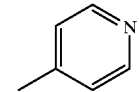 | 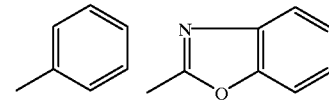 | 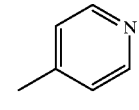 | 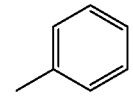 |
| 74 | H | 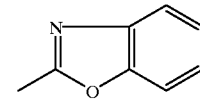 | 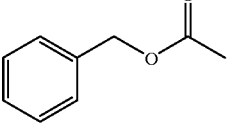 | 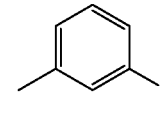 |
| 75 | 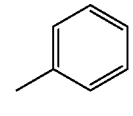 | 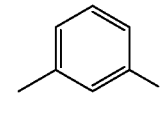 | 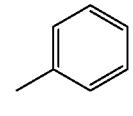 | 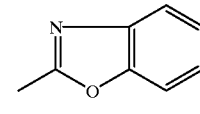 |
| 76 | H | 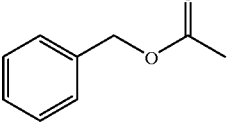 | 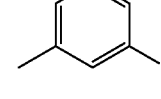 | 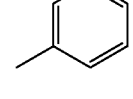 |
| 77 | 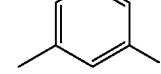 | 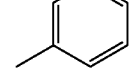 | 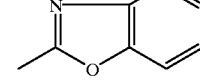 | |
| 78 | H | | | |

TABLE 8-continued
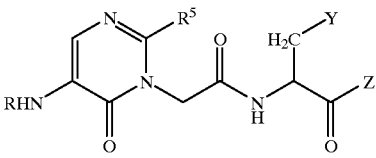
| Example No. | R | R[5] | Y | Z |
|---|---|---|---|---|
| 79 | 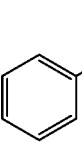 | 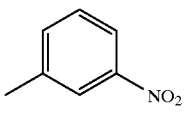 | 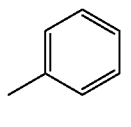 | 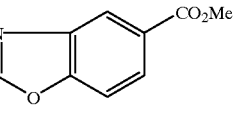 |
| 80 | H | 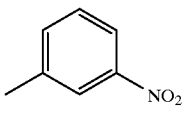 | 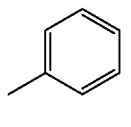 | 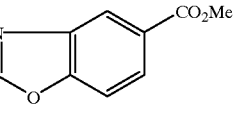 |
| 81 | 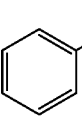 | 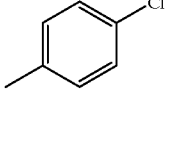 | 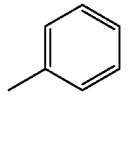 | 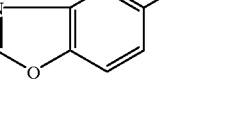 |
| 82 | H | 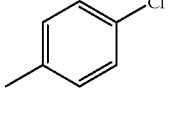 | 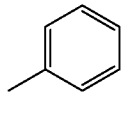 | 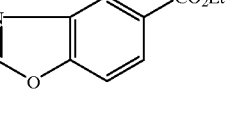 |
| 83 | 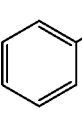 | 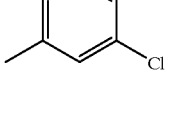 | 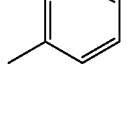 | 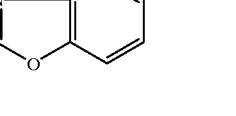 |
| 84 | H | 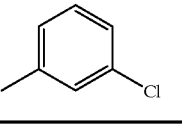 | 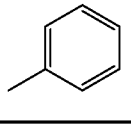 | 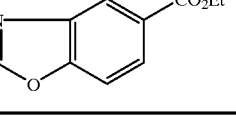 |
TABLE 9
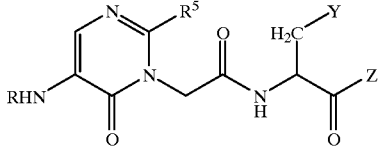
| Example No. | R | R[5] | Y | Z |
|---|---|---|---|---|
| 85 | 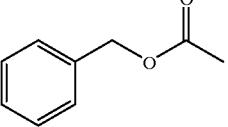 | 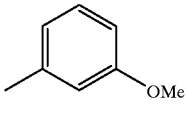 | 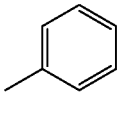 | 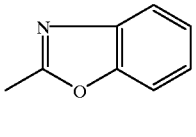 |

TABLE 9-continued
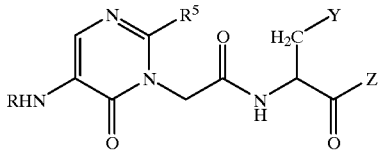
| Example No. | R | R⁵ | Y | Z |
|---|---|---|---|---|
| 86 | H | 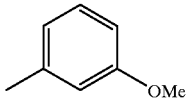 | 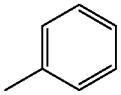 | 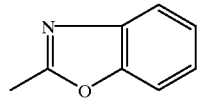 |
| 87 | 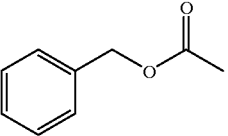 | 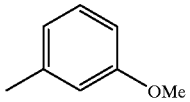 | 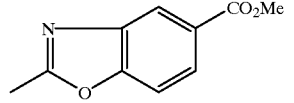 | 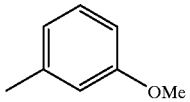 |
| 88 | H | 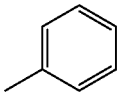 | 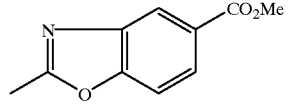 | 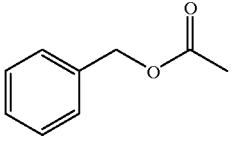 |
| 89 | 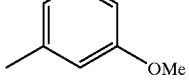 | 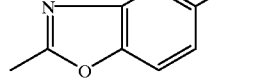 | 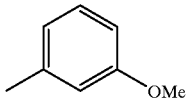 | 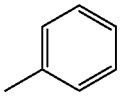 |
| 90 | H | 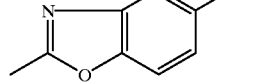 | 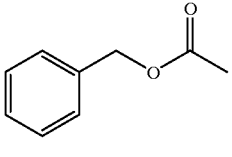 | 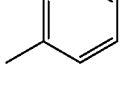 |
| 91 | 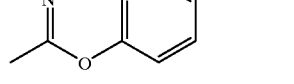 | 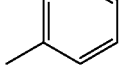 | 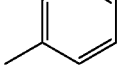 | 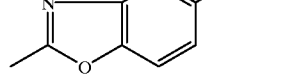 |
| 92 | H | 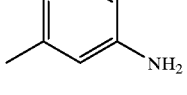 | 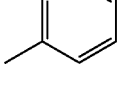 | 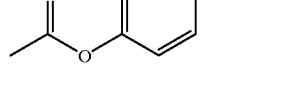 |
| 93 | H | 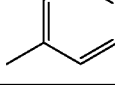 | 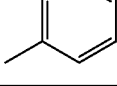 | 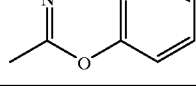 |
| 94 |  |  |  |  |

The spectrum data of the representative compounds from the compounds obtained in the above-mentioned Examples are shown in the following.

Compound of Example 26
2-[5-amino-2-(4-fluorophenyl)-6-oxo-1,6-dihydro-1-pyrimidinyl]-N-[1-[(5-fluorobenzoxazol-2-yl)carbonyl]-2-phenylethyl]acetamide mp 222–227° C. $^1$H-NMR (500 MHz, DMSO-d$_6$) δ8.95 (d, J=6.8 Hz, 1H), 7.98 (dd, J=9.2, 4.3 Hz, 1H), 7.91 (dd, J=8.4, 2.5 Hz, 1H), 7.55 (dt, J=2.5, 9.2 Hz, 1H), 7.35 (dd, J=8.7, 5.6 Hz, 2H), 7.29–7.18 (m, 6H), 7.10 (t, J=8.7 Hz, 2H), 5.50 (m, 1H, 5.15 (s, (2H), 4.48 (d, J=16.7 Hz, 1H), 4.40 (d, J=16.7 Hz, 1H), 3.30 (dd, J=14.1, 4.7 Hz, 1H), 2.96 (dd, J =14.1, 8.9 Hz, 1H)

IR (KBr) 3330, 3020, 1710, 1655, 1605, 1525, 1505 cm$^{-1}$
MS (SIMS, positive) m/z 530 (MH$^+$)

Compound of Example 28
2-[5-amino-2-(4-fluorophenyl)-6-oxo-1,6-dihydro-1-pyrimidinyl]-N-[1-[[5-(ethoxycarbonyl)benzoxazol-2-yl)carbonyl]-2-phenylethyl]acetamide mp 231–234° C. $^1$H-NMR (300 MHz, DMSO-d$_6$) δ8.98 (d, J=6.5 Hz, 1H), 8.51 (d, J=1.4 Hz, 1H), 8.24 (dd, J=8.7, 1.6 Hz, 1H), 8.05 (d, J=8.7 Hz, 1H), 7.40–7.00 (m, 10H), 5.50 (m, 1H), 5.14 (s, 2H), 4.56–4.31 (m, 4H), 3.30 (m, 1H), 2.96 (m, 1H), 1.37 (t, J=7.1 Hz, 3H).

IR (KBr) 3300, 1710, 1655, 1600, 1500 cm$^{-1}$
MS (SIMS, positive) m/z 584 (MH$^+$)

Compound of Example 30
2-[5-amino-2-(4-fluorophenyl)-6-oxo-1,6-dihydro-1-pyrimidinyl]-N-[1-[(5-carbamoylbenzoxazol-2-yl)carbonyl]-2-phenylethyl]acetamide mp 270° C. $^1$H-NMR (300 MHz, DMSO-d$_6$) δ8.96 (d, J=6.8 Hz, 1H), 8.51 (s, 1H), 8.24–8.11 (m, 2H), 7.98 (d, J=8.7 Hz, 1H), 7.56 (brs, 1H), 7.35 (dd, J=8.4, 5.6 Hz, 2H), 7.30–7.15 (m, 7H), 7.10 (t, J=8.7 Hz, 2H), 5.53 (m, 1H, 5.14 (s, 2H), 4.58–4.30 (m, 2H), 3.30 (m, 1H), 2.96 (m, 1H).

IR (KBr) 3350, 1650, 1600 cm$^{-1}$

Compound of Example 31
2-[5-benzyloxycarbonylamino-2-(4-fluorophenyl)-6-oxo-1,6-dihydro-1-pyrimidinyl]-N-[1-[[5-(dimethylaminocarbonyl)benzoxazol-2yl)carbonyl]-2-phenylethyl]acetamide mp 222–226° C. $^1$H-NMR (300 MHz, DMSO-d$_6$) δ9.00 (d, J=6.8 Hz, 1H), 8.88 (s, 1H), 8.41 (s, 1H), 8.05 (s, 1H), 7.96 (d, J=8.6 Hz, 1H), 7.67 (dd, J=8.5, 1.5 Hz, 1H), 7.55–7.02 (m, 14H), 5.57 (m, 1H), 5.17 (s, 2H), 4.54 (d, J=16.4 Hz, 1H), 4.45 (d, J=17.1 hz, 1H), 3.16–2.65 (m, 8H)

IR (KBr) 3350, 1650, 1500 cm$^{-1}$

Compound of Example 32
2-[5-amino-2-(4-fluorophenyl)-6-oxo-1,6-dihydro-1-pyrimidinyl]-N-[1-[[5-(dimethylaminocarbonyl)benzoxazol-2-yl]carbonyl]-2-phenylethyl]acetamide mp 129–133° C. $^1$H-NMR (300 MHz, DMSO-d$_6$) δ8.94 (d, J=6.8 Hz, 1H), 8.05 (d, J=1.2 Hz, 1H), 7.97 (d, J=8.6 Hz, 1H), 7.68 (dd, J=8.5, 1.5 Hz, 1H), 7.48–7.00 (m, 10H), 5.56 (m, 1H), 5.13 (d, J=6.7 Hz, 2H), 4.49 (d, J=16.8 Hz, 1H), 4.41 (d, J=16.7 Hz, 1H), 3.12–2.72 (m, 8H)

IR (KBr) 3350, 1650, 1610, 1500 cm$^{-1}$
MS (SIMS, positive) m/z 583 (MH$^+$)

Compound of Example 34
2-[5-amino-2-(4-fluorophenyl)-6-oxo-1,6-dihydro-1-pyrimidinyl]-N-[1-[[5-(diethylaminocarbonyl)benzoxazol-2yl]carbonyl]-2-phenylethyl]acetamide mp 120–124° C. $^1$H-NMR (300 MHz, DMSO-d$_6$) δ8.94 (d, J=6.8 hz, 1H), 7.98 (s, 1H), 7.97 (d, J=8.8 Hz, 1H), 7.61 (dd, J=8.5, 1.3 hz, 1H), 7.50–6.85 (m, 10H), 5.57 (m, 1H), 5.14 (s, 2H), 4.49 (d, J=16.9 Hz, 1H), 4.42 (d, J=17.2 Hz, 1H), 3.60–2.85 (m, 6H), 1.30–0.90 (m, 6H)

IR (KBr) 3350, 1650, 1600 cm$^{-1}$
MS (SIMS, positive) m/z 611 (MH$^+$)

Compound of Example 36
2-[5-amino-2-(4-fluorophenyl)-6-oxo-1,6-dihydro-1-pyrimidinyl]-N-[1-[(oxazolo[4,5-b]pyridin-2-yl)carbonyl]-2-phenylethyl]acetamide mp 222–225° C. $^1$H-NMR (500 MHz, DMSO-d$_6$) δ9.01 (d, J=6.7 Hz, 1H), 8.76 (dd, J=4.7, 1.1 Hz, 1H), 8.42 (dd, J=8.3, 1.1 Hz, 1H), 7.70 (dd, J=8.3, 4.7 Hz, 1H), 7.35 (dd, J=8.7, 5.6 Hz, 2H), 7.29–7.19 (m, 6H), 7.09 (t, J=8.7 Hz, 2H), 5.48 (m, 1H), 5.14 (s, 2H), 4.48 (d, J=16.8 Hz, 1H), 4.40 (d, J=16.8 Hz, 1H), 3.34 (m, 1H), 2.98 (dd, J=14.1, 8.9 Hz, 1H).

IR (KBr) 3390, 1715, 1655, 1605, 1530, 1505 cm$^{-1}$
MS (SIMS, positive) m/z 513 (MH$^+$)

Compond of Example 38
2-[5-amino-2-(4-fluorophenyl)-6-oxo-1,6-dihydro-1-pyrimidinyl]-N-[1-[(benzothioazol-2-yl)carbonyl]-2-phenylethyl]acetamide mp 196–200° C. $^1$H-NMR (500 MHz, DMSO-d$_6$) δ8.90 (d, J=7.2 Hz, 1H), 8.28 (m, 2H), 7.68 (m, 2H), 7.35 (dd, J=8.6, 5.5 Hz, 2H), 7.29–7.18 (m, 6H), 7.10 (t, J=8.6 Hz, 2H), 5.75 (m, 1H), 5.16 (s, 2H), 4.52 (d, J=16.5 Hz, 1H), 4.40 (d, J=16.5 Hz, 1H), 3.27 (dd, J=14.0, 4.5 Hz, 1H), 2.97 (dd, J=14.0, 9.0 Hz, 1H).

IR (KBr) 3400, 3290, 3050, 1655, 1605, 1555, 1505 cm$^{-1}$
MS (SIMS, positive) m/z 528 (MH$^+$)

Compound of Example 40
2-[5-amino-2-(4-fluorophenyl)-6-oxo-1,6-dihydro-1-pyrimidinyl]-N-[1-[(benzoxazol-2-yl)carbonyl]-2-(4-fluorophenyl)ethyl]acetamide mp 245–249° C. $^1$H-NMR (300 MHz, DMSO-d$_6$) δ8.94 (d, J=7.0 Hz, 1H), 8.01 (d, J=7.9 Hz, 1H), 7.92 (d, J=8.2 Hz, 1H), 7.67 (t, J=7.52 Hz, 1H), 7.56 (t, J=7.4 Hz, 1H), 7.35 (dd, J=8.5, 5.5 Hz, 2H), 7.28 (s, 1H), 7.25 (dd, J=8.4, 5.6 Hz, 2H), 7.08 (t, J=8.8 Hz, 4H), 5.51 (m, 1H), 5.15 (s, 2H), 4.48 (d, J=16.9 Hz, 1H), 4.39 (d, J=16.5 Hz, 1H), 3.29 (dd, J=14.1, 4.8 Hz, 1H), 2.95 (dd, J=14.0, 9.1 Hz, 1H)

IR (KBr) 3350, 1650, 1600, 1500 cm$^{-1}$
MS (SIMS, positive) m/z 530 (MH$^+$).

Compound of Example 45
2-(5-benzyloxycarbonylamino-6-oxo-2-phenyl-1,6-dihydro-1-pyrimidinyl)-N-[1-[(oxazolo[4,5-b]pyridin-2-yl)carbonyl]-2-phenylethyl]acetamide mp 220–223° C. $^1$H-NMR (300 MHz, DMSO-d$_6$) δ9.04 (d, J=6.7 Hz, 1H), 8.84 (s, 1H), 8.76 (dd, J=4.7, 1.4 Hz, 1H), 8.44–8.38 (m, 2H), 7.69 (dd, J=8.3, 4.7 Hz, 1H), 7.46–7.14 (m, 15H), 5.49 (m, 1H), 5.18 (s, 2H), 4.51 (d, J=16.6 Hz, 1H), 4.44 (d, J=16.6 Hz, 1H), 3.34 (dd, J=14.0, 5.0 Hz, 1H), 2.98 (dd, J=14.0, 8.8 Hz, 1H)

IR (KBr) 3350, 1720, 1655, 1600, 1510 cm$^{-1}$
MS (SIMS, positive) m/z 629 (MH$^+$)

Compound of Example 46
2-(5-amino-6-oxo-2-phenyl-1,6-dihydro-1-pyrimidinyl)-N-[1-[(oxazolo[4,5-b]pyridin-2-yl)carbonyl]-2-phenylethyl]acetamide $^1$H-NMR (300 MHz, DMSO-d$_6$) δ8.98 (d, J=6.6 Hz, 1H), 8.76 (dd, J=4.7, 1.2 Hz, 1H), 8.42 (dd, J=8.3, 1.2 Hz, 1H), 7.70 (dd, J=8.3, 4.7 Hz, 1H), 7.39–7.17 (m, 11H), 5.48 (m, 1H), 5.11 (s, 2H), 4.47 (d, J=16.6 Hz, 1H), 4.40 (d, J=16.6 Hz, 1H), 3.32 (m, 1H), 2.99 (m, 2H), 2.99 (dd, J=14.0, 8.8 Hz, 1H)

IR (KBr) 3380, 1715, 1655, 1610, 1530 cm$^{-1}$
MS (SIMS, positive) m/z 495 (MH$^+$)

Compound of Example 50
2-[5-amino-6-oxo-2-(m-tolyl)-1,6-dihydro-1-pyrimidinyl]-N-[1-[[5-(methoxycarbonyl)benzoxazol-2yl]carbonyl]-2-phenylethyl]acetamide mp 185–188° C. ¹H-NMR (500 MHz, DMSO-d₆) δ8.95 (d, J=6.5 Hz, 1H), 8.51 (d, J=0.7 Hz, 1H), 8.23 (dd, J=8.7, 0.8 Hz, 1H), 8.05 (d, J=8.7 Hz, 1H), 7.30–7.06 (m, 10H), 5.53 (m, 1H), 5.10 (s, 2H), 4.46 (s, 2H), 3.93 (s, 3H), 3.30 (dd, J=14.0, 5.0 Hz, 1H), 2.99 (dd, J=14.0, 8.5 Hz, 1H), 2.28 (s, 3H)

IR (KBr) 3250, 3000, 2925, 1710, 1655, 1605, 1515 cm⁻¹
MS (SIMS, positive) m/z 566 (MH⁺)

Compound of Example 52
2-[5-amino-6-oxo-2-(m-tolyl)-1,6-dihydro-1-pyrimidinyl]-N-[1-[[5-(ethoxycarbonyl)benzoxazol-2yl]carbonyl]-2-phenylethyl]acetamide mp 197–199° C. ¹H-NMR (300 MHz, DMSO-d₆) δ8.94 (d, J=6.5 Hz, 1H), 8.51 (s, 1H), 8.23 (dd, J=8.7, 1.7 hz, 1H), 8.04 (d, J=8.7 Hz, 1H), 7.35–7.00 (m, 10H), 5.51 (m, 1H), 5.09 (brs, 2H), 4.46 (s, 2H), 4.39 (q, J=7.1 Hz, 2H), 3.30 (m, 1H), 2.98 (m, 1H), 2.27 (s, 3H), 1.37 (t, J=7.1 Hz, 3H)

IR (KBr) 3350, 1710, 1655, 1610 cm⁻¹
MS (SIMS, positive) m/z 580 (MH⁺)

Compound of Example 53
2-[5-benzyloxycarbonylamino-6-oxo-2-(m-tolyl)-1,6-dihydro-1-pyrimidinyl]-N-[1-[(5-carbamoylbenzoxazol-2-yl)carbonyl]-2-phenylethyl]acetamide mp 200–208° C ¹H-NMR (300 MHz, DMSO-d₆) δ8.99 (d, J=6.6 hz, 1H), 8.86 (s, 1H), 8.50 (d, J=1.3 Hz, 1H), 8.40 (s, 1H), 8.17 (dd, J=8.8, 1.6 hz, 1H), 7.97 (d, J=8.7 Hz, 1H), 7.57 (brs, 1H), 7.50–7.05 (m, 15H), 5.53 (m, 1H), 5.17 (s, 2H), 4.50 (brs, 2H), 3.30 (m, 1H), 2.97 (m, 1H), 2.29 (s, 3H)

IR (KBr) 3250, 1655, 1510 cm⁻¹

Compound of Example 54
2-[5-amino-6-oxo-2-(m-tolyl)-1,6-dihydro-1-pyrimidinyl]-N-[1-[(5-carbamoylbenzoxazol-2-yl)carbonyl]-2-phenylethyl]acetamide mp 262–264° C. ¹H-NMR (300 MHz, DMSO-d₆) δ8.93 (d, J=6.7 Hz, 1H), 8.50 (d, J=1.3 Hz, 1H), 8.17 (dd, J=8.8, 1.6 Hz, 1H), 7.97 (d, J=8.8 Hz, 1H), 7.57 (brs, 1H), 7.34–7.00 (m, 11H), 5.53 (m, 1H), 5.10 (brs, 2H), 4.46 (brs, 2H), 3.30 (m, 1H), 2.98 (m, 1H), 2.27 (s, 3H), IR (KBr) 3350, 1650 cm⁻¹
MS (SIMS, positive) m/z 551 (MH⁺)

Compound of Example 55
2-[5-benzyloxycarbonylamino-6-oxo-2-(m-tolyl)-1,6-dihydro-1-pyrimidinyl]-N-[1-[[5-(ethylaminocarbonyl)benzoxazol-2-yl]carbonyl]-2-phenylethyl]acetamide mp 207–214° C. ¹H-NMR (300 MHz, DMSO-d₆) δ8.99 (d, J=8.7 hz, 1H), 8.86 (brs, 1H), 8.67 (brs, 1H), 8.45 (d, J=1.3 Hz, 1H), 8.40 (s, 1H), 8.14 (dd, J=8.7, 1.7 Hz, 1H), 7.98 (d, J=8.7 Hz, 1H), 7.55–7.08 (m, 14H), 5.54 (m, 1H), 5.17 (s, 2H), 4.50 (brs, 2H), 3.30 (m, 1H), 2.97 (m, 1H), 2.29 (s, 3H), 1.16 (t, J=7.2 Hz, 3H)

IR (KBr) 3350, 1655, 1510 cm⁻¹

Compound of Example 56
2-[5-amino-6-oxo-2-(m-tolyl)-1,6-dihydro-1-pyrimidinyl]-N-[1-[[5-(ethylaminocarbonyl)benzoxazol-2-yl]carbonyl]-2-phenylethyl]acetamide mp 212–214° C. ¹H-NMR (300 MHz, DMSO-d₆) δ8.93 (d, J=6.8 Hz, 1H), 8.67 (brs, 1H), 8.46 (s, 1H), 8.14 (d, J=8.8 Hz, 1H), 7.98 (d, J=8.8 Hz, 1H), 7.48–7.02 (m, 10H), 5.53 (m, 1H), 5.10 (s, 2H), 4.46 (brs, 2H), 3.35 (q, J=7.2 Hz, 2H), 3.30 (m, 1H), 2.97 (m, 1H), 2.27 (s, 3H), 1.16 (t, J=7.1 Hz, 3H)

IR (KBr) 3350, 1640, 1605, 1510 cm⁻¹
MS (SIMS, positive) m/z 579 (MH⁺)

Compound of Example 57
2-[5-benzyloxycarbonylamino-6-oxo-2-(m-tolyl)-1,6-dihydro-1-pyrimidinyl]-N-[1-[[5-(diethylaminocarbonyl)benzoxazol-2-yl]carbonyl]-2-phenylethyl]acetamide mp 95–100° C. ¹H-NMR (300 MHz, DMSO-d₆) δ8.99 (d, J=6.5 Hz, 1H), 8.86 (brs, 1H), 8.41 (s, 1H), 7.97 (s, 1H), 7.96 (d, J=8.0 Hz, 1H), 7.61 (dd, J=8.7, 1.4 Hz, 1H), 7.50–6.95 (m, 14H), 5.55 (m, 1H), 5.17 (s, 2H), 4.50 (brs, 2H), 3.60–2.82 (m, 6H), 2.30 (s, 3H), 1.30–0.80 (m, 6H)

IR (KBr) 3350, 1720, 1650, 1505 cm⁻¹

Compound of Example 58
2-[5-amino-6-oxo-2-(m-tolyl)-1,6-dihydro-1-pyrimidinyl]-N-[1-[[5-(diethylaminocarbonyl)benzoxazol-2-yl]carbonyl]-2-phenylethyl]acetamide mp 117–120° C. ¹H-NMR (300 MHz, DMSO-d₆) δ8.92 (d, J=6.6 Hz, 1H), 7.97 (s, 1H), 7.96 (d, J=7.2 Hz, 1H), 7.61 (dd, J=8.6, 1.3 Hz, 1H), 7.40–6.92 (m, 10H), 5.54 (m, 1H), 5.10 (s, 2H), 4.46 (brs, 2H), 3.60–2.90 (m, 6H), 2.28 (s, 3H), 1.30–0.90 (m, 6H)

IR (KBr) 3400, 1610, 1520 cm⁻¹
MS (SIMS, positive) m/z 607 (MH⁺)

Compound of Example 59
2-[5-benzyloxycarbonylamino-6-oxo-2-(m, tolyl)-1,6-dihydro-1-pyrimidinyl]-N-[1-[(oxazolo[4,5-b]pyridin-2-yl)carbonyl]-2-phenylethyl]acetamide mp 223–227° C. ¹H-NMR (300 MHz, DMSO-d₆) δ9.03 (d, J=6.6 hz, 1H), 8.83 (s, 1H), 8.76 (dd, J=4.7, 1.4 Hz, 1H), 8.43–8.38 (m, 2H), 7.69 (dd, J=8.4, 4.7 Hz, 1H), 7.47–7.12 (m, 14H), 5.51 (m, 1H), 5.17 (s, 2H), 4.50 (s, 2H), 3.33 (dd, J=14.1, 4.9 Hz, 1H), 2.99 (dd, J=14.1, 8.7 Hz, 1H), 2.29 (s, 3H)

IR (KBr) 3360, 3010, 1720, 1655, 1600, 1505 cm⁻¹
MS (SIMS, positive) m/z 643 (MH⁺)

Compound of Example 60
2-[5-amino-6-oxo-2-(m-tolyl)-1,6-dihydro-1-pyrimidinyl]-N-[1-[)oxazolo[4,5-b]pyridin-2-yl)carbonyl]-2-phenylethyl]acetamide ¹H-NMR (300 MHz, DMSO-d₆0 δ8.97 (d, J=6.5 Hz, 1H), 8.76 (dd, J=4.7, 1.4 Hz, 1H), 8.42 (dd, J=8.4, 1.4 Hz, 1H), 7.70 (dd, J=8.4, 4.7 Hz, 1H), 7.29–7.04 (m, 10H), 5.50 (m, 1H), 5.09 (s, 2H), 4.45 (s, 2H), 3.30 (m, 1H), 2.99 (dd, J=14.1, 8.8 Hz, 1H), 2.27 (s, 3H)

IR (KBr) 3260, 1715, 1655, 1605, 1525 cm⁻¹
MS (SIMS, positive) m/z 509 (MH⁺)

Compound of Example 62
2-[5-amino-6oxo-2-(3-pyridyl)-1,6-dihydro-1-pyrimidinyl]-N-[1-[[5-(methoxycarbonyl)benzoxazol-2-yl]carbonyl]-2-phenylethyl]acetamide mp 141–147° C. ¹H-NMR (500 MHz, DMSO-d₆) δ9.00 (d, J=6.7 Hz, 1H), 8.58–8.53 (m, 2H), 8.52 (d, J=1.5 Hz, 1H), 8.23 (dd, J=8.7, 1.7 Hz, 1H), 8.04 (d, J=8.7 Hz, 1H), 7.71 (dt, J=7.9, 1.9 Hz, 1H), 7.35–7.15 (m, 7H), 5.52 (m, 1H), 5.24 (s, 2H), 4.52, 4.48 (ABq, J=16.9 Hz, 2H), 3.93 (s, 3H), 3.32–3.26 (m, 1H), 2.97 (dd, J=14.1, 8.6 Hz, 1H)

IR (KBr) 3275, 3000, 2925, 1710, 1655, 1605, 1525 cm⁻¹
MS (SIMS, positive) m/z 553 (MH⁺)

Compound of Example 64
2-[5-amino-6-oxo-2-(3-pyridyl)-1,6-dihydro-1-pyrimidinyl]-N-[1-[[5-(ethoxycarbonyl)benzoxazol-2yl]carbonyl]-2-phenylethyl]acetamide mp 148–152° C. ¹H-NMR (500 MHz, DMSO-d₆) δ9.00 (d, J=6.8 Hz, 1H), 8.59–8.50 (m, 3H), 8.23 (dd, J=8.7, 1.6 Hz, 1H), 8.04 (d, J=8.7 Hz, 1H), 7.71 (dt, J=8.0, 1.9 Hz, 1H), 7.25–7.16 (m, 7H), 5.52 (m, 1H), 5.24 (s, 2H), 4.54 (d, J=17.0 Hz, 1H), 4.47 (d, J=17.0 Hz, 1H), 4.39 (q, J=7.1 Hz, 2H), 3.30 (dd, J=14.1, 4.8 Hz, 1H), 2.96 (dd, J=14.1, 8.7 Hz, 1H), 1.38 (t, J=7.1 Hz, 3H)

IR (KBr) 3400, 3300, 1710, 1655, 1605, 1525 cm⁻¹
MS (SIMS, positive) m/z 567 (MH⁺)

Compound of Example 71
2-[5-benzyloxycarbonylamino-6-oxo-2-(3-pyridyl)-1,6-dihydro-1-pyrimidinyl]-N-[1-[(oxazolo[4,5-b]pyridin-2-yl)carbonyl]-2-phenylethyl]acetamide mp 190–195° C. ¹H-NMR (300 MHz, DMSO-d₆) δ9.08 (d, J=6.8 hz, 1H), 8.93 (s, 1H), 8.75 (dd, J=4.7, 1.4 Hz, 1H), 8.63–8.58 (m, 2H), 8.44 (s, 1H), 8.41 (dd, J=8.4, 1.4 Hz, 1H), 7.77 (dt, J=8.0, 1.9 Hz, 1H), 7.69 (dd, J=8.4, 4.7 Hz, 1H), 7.47–7.17 (m, 11H), 5.49 (m, 1H), 5.18 (s, 2H), 4.56 (d, J=16.9 Hz, 1H), 4.49 (d, J=16.9 Hz, 1H), 3.33 (m, 1H), 2.97 (dd, J=14.0, 8.7 Hz, 1H)

IR (KBr) 3380, 3280, 1720, 1655, 1600, 1510 cm⁻¹

MS (SIMS, positive) m/z 630 (MH⁺)

Compound of Example 72

2-[5-amino-6-oxo-2-(3-pyridyl)-1,6-dihydro-1-pyrimidinyl]-N-[1-[(oxazolo[4,5-b]pyridin- 2-yl)carbonyl]-2-phenylethyl]acetamide ¹H-NMR (300 MHz, DMSO-d₆) δ9.03 (d, J=6.7 Hz, 1H), 8.76 (dd, J=4.7, 1.4 Hz, 1H), 8.57–8.50 (m, 2H), 8.42 (dd, J=8.4, 1.4 Hz, 1H), 7.72–7.65 (m, 2H), 7.32–7.17 (m, 7H), 5.48 (m, 1H), 5.23 (s, 2H), 4.53 (d, J=16.8 Hz, 1H), 4.45 (d, J=16.8 Hz, 1H), 3.33 (m, 1H), 2.98 (dd, J=14.0, 8.6 Hz, 1H)

IR (KBr) 3350, 1710, 1655, 1605, 1525 cm⁻¹

MS (SIMS, positive) m/z 496 (MH⁺)

Compound of Example 73

2-[5-benzyloxycarbonylamino-6-oxo-2-(4-pyridyl)-1,6-dihydro-1-pyrimidinyl]-N-[1-[[5-(methoxycarbonyl)benzoxazol-2-yl]carbonyl]-2-phenylethyl]acetamide ¹H-NMR (300 MHz, DMSO-d₆) δ9.05 (d, J=6.8 Hz, 1H), 8.96 (s, 1H), 8.61 (dd, J=4.5, 1.5 Hz, 2H), 8.53 (d, J=1.5 hz, 1H), 8.44 (s, 1H), 8.23 (dd, J=8.7, 1.6 Hz, 1H), 8.04 (d, J=8.7 Hz, 1H), 7.48–7.14 (m, 12H), 5.56 (m, 1H), 5.18 (s, 2H), 4.50 (m, 2H), 3.92 (s, 3H), 3.38–3.23 (m, 1H), 2.96 (dd, J=14.1, 8.8 Hz, 1H)

IR (KBr) 3275, 3025, 2925, 1720, 1660, 1595, 1510 cm⁻¹

MS (SIMS, positive) m/z 687 (MH⁺)

Compound of Example 74

2-[5-amino-6-oxo-2-(4-pyridyl)-1,6-dihydro-1-pyrimidinyl]-N-[1-[[5-(methoxycarbonyl)benzoxazol-2-yl]carbonyl]-2-phenylethyl]acetamide mp 238–240° C. ¹H-NMR (500 MHz, DMSO-d₆) δ9.02 (d, J=6.7 Hz, 1H), 8.57–8.50 (m, 3H), 8.24 (dd, J=8.7, 1.6 Hz, 1H), 8.05 (d, J=8.7 hz, 1H), 7.35–7.18 (m, 8H), 5.56 (m, 1H), 5.31 (brs, 2H), 4.48 (m, 2H), 3.93 (s, 3H), 3.38–3.29 (m, 1H), 2.97 (dd, J=14.1, 8.7 Hz, 1H)

IR (KBr) 3275, 3025, 2950, 1710, 1655, 1610, 1590, 1530 cm⁻¹

Ms (SIMS, positive) m/z 553 (MH⁺)

Compound of Example 76

2-[5-amino-2-(3-fluorophenyl)-6-oxo-1,6-dihydro-1-pyrimidinyl]-N-[1-[[5-(methoxycarbonyl)benzoxazol-2-yl]carbonyl]-2-phenylethyl]acetamide mp 194.5–196° C.

¹H—NMR (300 MHz, DMSO-d₆) δ 8.99 (d, J=6.7 Hz, 1H), 8.51 (d, J=1.6 Hz, 1H), 8.23 (dd, J=8.7, 1.6 Hz, 1H), 8.04 (d, J=8.7 Hz, 1H), 7.40–7.11 (m, 10H), 5.53 (m, 1H), 5.19 (brs, 2H), 4.52 (d, J=17.2 Hz, 1H), 4.46 (d, J=17.2 Hz, 1H), 3.93 (s, 3H), 3.31 (dd, J=14.0, 4.7 Hz, 1H), 2.98 (dd, J=14.0, 8.8 Hz, 1H)

IR (KBr) 3450, 3350, 3080, 2960, 1720, 1675, 1660, 1610, 1585, 1530 cm⁻¹

MS (APCI, positive) m/z 570 (MH⁺)

COMPOUND OF EXAMPLE 78

2-[5-amino-2-(3-chlorophenyl)-6-oxo-1,6-dihydro-1-pyrimidinyl]-N-[1-[[5- (methoxycarbonyl)benzoxazol-2-yl]carbonyl]-2-phenylethyl]acetamide mp 197–199° C.

¹H—NMR (300 MHz, DMSO-d₆) δ 9.00 (d, J=6.8 Hz, 1H), 8.51 (d, J=1.6 Hz, 1H), 8.23 (dd, J=8.7, 1.6 Hz, 1H), 8.04 (d, J=8.7 Hz, 1H), 7.48–7.16 (m, 10H), 5.53 (m, 1H), 5.21 (brs, 2H), 4.53 (d, J=16.8 Hz, 1H), 4.45 (d, J=16.8 Hz, 1H), 3.93 (s, 3H), 3.30 (dd, J=14.1, 4.9 Hz, 1H), 2.99 (dd, J=14.1, 8.7 Hz, 1H)

IR (KBr) 3420, 3280, 3080, 3020, 2950, 1720, 1675, 1660, 1610, 1565, 1530 cm⁻¹

MS (APCI, positive) m/z 586 (MH⁺)

COMPOUND OF EXAMPLE 80

2-[5-amino-2-(3-nitrophenyl)-6-oxo-1,6-dihydro-1-pyrimidinyl]-N-[1-[[5- (methoxycarbonyl)benzoxazol-2-yl]carbonyl]-2-phenylethyl]acetamide mp 202–203.5° C.

¹H—NMR (300 MHz, DMSO-d₆) δ 9.00 (d, J=6.9 Hz, 1H), 8.50 (d, J=1.4 Hz, 1H), 8.22 (dd, J=8.7, 1.4 Hz, 1H), 8.21 (brs, 2H), 8.03 (d, J=8.7 Hz, 1H), 7.78 (d, J=7.8 Hz, 1H), 7.61 (t, J=7.8 Hz, 1H), 7.32 (s, 1H), 7.28–7.13 (m, 5H), 5.53 (m 1H), 5.29 (brs, 2H), 4.57 (d, J=16.5 Hz, 1H), 4.51 (d, J=16.5 Hz, 1H), 3.93 (s, 3H), 3.29 (dd, J=14.0, 4.8 Hz, 1H), 2.94 (dd, J=14.0, 8.7 Hz, 1H)

IR (KBr) 3470, 3350, 3080, 2960, 1720, 1665, 1605, 1530, cm⁻¹

MS (APCI, positive) m/z 597 (MH⁺)

COMPOUND OF EXAMPLE 82

2-[5-amino-2-(4-chlorophenyl)-6-oxo-1,6-dihydro-1-pyrimidinyl]-N-[1-[[5- (ethoxycarbonyl)benzoxazol-2-yl]carbonyl]-2-phenylethyl]acetamide ¹H—NMR (300 MHz, DMSO-d₆) δ 9.02 (d, J=6.7 Hz, 1H), 8.52 (d, J=1.4 Hz, 1H), 8.25 (d, J=8.7, 1.4 Hz, 1H), 8.06 (d, J=8.7 Hz, 1H), 7.31–7.18 (m, 10H), 5.48 (m, 1H), 5.19 (brs, 2H), 4.48 (d, J=16.6 Hz, 1H), 4.39 (d, J=16.6 Hz, 1H), 4.37 (q, J=7.1 Hz, 2H), 3.33 (dd, J=14.0, 4.3 Hz, 1H), 2.97 (dd, J=14.0, 8.9 Hz, 1H), 1.37 (t, J=7.1 Hz, 3H)

IR (KBr) 3380, 3280, 3040, 1715, 1660, 1605, 1550, 1520, cm⁻¹

MS (SIMS, positive) m/z 600 (MH⁺)

COMPOUND OF EXAMPLE 84

2-[5-amino-2-(3-chlorophenyl)-6-oxo-1,6-dihydro-1-pyrimidinyl]-N-[1-[[5- (ethoxycarbonyl)benzoxazol-2-yl]carbonyl]-2-phenylethyl]acetamide mp 235–237° C.

¹H—NMR (300 MHz, DMSO-d₆) δ 8.99 (d, J=6.4 Hz, 1H), 8.51 (d, J=1.5 Hz, 1H), 8.23 (dd, J=8.7, 1.5 Hz, 1H), 8.04 (d, J=8.7 Hz, 1H), 7.46–7.16 (m, 10H), 5.51 (m, 1H), 5.20 (brs, 2H), 4.52 (d, J=16.7 Hz, 1H), 4.45 (d, J=16.7 Hz, 1H), 4.39 (q, J=7.1 Hz, 2H), 3.30 (dd, J=14.0, 5.0 Hz, 1H), 2.98 (dd, J=14.0, 8.6 Hz, 1H), 1.37 (t, J=7.1 Hz, 3H)

IR (KBr) 3400, 3250, 3040, 2960, 1720, 1710, 1675, 1650, 1610, 1585, 1560, 1530 cm⁻¹

MS (APCI, positive) m/z 600 (MH⁺)

COMPOUND OF EXAMPLE 86

2-[5-amino-2-(3-methoxyphenyl)-6-oxo-1,6-dihydro-1-pyrimidinyl]-N-[1- [(benzoxazol-2-yl)carbonyl]-2-phenylethyl]acetamide mp 167–171° C.

¹H—NMR (300 MHz, DMSO-d₆) δ 8.92 (d, J=6.8 Hz, 1H), 8.01 (d, J=8.0 Hz, 1H), 7.91 (d, J=8.0 Hz, 1H),
7.66 (t, J=8.0 Hz, 1H), 7.56 (t, J=8.0 Hz, 1H),
7.30–7.15 (m, 7H), 6.98–6.92 (m, 2H), 6.85 (d, J=7.6 Hz, 1H),
5.57 (m, 1H), 5.13 (brs, 2H), 4.49 (d, J=16.6 Hz, 1H), 4.43 (d, J=16.6 Hz, 1H), 3.68 (s, 3H),
3.27 (dd, J=14.0, 9.0 Hz, 1H), 2.99 (dd, 14.1, 8.6 Hz, 1H)
IR (KBr) 3450, 3300, 3080, 3030, 2970, 1715, 1660, 1605, 1580, 1530 cm$^{-1}$
MS (APCI, positive) m/z 524 (MH$^+$)

COMPOUND OF EXAMPLE 88

2-[5-amino-2-(3-methoxyphenyl)-6-oxo-1,6-dihydro-1-pyrimidinyl]-N-[1-[[5-(methoxycarbonyl)benzoxazol-2-yl]carbonyl]-2-phenylethyl]acetamide mp 184.5–186.0° C.
$^1$H—NMR (300 MHz, DMSO-d$_6$) δ 8.97 (d, J=6.7 Hz, 1H),
8.51 (d, J=1.6 Hz, 1H), 8.23 (dd, J=8.7, 1.6 Hz, 1H),
8.04 (d, J=8.7 Hz, 1H), 7.31–7.14 (m, 7H), 6.98–6.83 (m, 3H),
5.54 (m, 1H), 5.13 (brs, 2H), 4.50 (d, J=16.6 Hz, 1H), 4.44 (d, J=16.6 Hz, 1H), 3.93 (s, 3H), 3.69 (s, 3H),
3.30 (dd, J=14.2, 5.3 Hz, 1H), 3.00 (dd, J=14.2, 8.4 Hz, 1H)
IR (KBr) 3450, 3320, 3060, 3020, 2940, 1715, 1660, 1605, 1530 cm$^{-1}$
MS (APCI, positive) m/z 582 (MH$^+$)

COMPOUND OF EXAMPLE 90

2-[5-amino-2-(3-methoxyphenyl)-6-oxo-1,6-dihydro-1-pyrimidinyl]-N-[1-[[5-(ethoxycarbonyl)benzoxazol-2-yl]carbonyl]-2-phenylethyl]acetamide mp 153–156° C.
$^1$H—NMR (300 MHz, DMSO-d$_6$) δ 8.96 (d, J=6.9 Hz, 1H),
8.51 (d, J=1.6 Hz, 1H), 8.23 (dd, J=8.7, 1.6 Hz, 1H),
8.04 (d, J=8.7 Hz, 1H), 7.30–7.15 (m, 7H), 6.97–6.90 (m, 2H),
6.86 (d, J=7.6 Hz, 1H), 5.53 (m, 1H), 5.12 (brs, 2H),
4.49 (d, J=16.6 Hz, 1H), 4.44 (d, J=16.6 Hz, 1H),
4.39 (q, J=7.1 Hz, 2H), 3.69 (s, 3H), 3.30 (dd, J=14.2, 4.8 Hz, 1H), 2.99 (dd, J=14.1, 8.6 Hz, 1H), 1.37 (t, J=7.0 Hz, 3H)
IR (KBr) 3450, 3250, 3050, 2950, 1720, 1660, 1600, 1580, 1530 cm$^{-1}$
MS (APCI, positive) m/z 596 (MH$^+$)

COMPOUND OF EXAMPLE 92

2-(5-amino-6-oxo-2-phenyl-1,6-dihydro-1-pyrimidinyl)-N-[1-[[5-(methoxycarbonyl)benzoxazol-2-yl]carbonyl]-2-phenylethyl]acetamide mp 271–274° C.
$^1$H—NMR (300 MHz, DMSO-d$_6$) δ 8.95 (d, J=6.6 Hz, 1H),
8.51 (d, J=1.5 Hz, 1H), 8.24 (dd, J=8.7, 1.5 Hz, 1H),
8.05 (d, J=8.7 Hz, 1H), 7.41–7.16 (m, 11H), 5.53 (m, 1H),
5.11 (brs, 2H), 4.49 (d, J=16.7 Hz, 1H), 4.42 (d, J=16.7 Hz, 1H),
3.93 (s, 3H), 3.31 (dd, J=14.0, 4.9 Hz, 1H),
2.98 (dd, J=14.0, 8.7 Hz, 1H)
IR (KBr) 3400, 3280, 3040, 2940, 1715, 1675, 1650, 1610, 1585, 1530 cm$^{-1}$

COMPOUND OF EXAMPLE 93

2-[5-amino-2-(3-aminophenyl)-6-oxo-1,6-dihydro-1-pyrimidinyl]-N-[1-[[5-(methoxycarbonyl)benzoxazol-2-yl]carbonyl]-2-phenylethyl]acetamide mp 125.0–127.5° C.
$^1$H—NMR (300 MHz, DMSO-d$_6$) δ 8.92 (d, J=6.6 Hz, 1H),
8.52 (d, J=1.6 Hz, 1H), 8.23 (dd, J=8.7, 1.6 Hz, 1H),
8.04 (d, J=8.7 Hz, 1H), 7.31–7.13 (m, 6H), 6.87 (t, J=7.6 Hz, 1H),
6.65–6.50 (m, 2H), 6.37 (d, J=7.6 Hz, 1H), 5.56 (m, 1H),
5.25 (brs, 2H), 5.03 (brs, 2H), 4.51 (d, J=16.6 Hz, 1H),
4.44 (d, J=16.6 Hz, 1H), 3.93 (s, 3H),
3.30 (dd, J=14.1, 4.6 Hz, 1H), 3.03 (dd, J=14.1, 8.4 Hz, 1H)
IR (KBr) 3400, 3340, 3050, 3010, 2940, 1715, 1655, 1600, 1530 cm$^{-1}$
MS (APCI, positive) m/z 567 (MH$^+$)

COMPOUND OF EXAMPLE 94

2-[5-acetamide-2-(4-fluorophenyl)-6-oxo-1,6-dihydro-1-pyrimidinyl]-N-[1-[(benzoxazol-2-yl)carbonyl]-2-phenylethyl]acetamide mp 254–256° C.
$^1$H—NMR (300 MHz, DMSO-d$_6$) δ 9.50 (s, 1H), 9.02 (d, J=6.9 Hz, 1H),
8.77 (s, 1H), 8.01 (d, J=8.0 Hz, 1H), 7.92 (d, J=8.0 Hz, 1H),
7.67 (t, J=8.0 Hz, 1H), 7.56 (t, J=8.0 Hz, 1H),
7.43 (dd, J=8.8, 5.5 Hz, 2H), 7.30–7.12 (m, 7H), 5.57 (m, 1H),
4.55 (d, J=16.7 Hz, 1H), 4.45 (d, J=16.7 Hz, 1H),
3.31 (dd, J=14.1, 4.7 Hz, 1H), 2.96 (dd, J=14.1, 8.9 Hz, 1H),
2.13 (s, 3H)
IR (KBr) 3470, 3360, 3080, 1695, 1655, 1605, 1530, 1500 cm$^{-1}$

EXPERIMENTAL EXAMPLE 1

Inhibitory Activity of the Inventive Compound on Human Heart Chymase

The effectiveness of the inhibitory activity of compound (I) and compound (XXVI) of the present invention was evaluated based on the inhibitory activity on amidase activity of human heart chymase, which was determined as in the following.

The inhibitory activity was quantitatively determined through variation in fractional residual activity of the enzyme caused by the inventive compound in defined serial concentration (<×1, <×10, <×100-fold equivalents) relative to 5 nM chymase in the presence of synthetic substrate, succinyl-alanyl-alanyl-prolyl-phenylalanine-p-nitroanilide (final concentration 2.5 mM). The inhibitory effect was analyzed by least square regression of Easson-Stedman plot (Proc. Roy. Soc. B. 1936, 121, p. 141) utilizing bimolecular equilibrium reaction linearization formula. The inhibitory activity was evaluated by the apparent inhibitory constant (Kiapp) obtained by this analysis and inhibitory constant (Ki) calculated from final substrate concentration in the reaction mixture and Km values separately determined. With regard to the quantlitative determination of initial rate of the enzyme reaction, the amount of p-nitroaniline produced by hydrolysis of the substrate was spectrophotometrically detected in terms of an increased absorbance which was obtained by subtracting absorbance at 650 nm wavelength from the absorbance at 405 nm. The chymase inhibitory activity of the compound of the present invention was calculated as ratio of residual activity in the presence of inhibitor relative to enzyme activity in the absence of inhibitor, and incorporation of the determination values was completed at a level less than initial rate guarantee absorbance at a concentration of the substrate used for the enzyme, after which analysis was performed.

The reaction mixture consisted of a buffer (pH 7.5, 140 μl) of Tris-HCl (100 mM) - KCl (2 M), the inventive compound dissolved in 20 µl of 10% dimethyl sulfoxide (DMSO), substrate dissolved in 20 µl of DMSO, and 20 µl of chymase, thus amounting to 200 µl in total.

Starting with the absorbance immediately after addition of the enzyme, increases in absorbance were recorded as a progressive curve taken precisely at equal time intervals.

From the above data, the difference between absorbances at completion of the reaction and immediately after addition was used to quantitatively determine the residual activity of the sample added with the inhibitor relative to a control wherein the inhibitor was not added. Alternatively, reaction rates of the control and the sample added with the inhibitor were calculated for certain time period ($\geqq 20$ min) with successive shift (every 10 to 30 minutes) of the period, and the residual activity ratio was quantitatively determined and analyzed from the respective reaction rates averaged through the entire reaction time.

The inhibitory activity against human leukocyte elastase was determined using N-methoxysuccinyl-alanyl-alanyl-prolyl-valine-p-nitroanilide as a substrate and 0.1 M Tris-HCl (pH 8.0) containing 20 mM $CaCl_2$ and 0.1% Tween 80 as a buffer, wherein other compositions and method were the same as above.

The results of human heart chymase inhibitory activity test of representative compound (I) and compound (XXVI) of the present invention are shown in Table 10.

TABLE 10

| Example No. | Ki (µM) |
| --- | --- |
| 3 | 1.30 |
| 5 | 0.076 |
| 7 | 0.056 |
| 9 | 1.84 |
| 15 | 0.183 |
| 17 | 0.130 |
| 21 | 0.111 |
| 23 | 0.048 |
| 26 | 0.093 |
| 31 | 0.016 |
| 40 | 0.990 |
| 44 | 0.002 |
| 45 | 0.024 |
| 53 | 0.066 |
| 55 | 0.059 |
| 58 | 0.012 |
| 64 | 0.045 |
| 72 | 0.074 |
| 73 | 0.059 |
| 80 | 0.042 |
| 88 | 0.005 |
| 93 | 0.006 |
| 94 | 0.058 |

On the other hand, the inhibitory activity against human leukocyte elastase was >$10^5$ µM for every compound.

From the above results, it is evident that the compound (I) and compound (XXVI) of the present invention does not inhibit human leukocyte elastase at all, but strongly inhibits human heart chymase.

FORMULATION EXAMPLE 1: TABLET

| (1) | Compound (I) of the present invention | 10 mg |
| --- | --- | --- |
| (2) | Fine particle No. 209 for direct pounding (Fuji Kagaku) | 46.6 mg |
| | Magnesium aluminate metasilicate | 20% |

-continued

| | | |
| --- | --- | --- |
| | Corn starch | 30% |
| | Lactose | 50% |
| (3) | Crystalline cellulose | 24.0 mg |
| (4) | Calcium carboxylmethylcellulose | 4.0 mg |
| (5) | Magnesium stearate | 0.4 mg |

(1), (3) and (4) were respectively passed through a 100 mesh sieve in advance. The obtained (1), (3) and (4) and (2) were respectively dried to a certain water content and mixed at the above-mentioned weight ratios in a mixer. (5) was added to the homogeneous powder mixture and mixed for a short time (30 seconds) and the mixed powder was compressed (pounder: 6.3 mmø, 6.0 mmR) to give tablets weighing 85 mg per tablet.

This tablet may be coated with a typical enteric film coating agent (e.g., polyvinyl acetal diethylamino acetate) or edible colorant, as necessary.

FORMULATION EXAMPLE 2: CAPSULE

| (1) Compound (I) of the present invention | 50 g |
| --- | --- |
| (2) Lactose | 935 g |
| (3) Magnesium stearate | 15 g |

The above-mentioned ingredients were weighed respectively and mixed homogeneously. The mixed powder was packed in hard gelatin capsules by 200 mg per capsule.

FORMULATION EXAMPLE 3: INJECTION

| (1) Hydrochloride of compound (I) of the present invention | 5 mg |
| --- | --- |
| (2) Sucrose | 100 mg |
| (3) Physiological saline | 10 ml |

A mixture of the above-mentioned ingredients was filtered through a membrane filter, again sterilized by filtration and the filtrate was aseptically dispensed into vials. Nitrogen gas was filled and the vials were sealed to give intravenous injection.

The heterocyclic amide compound and pharmacologically acceptable salt thereof of the present invention have superior inhibitory activity against chymase groups in mammals inclusive of human and can be administered orally or parenterally. Therefore, they are useful as chymase inhibitors and can be used for the prophylaxis and treatment of various diseases caused by chymase, such as those caused by angiotensin II.

The present invention is based on patent application Nos. 284471/1996 and 194106/1997 filed in Japan, the contents of which are incorporated hereinto by reference.

What is claimed is:

1. A heterocyclic amide compound of the formula (I)

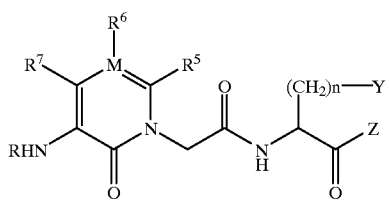
(I)

wherein

R is a hydrogen atom, alkyl, —CHO, —CONH$_2$, —COR$^1$, —COOR$^1$, —CONHOR$^1$, —CONHR$^1$, —CONR$^1$R$^{1'}$, —CONHSO$_2$R$^1$, —COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{1'}$ or —SO$_2$E wherein R$^1$ and R$^{1'}$ may be the same or different and each is independently alkyl, cycloalkyl, cycloalkylalkyl, aryl, arylalkyl, heteroaryl, heteroarylalkyl, heterocycle or heterocyclic alkyl, R$^2$, R$^3$ and R$^4$ may be the same or different and each is independently a hydrogen atom, alkyl or arylalkyl, or —NR$^3$R$^4$ may in combination form a heterocycle, X is a single bond, —NH—, —O— or —S—, W is a single bond, —NH—, —NHCO—, —NHCOO— or —NHCONH—, and E is a hydroxyl group or amino;

R$^5$ and R$^7$ may be the same or different and each is independently hydrogen atom or alkyl, or one of R$^5$ and R$^7$ is aryl, arylalkyl, arylalkenyl, heteroaryl, heteroarylalkyl or heteroarylalkenyl and the rest is hydrogen atom;

M is and R$^6$ is void;

Y is cycloalkyl, aryl or heteroaryl;

Z is a group of the formula (i)

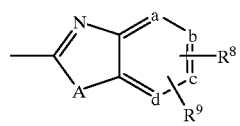
(i)

formula (ii)

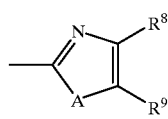
(ii)

formula (iii)

(iii)

wherein R$^8$ and R$^9$ may be the same or different and each is independently hydrogen atom, alkyl, aryl, arylalkyl, heteroaryl, heteroarylalkyl, halogen, trifluoromethyl, cyano, nitro, —NR$^{10}$R$^{10'}$, —NHSO$_2$R$^{10}$, —OR$^{10}$, —COOR$^{10}$, —CONHSO$_2$R$^{10}$ or —CONR$^{10}$R$^{10'}$ wherein R$^{10}$ and R$^{10'}$ may be the same or different and each is independently hydrogen atom, alkyl, cycloalkyl, cycloalkylalkyl, aryl, arylalkyl, heteroaryl, heteroarylalkyl or trifluoromethyl, or —NR$^{10}$R$^{10'}$ may in combination form heterocycle, A is —O—, —S— or —NR$^{12}$— wherein R$^{12}$ is a hydrogen atom, alkyl, cycloalkyl or cycloalkylalkyl, and a, b, c and d are each a carbon atom or one of them is a nitrogen atom and the rest is a carbon atom; and n is 0 or 1, wherein, of the above-mentioned groups, alkyl, cycloalkyl, cycloalkylalkyl, aryl, arylalkyl, arylalkenyl, heteroaryl, heteroarylalkyl, heteroarylalkenyl, heterocycle and heterocyclic alkyl each optionally has a substituent, or a pharmacologically acceptable salt thereof.

2. The heterocyclic amide compound of claim 1, wherein, in the formula (I), Y is an optionally substituted aryl, or a pharmacologically acceptable salt thereof.

3. The heterocyclic amide compound of claim 1, wherein, in the formula (I), Z is a group of the formula (i), or a pharmacologically acceptable salt thereof.

4. The heterocyclic amide compound of claim 1, wherein, in the formula (I), one of R$^5$ and R$^7$ is optionally substituted aryl and the rest is hydrogen atom, and is void, or a pharmacologically acceptable salt thereof.

5. A compound of the formula (II)

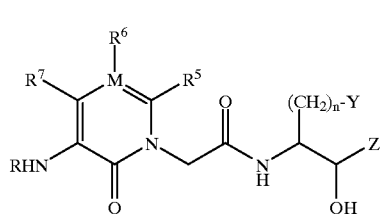
(II)

wherein

R is a hydrogen atom, alkyl, —CHO, —CONH$_2$, —COR$^1$, —COOR$^1$, —CONHOR$^1$, —CONHR$^1$, —CONR$^1$R$^{1'}$, —CONHSO$_2$R$^1$, —COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{1'}$ or —SO$_2$E wherein R$^1$ and R$^{1'}$ may be the same or different and each is independently alkyl, cycloalkyl, cycloalkylalkyl, aryl, arylalkyl, heteroaryl, heteroarylalkyl, heterocycle or heterocyclic alkyl, R$^2$, R$^3$ and R$^4$ may be the same or different and each is independently a hydrogen atom, alkyl or arylalkyl, or —NR$^3$R$^4$ may in combination form a heterocycle, X is a single bond, —NH—, —O— or —S—, W is a single bond, —NH—, —NHCO—, —NHCOO— or —NHCONH—, and E is a hydroxyl group or amino;

R$^5$ and R$^7$ may be the same or different and each is independently hydrogen atom or alkyl, or one of R$^5$ and R$^7$ is aryl, arylalkyl, arylalkenyl, heteroaryl, heteroarylalkyl or heteroarylalkenyl and the rest is hydrogen atom;

M is and nitrogen atom, R$^6$ is void;

Y is cycloalkyl, aryl or heteroaryl;

Z is a group of the formula (i)

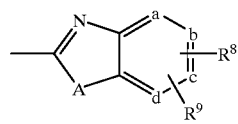

formula (ii)

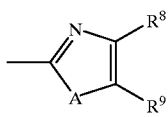

or formula (iii)

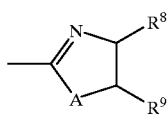

wherein $R^8$ and $R^9$ may be the same or different and each is independently hydrogen atom, alkyl, aryl, arylalkyl, heteroaryl, heteroarylalkyl, halogen, trifluoromethyl, cyano, nitro, —$NR^{10}R^{10'}$, —$NHSO_2R^{10}$, —$OR^{10}$, —$COOR^{10}$, —$CONHSO_2R^{10}$ or —$CONR^{10}R^{10'}$ wherein $R^{10}$ and $R^{10'}$ may be the same or different and each is independently hydrogen atom, alkyl, cycloalkyl, cycloalkylalkyl, aryl, arylalkyl, heteroaryl, heteroarylalkyl or trifluoromethyl, or —$NR^{10}R^{10'}$ may in combination form heterocycle, A is —O—, —S— or —$NR^{12}$— wherein $R^{12}$ is a hydrogen atom, alkyl, cycloalkyl or cycloalkylalkyl, and a, b, c and d are each a carbon atom or one of them is a nitrogen atom and the rest is a carbon atom; and n is 0 or 1, wherein, of the above-mentioned groups, alkyl, cycloalkyl, cycloalkylalkyl, aryl, arylalkyl, arylalkenyl, heteroaryl, heteroarylalkyl, heteroarylalkenyl, heterocycle and heterocyclic alkyl each optionally has a substituent, or a pharmacologically acceptable salt thereof.

6. A compound of the formula (XXVI)

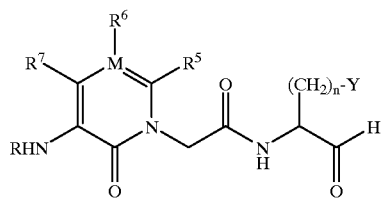

R is a hydrogen atom, alkyl, —CHO, —$CONH_2$, —$COR^1$, —$COOR^1$, —$CONHOR^1$, —$CONHR^1$,—$CONR^1R^{1'}$, —$CONHSO_2R^1$, —$COSR^1$, —$COCOR^2$, —$COCOOR^2$, —$CONHCOOR^2$, —$COCONR^3R^4$, —$CSXR^1$, —$SO_2WR^1$, —$SO_2NR^1R^{1'}$ or —$SO_3E$ wherein $R^1$ and $R^{1'}$ may be the same or different and each is independently alkyl, cycloalkyl, cycloalkylalkyl, aryl, arylalkyl, heteroaryl, heteroarylalkyl, heterocycle or heterocyclic alkyl, $R^2$, $R^3$ and $R^4$ may be the same or different and each is independently a hydrogen atom, alkyl or arylalkyl, or —$NR^3R^4$ may in combination form a heterocycle, X is a single bond, —NH—, —O— or —S—, W is a single bond, —NH—, —NHCO—, —NHCOO— or —NHCONH—, and E is a hydroxyl group or amino;

$R^5$ and $R^7$ may be the same or different and each is independently hydrogen atom or alkyl, or one of $R^5$ and $R^7$ is aryl, arylalkyl, arylalkenyl, heteroaryl, heteroarylalkyl or heteroarylalkenyl and the rest is hydrogen atom;

M is nitrogen atom, $R^6$ is void;

Y is cycloalkyl, aryl or heteroaryl; and n is 0 or 1, wherein, of the above-mentioned groups, alkyl, cycloalkyl, cycloalkylalkyl, aryl, arylalkyl, arylalkenyl, heteroaryl, heteroarylalkyl, heteroarylalkenyl, heterocycle and heterocyclic alkyl each optionally has a substituent, or a pharmacologically acceptable salt thereof.

7. The heterocyclic amide compound of claim 1, wherein, in the formula (I),

R is a hydrogen atom or benzyloxycarbonyl;

$R^5$ is phenyl, 3-fluorophenyl, 4-fluorophenyl, 3-chlorophenyl, 4-chlorophenyl, 3-methylphenyl, 3-methoxyphenyl, 3-nitrophenyl, 3-aminophenyl, 3-pyridyl or 4-pyridyl;

$R^6$ is void;

$R^7$ is a hydrogen atom;

M is a nitrogen atom;

Y is phenyl;

Z is a group of the formula (ia),

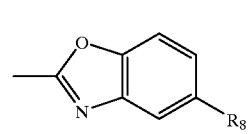

the formula (ib),

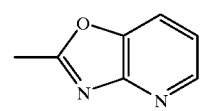

or formula (iiia)

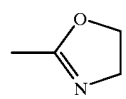

wherein $R^8$ is a hydrogen atom, nitro, —$CONH_2$, —CONHEt, —$CONMe_2$, —$CONEt_2$, —COOMe or —COOEt;

n is 1,
or a pharmacologically acceptable salt thereof.

8. A pharmaceutical composition comprising a heterocyclic amide compound of any of claims 1 to 4 or claim 6 or a pharmacologically acceptable salt thereof, and a pharmacologically acceptable carrier.

9. A method of inhibiting chymase by administering the pharmaceutical composition of claim 8 to a patient in need of same.

* * * * *

UNITED STATES PATENT AND TRADEMARK OFFICE
CERTIFICATE OF CORRECTION

PATENT NO.    : 6,080,738
DATED         : June 27, 2000
INVENTOR(S)   : Fumihiko AKAHOSHI et al.

It is certified that error appears in the above-identified patent and that said Letters Patent is hereby corrected as shown below:

On the abstract page, the Assignee information should be:
--[73]  Yoshitomi Pharmaceutical Industries, Ltd., Japan--.

Signed and Sealed this

Eighth Day of May, 2001

Attest:

NICHOLAS P. GODICI

Attesting Officer    Acting Director of the United States Patent and Trademark Office